United States Patent
Cui et al.

(10) Patent No.: US 10,138,222 B2
(45) Date of Patent: Nov. 27, 2018

(54) SUBSTITUTED BENZAMIDES AS RIPK2 INHIBITORS

(71) Applicant: Boehringer Ingelheim International GmbH, Ingelheim am Rhein (DE)

(72) Inventors: Jianwen Cui, Woodbridge, CT (US); Donghong Amy Gao, Ridgefield, CT (US); Pingrong Liu, Southbury, CT (US); Bryan Patrick McKibben, New Milford, CT (US); Craig Andrew Miller, New Milford, CT (US); Hossein Razavi, Danbury, CT (US); Elizabeth Spencer, Southbury, CT (US); Sabine Ruppel, New Milford, CT (US); Anil K. Padyana, Lexington, MA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/696,547

(22) Filed: Sep. 6, 2017

(65) Prior Publication Data

US 2018/0072703 A1   Mar. 15, 2018

Related U.S. Application Data

(60) Provisional application No. 62/394,780, filed on Sep. 15, 2016.

(51) Int. Cl.
| | |
|---|---|
| A61K 31/166 | (2006.01) |
| C07C 237/38 | (2006.01) |
| C07D 401/14 | (2006.01) |
| C07D 401/04 | (2006.01) |
| C07D 405/14 | (2006.01) |
| C07D 413/14 | (2006.01) |
| C07D 493/08 | (2006.01) |
| C07D 451/02 | (2006.01) |
| C07D 403/04 | (2006.01) |

(52) U.S. Cl.
CPC ......... *C07D 401/14* (2013.01); *C07D 401/04* (2013.01); *C07D 403/04* (2013.01); *C07D 405/14* (2013.01); *C07D 413/14* (2013.01); *C07D 451/02* (2013.01); *C07D 493/08* (2013.01)

(58) Field of Classification Search
CPC .................... A61K 31/166; C07C 237/38
USPC ........................... 514/617; 564/161
See application file for complete search history.

(56) References Cited

U.S. PATENT DOCUMENTS

| | | | |
|---|---|---|---|
| 2013/0023532 A1 | 1/2013 | Casillas et al. | |
| 2015/0353500 A1* | 12/2015 | Maue ................... | C07D 401/12 514/255.05 |
| 2018/0072717 A1 | 3/2018 | Liu et al. | |

FOREIGN PATENT DOCUMENTS

| | | |
|---|---|---|
| WO | 2011123609 A1 | 10/2011 |
| WO | 2014122083 A1 | 8/2014 |
| WO | 2016065461 A1 | 5/2016 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/US2017/050197, dated Nov. 21, 2017.
International Search Report for PCT/US2017/050200 dated Oct. 13, 2017.
Kopalli, Spandana Rajendra et al. "Necroptosis inhibitors as therapeutic targets in inflammation mediated disorders—a review of the current literature and patents" (2016) Expert Opinion on Therapeutic Patents, vol. 26, No. 11, 1239-1256.

* cited by examiner

*Primary Examiner* — Douglas M Willis
(74) *Attorney, Agent, or Firm* — Edouard G Lebel

(57) ABSTRACT

The present invention relates to compounds of formula (I):

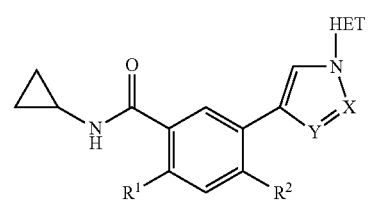

or pharmaceutically acceptable salts thereof, wherein $R^1$—, $R^2$—, X, Y, and HET are as defined herein. The invention also relates to pharmaceutical compositions comprising these compounds, methods of using these compounds in the treatment of various diseases and disorders, processes for preparing these compounds and intermediates useful in these processes.

33 Claims, 4 Drawing Sheets

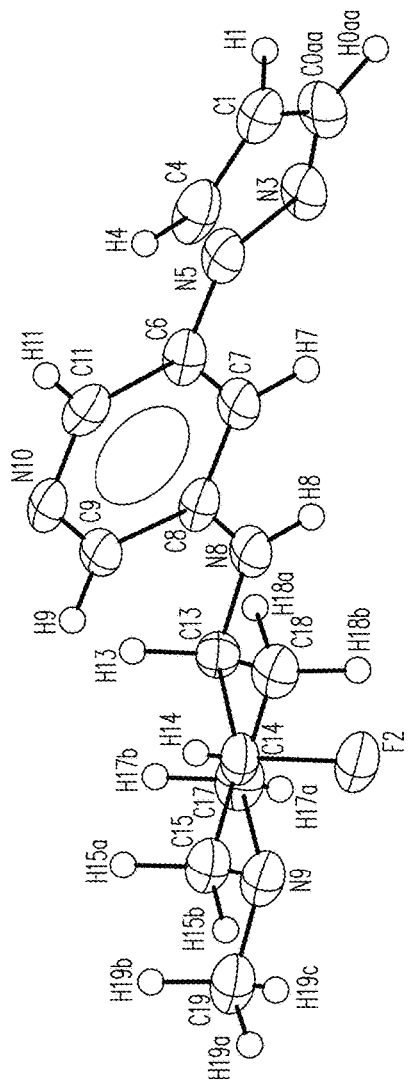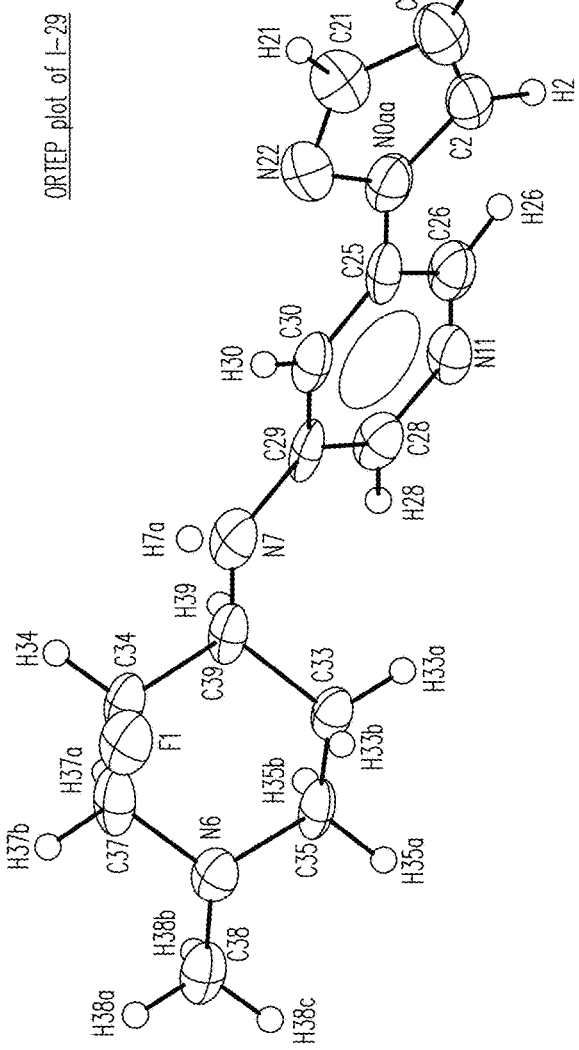
FIG. 2

SUBSTITUTED BENZAMIDES AS RIPK2 INHIBITORS

BACKGROUND OF THE INVENTION

1. Technical Field

The present invention relates to a series of novel N-cyclopropyl benzamide compounds, the synthesis of these compounds their use in the treatment of inflammatory disease and pharmaceutical compositions comprising these compounds

2. Background Information

RIPK2 (also known as RICK, CARDIAK, CARDS, or RIP2) is a dual specific serine/threonine and tyrosine kinase which is a key component of pro-inflammatory signaling through the NOD1 and NOD2 signaling pathways (Inohara et al. 1998; McCarthy et al. 1998; Thome et al. 1998; Tigno-Aranjuez et al. 2010). The NOD receptors are one of the mechanisms for surveillance for intracellular bacterial pathogens. Bacterial cell wall components initiate signals through the NOD1 and NOD2 pathway by the binding of NOD1 bacteria ligands, D-glutamyl-meso-diaminopimelic acid, and the NOD2 ligand, muramyl dipeptide, to the appropriate intracellular NOD receptors (Girardin et al. 2003a; Girardin et al. 2003b; Girardin et al. 2003c; Chamaillard et al. 2003; Inohara et al. 2003). This binding induces oligomerization of the NOD protein through homotypic CARD/CARD domain interactions (Inohara et al. 2000; Ogura et al. 2001). This activation of NOD receptors leads to Lys63-linked polyubiquitination of RIPK2 through activation of ubiquitin E3 ligases such as XIAP, cIAP1, cIAP2, TRAF2, TRAF5, and TRAF6 (Krieg et al. 2009; Bertrand et al. 2009; Yang et al. 2007; Hasegawa et al. 2008) and recruits the linear ubiquitin system (LUBAC) (Damgaard et al. 2012; Ver Heul et al. 2013). Additionally, RIPK2 undergoes autophosphorylation of Tyrosine474 as part of its activation and assembly into the NOD signaling complex (Tigno-Aranjuez et al. 2010). Further RIPK2, dependent assembly of the signaling complex results in the activation of IKKα/β/γ and TAK1, leading to activation of NF-κB and MAPK pathways resulting in the production of proinflammatory cytokines (Yang et al. 2007).

Mutations in NOD2 have been linked to multiple diseases. Activating mutations have been linked to Early Onset Sarcoidosis (Kanazawa et al., 2005) and Blau syndrome (Miceli-Richard et al., 2001) which affect skin, joints, and eyes. These activating mutations result in increased basal NF-κB activity (Kanazawa et al., 2005). Loss-of-function mutations in the NOD2 LRR are linked to Crohn's Disease (Ogura et al. 2001; Hugot et al. 2001; Hampe et al. 2001; Hampe 2002; Lesange 2002). In addition, polymorphisms in NOD1 have been linked to atopy (Weidinger et al. 2005) and asthma (Hysi et al. 2005). Additional studies in cellular and in vivo mouse models have suggested a role for NOD1 and NOD2 signaling in a variety of diseases such as Graft vs. Host Disease, Arthritis, Multiple Sclerosis, and Diabetic Nephropathy (Peaneck et al. 2009; Saha et al. 2009; Vieira et al. 2012; Rosenzweig et al. 2010; Joosten et al. 2008; Shaw et al. 2011; Du et al. 2013). Small molecule inhibitors of RIP2 kinase (RIPK2) are disclosed in US2013/0023532 A1 but appear to have limited potency.

Pharmacological inhibition of RIPK2 by a potent and selective small molecule inhibitor will attenuate pro-inflammatory signaling through the bacterial sensing pathways initiated by NOD1 and NOD2 stimulation. This reduction in inflammatory signaling will provide therapeutic benefit in a variety of autoinflammatory diseases. Thus, there is a need for potent inhibitors of RIPK2 for pharmaceutical purposes.

BRIEF SUMMARY OF THE INVENTION

The present invention provides novel 6-membered heteroaryl based phenyl azole series of compounds which inhibit the receptor-interacting serine/threonine protein kinase 2 (RIPK2) and are thus useful for treating a variety of diseases and disorders that are mediated or sustained through the activity of RIPK2 including inflammatory, cardiometabolic and cardiovascular diseases and cancer. This invention also relates to pharmaceutical compositions comprising these compounds, methods of using these compounds in the treatment of various diseases and disorders, processes for preparing these compounds and intermediates useful in these processes. In one aspect of the invention, a compound of this invention has good binding potency.

In another aspect of the invention, a compound this invention exhibits good cellular potency.

In yet another aspect, a compound of this invention exhibits good stability.

In another aspect, a compound of this invention exhibits good cell permeability.

DETAILED DESCRIPTION OF THE INVENTION

In its broadest embodiment, the present invention relates to compounds of formula I:

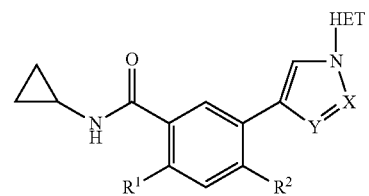

or pharmaceutically acceptable salts thereof, wherein:
HET is selected from:

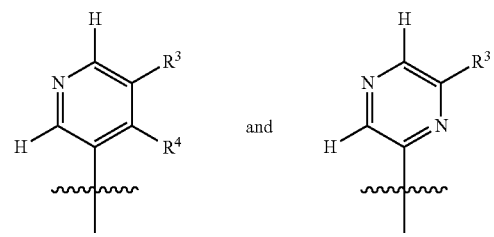

X is N and Y is CH; or
X is CH and Y is N;
$R^1$ is hydrogen or F;
$R^2$ is $C_{1-3}$ alkyl, Cl or F;
$R^3$ and $R^4$ are each independently selected from:
(a) —H,
(b) —$OR^5$,
(c) —O—$C_{1-6}$alkyl-O—$C_{1-3}$ alkyl
(d) —O—$C_{3-6}$ cycloalkyl,
(e) —C(O)$R^5$, (f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —$N(R^5)(R^6)$, CN or —$C(O)N(R^5)(R^6)$, (g) $C_{3-6}$ cycloalkyl optionally substituted with one to three —OH, one to three fluorine, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, $N(R^5)(R^6)$, or —$C(O)N(R^5)(R^6)$, (h) —$CO_2R^5$,
(i) —$C(O)N(R^5)(R^6)$,
(j) —$S(O)_2N(R^5)(R^6)$,
(k) —$S(O)_n$—$R^5$
(l) 4-10 membered monocyclic, bicyclic or spirocyclic heterocyclyl group containing N, S or O optionally substituted with 1-3 groups selected from —$N(R^5)(R^6)$, halogen, —$C_{1-6}$ alkyl, —O—$C_{1-6}$ alkyl and —$C_{1-6}$ alkyl-halogen,
(m) aryl,
(n) —$N(R^5)(R^6)$,
(o) halogen;

$R^5$ and $R^6$ are each independently selected from —H, —$(C_1-C_6)$alkyl-heterocyclyl, 4-6 membered heterocyclyl wherein the heterocyclic ring is optionally substituted with 1-3 substituents selected from —$(C_1-C_6)$alkyl, —O—$C_{1-6}$ alkyl, —$C_{1-6}$ alkyl-halogen, —$(C_1-C_6)$cycloalkyl, halogen, acyl, heterocyclyl, heterocyclyl-$(C_1-C_6)$alkyl, heterocyclyl —O—$(C_1-C_6)$alkyl, heterocyclyl-OH, heterocyclyl-C(O)-Me, heterocyclyl-C(O)—O($C_1-C_3$) alkyl, —$(C_1-C_6)$alkyl-heterocyclyl, —$(C_1-C_6)$alkyl-heterocyclyl-$(C_1-C_6)$alkyl, —$(C_1-C_6)$alkyl-O—H, —$(C_1-C_6)$alkyl-O—$(C_1-C_6)$alkyl-, $C_{3-6}$ cycloalkyl, —$(C_1-C_6)$alkyl-cycloalkyl, $C_{3-6}$ cycloalkyl-$(C_1-C_6)$alkyl, $C_{3-6}$ cycloalkyl-O—$(C_1-C_6)$alkyl, and $C_{3-6}$ cycloalkyl-O—$(C_1-C_6)$alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, C(O)—$C_{3-6}$ cycloalkyl; —C(O)—NH—$C_1-C_3$ alkyl, —C(O)—NH—$C_1-C_3$ alkyl, —C(O)—NH—$C_3-C_6$ cycloalkyl optionally mono or di substituted with —$(C_1-C_3)$—OH, —C(O)—NH—$C_3-C_6$ heterocyclyl, —C(O)-aryl, —C(O)-heteroaryl —S(O)n-$C_1-C_3$-alkyl and —$(C_1-C_6)$ alkyl optionally substituted with —OH, O—$(C_1-C_3)$-alkyl, $C_{3-6}$ cycloalkyl, heterocyclyl, aryl, —NH—$C_{1-3}$ alkyl or —N—$(C_{1-3}$-alkyl$)_2$; or $R^5$ and $R^6$ together with the nitrogen atom to which they are attached form a 5-6 membered heterocyclic ring optionally substituted with methyl; and n is 0, 1, or 2.

In a second embodiment, the present invention relates to a compound as described in the broadest embodiment above, or a pharmaceutically acceptable salt thereof, wherein:
HET is:

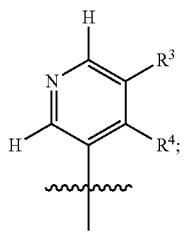

X is N and Y is CH;
$R^1$ is hydrogen or F;
$R^2$ is $C_{1-3}$ alkyl, Cl or F;
$R^3$ and $R^4$ are each independently selected from:
(a) —H,
(b) —$OR^5$,
(c) —O—$C_{1-6}$alkyl-O—$C_{1-3}$ alkyl
(d) —O—$C_{3-6}$ cycloalkyl,
(e) —$C(O)R^5$,
(f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —$N(R^5)(R^6)$, CN or —$C(O)N(R^5)(R^6)$,
(g) $C_{3-6}$ cycloalkyl optionally substituted with one to three —OH, one to three fluorine, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, $N(R^5)(R^6)$, or —$C(O)N(R^5)(R^6)$,
(h) —$CO_2R^5$,
(i) —$C(O)N(R^5)(R^6)$,
(j) —$S(O)_2N(R^5)(R^6)$,
(k) —$S(O)_n$—$R^5$
(l) 4-10 membered monocyclic, bicyclic or spirocyclic heterocyclyl group containing N, S or O,
(m) aryl,
(n) —$N(R^5)(R^6)$,
(o) halogen;

$R^5$ and $R^6$ are each independently selected from —H, 4-6 membered heterocyclyl wherein the heterocyclic ring is optionally substituted with 1-3 substituents selected from —$(C_1-C_6)$alkyl, —$(C_1-C_6)$cycloalkyl, halogen, acyl, heterocyclyl, heterocyclyl-$(C_1-C_6)$alkyl, heterocyclyl —O—$(C_1-C_6)$alkyl, heterocyclyl-OH, heterocyclyl-C(O)-Me, heterocyclyl-C(O)—O($C_1-C_3$) alkyl, —$(C_1-C_6)$alkyl-heterocyclyl, —$(C_1-C_6)$alkyl-heterocyclyl-$(C_1-C_6)$alkyl, —$(C_1-C_6)$alkyl-O—H, —$(C_1-C_6)$alkyl-O—$(C_1-C_6)$alkyl-, $C_{3-6}$ cycloalkyl, —$(C_1-C_6)$alkyl-cycloalkyl, $C_{3-6}$ cycloalkyl-$(C_1-C_6)$alkyl, $C_{3-6}$ cycloalkyl-O—$(C_1-C_6)$alkyl, and $C_{3-6}$ cycloalkyl-O—$(C_1-C_6)$alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1-C_3$ alkyl, —C(O)—NH—$C_1-C_3$ alkyl, —C(O)—NH—$C_3-C_6$ cycloalkyl optionally mono or di substituted with —$(C_1-C_3)$—OH, —C(O)—NH—$C_3-C_6$ heterocyclyl, —C(O)-aryl, —C(O)-heteroaryl —S(O)n-$C_1-C_3$-alkyl and —$(C_1-C_6)$alkyl optionally substituted with —OH, O—$(C_1-C_3)$-alkyl, $C_{3-6}$ cycloalkyl, heterocyclyl, aryl, —NH—$C_{1-3}$ alkyl or —N—$(C_{1-3}$-alkyl$)_2$; or $R^5$ and $R^6$ together with the nitrogen atom to which they are attached form a 5-6 membered heterocyclic ring optionally substituted with methyl; and n is 1, or 2.

In a third embodiment, the present invention relates to a compound as described in the broadest embodiment above, or a pharmaceutically acceptable salt thereof, wherein:
HET is:

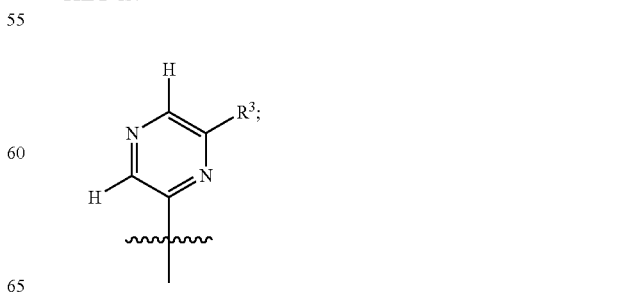

X is N and Y is CH.

In a fourth embodiment, the present invention relates to a compound as described in the broadest embodiment above, or a pharmaceutically acceptable salt thereof, wherein:
HET is:

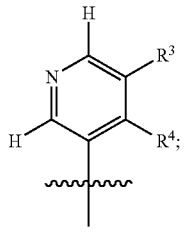

X is CH and Y is N.

In a fifth embodiment, the present invention relates to a compound as described in the broadest embodiment above, or a pharmaceutically acceptable salt thereof, wherein:
HET is:

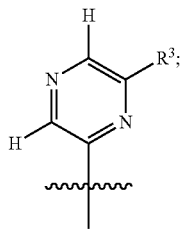

X is CH and Y is N.

In a sixth embodiment, the present invention relates to a compound as described in the broadest embodiment above, or a pharmaceutically acceptable salt thereof, wherein:
HET is:

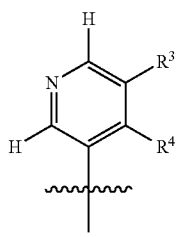

X is N and Y is CH;
$R^1$ is selected from H or F;
$R^2$ is selected from methyl and Cl;
$R^3$ is selected from:
(a) —H,
(b) —$OR^5$,
(c) —O—$C_{1-6}$alkyl-O—$C_{1-3}$ alkyl
(d) —O—$C_{3-6}$ cycloalkyl,
(e) —C(O)$R^5$,
(f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —N($R^5$)($R^6$), CN, or —C(O)N($R^5$)($R^6$),
(g) $C_{3-6}$ cycloalkyl optionally substituted with one to three —OH, one to three fluorine, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, N($R^5$)($R^6$),
or —C(O)N($R^5$)($R^6$),
(h) —$CO_2R^5$,
(i) —C(O)N($R^5$)($R^6$),
(j) —S(O)$_2$N($R^5$)($R^6$),
(k) —S(O)$_n$—$R^5$
(l) 4-10 membered monocyclic, bicyclic or spirocyclic heterocyclyl group containing N, S or O,
(m) aryl,
(n) —N($R^5$)($R^6$),
(o) halogen;
$R^4$ is H;
$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —S(O)n-$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or
$R^5$ and $R^6$ together with the nitrogen atom to which they are attached form a 5-6 membered heterocyclic ring optionally substituted with methyl; and
n is 2.

In a seventh embodiment, the present invention relates to a compound as described in the sixth embodiment above, or a pharmaceutically acceptable salt thereof, wherein:
HET is:

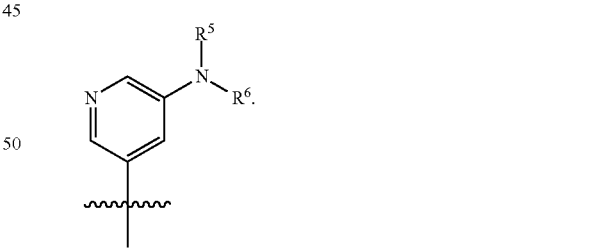

$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—C$_{1-3}$ alkyl-O-Me, —C(O)—C$_{1-3}$ alkyl, —C(O)—C$_{3-6}$ cycloalkyl; —C(O)—NH—C$_1$-C$_3$ alkyl, —C(O)—NH—C$_1$-C$_3$ alkyl, —C(O)—NH—C$_3$-C$_6$ cycloalkyl optionally mono or di substituted with —(C$_1$-C$_3$)—OH, —C(O)—NH—C$_3$-C$_6$ heterocyclyl, —C(O)-aryl, —C(O)-heteroaryl —S(O)$_2$—C$_1$-C$_3$-alkyl and —(C$_1$-C$_6$)alkyl optionally substituted with —OH, O—(C$_1$-C$_3$)-alkyl, C$_{3-6}$ cycloalkyl, heterocyclyl, aryl, —NH—C$_{1-3}$ alkyl or —N—(C$_{1-3}$-alkyl)$_2$; or R$^5$ and R$^6$ together with the nitrogen atom to which they are attached form a 5-6 membered heterocyclic ring optionally substituted with methyl.

In an eighth embodiment, the present invention relates to a compound as described in the sixth embodiment above, or a pharmaceutically acceptable salt thereof, wherein:

HET is selected from:

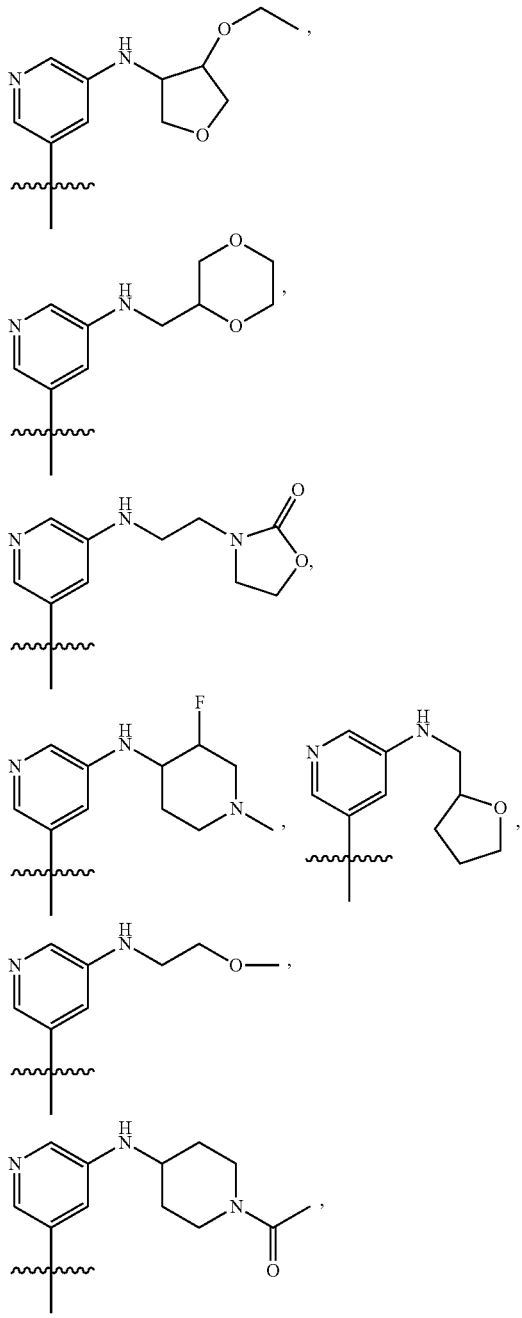

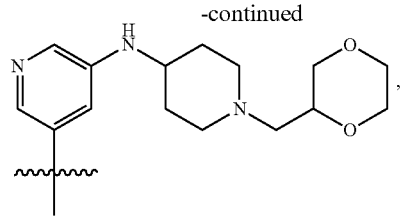

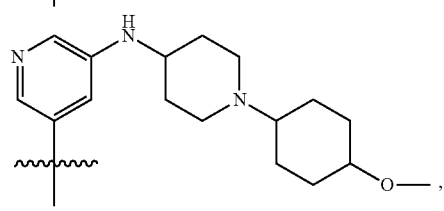

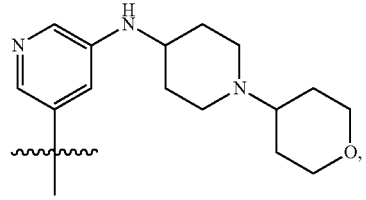

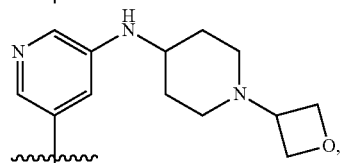

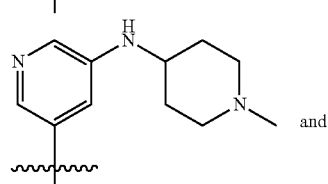

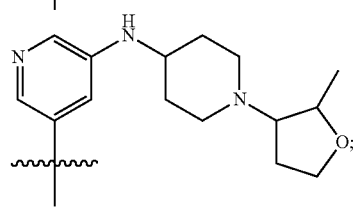

X is N and Y is CH;
R$^1$ is selected from H or F; and
R$^2$ is selected from methyl and Cl.

In a ninth embodiment, the present invention relates to a compound as described in the broadest embodiment above, or a pharmaceutically acceptable salt thereof, wherein:

HET is:


X is CH;

Y is N;

$R^1$ is selected from H or F;

$R^2$ is selected from methyl and Cl;

$R^3$ is selected from:

(a) —H, (b) —$OR^5$, (c) —O—$C_{1-6}$alkyl-O—$C_{1-3}$ alkyl (d) —O—$C_{3-6}$ cycloalkyl, (e) —$C(O)R^5$, (f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —$N(R^5)(R^6)$, CN, or —$C(O)N(R^5)(R^6)$, (g) $C_{3-6}$ cycloalkyl optionally substituted with one to three —OH, one to three fluorine, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, $N(R^5)(R^6)$, or —$C(O)N(R^5)(R^6)$, (h) —$CO_2R^5$, (i) —$C(O)N(R^5)(R^6)$, (j) —$S(O)_2N(R^5)(R^6)$, (k) —$S(O)_n$—$R^5$ (l) 4-10 membered monocyclic, bicyclic or spirocyclic heterocyclyl group containing N, S or O, (m) aryl, (n) —$N(R^5)(R^6)$, (o) halogen;

$R^4$ is H;

$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —$S(O)_2$—$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or $R^5$ and $R^6$ together with the nitrogen atom to which they are attached form a 5-6 membered heterocyclic ring optionally substituted with methyl; and n is 2.

In a tenth embodiment, the present invention relates to a compound as described in the ninth embodiment above, or a pharmaceutically acceptable salt thereof, wherein:

HET is:

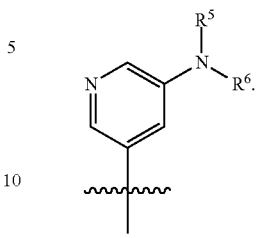

$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —$S(O)_2$—$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or $R^5$ and $R^6$ together with the nitrogen atom to which they are attached form a 5-6 membered heterocyclic ring optionally substituted with methyl.

In embodiment eleven, the present invention relates to a compound of formula (I) according to the broadest embodiment, or a pharmaceutically acceptable salt thereof, wherein:

HET is selected from:

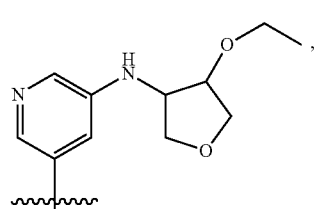

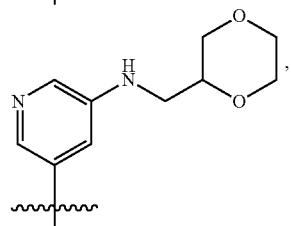

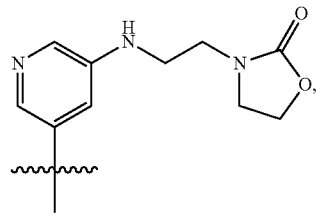

X is N and Y is CH;
R¹ is F; and
R² is methyl.

In embodiment twelve, the present invention relates to a compound as described in the broadest embodiment above, or a pharmaceutically acceptable salt thereof, wherein:
HET is:

X is N;
Y is CH;
R¹ is selected from H or F;
R² is selected from methyl and Cl;
R³ is selected from:
(a) —H,
(b) —OR⁵,
(c) —O—$C_{1-6}$alkyl-O—$C_{1-3}$ alkyl
(d) —O—$C_{3-6}$ cycloalkyl,
(e) —C(O)R⁵,
(f) $C_{1-6}$alkyl optionally substituted with one to three —OH, fluorine, heterocyclyl optionally substituted with oxo, $C_{3-6}$ cycloalkyl, —$CO_2R^5$, —O—$C_{1-6}$alkyl, aryl, —N(R⁵)(R⁶), CN, or —C(O)N(R⁵)(R⁶),
(g) $C_{3-6}$ cycloalkyl optionally substituted with one to three —OH, one to three fluorine, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, N(R⁵)(R⁶),
or —C(O)N(R⁵)(R⁶),
(h) —$CO_2R^5$,
(i) —C(O)N(R⁵)(R⁶),
(j) —$S(O)_2N(R^5)(R^6)$,
(k) —$S(O)_n$—R⁵
(l) 4-10 membered monocyclic, bicyclic or spirocyclic heterocyclyl group containing N, S or O,
(m) aryl,
(n) —N(R⁵)(R⁶),
(o) halogen;

R⁵ and R⁶ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl- O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —S(O)n-$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or $R^5$ and $R^6$ together with the nitrogen atom to which they are attached form a 5-6 membered heterocyclic ring optionally substituted with methyl; and n is 2.

In a thirteenth embodiment, the present invention relates to a compound as described in embodiment twelve above, or a pharmaceutically acceptable salt thereof, wherein:

HET is:

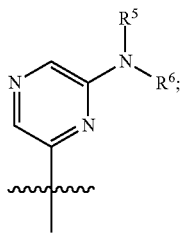

$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —S(O)$_2$—$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or $R^5$ and $R^6$ together with the nitrogen atom to which they are attached form a 5-6 membered heterocyclic ring optionally substituted with methyl.

In embodiment fourteen, the present invention relates to a compound as described in the broadest embodiment above, or a pharmaceutically acceptable salt thereof, wherein:

HET is:

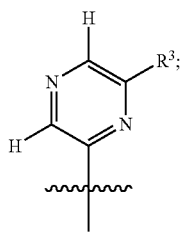

X is CH;

Y is N;

$R^1$ is selected from H or F;

$R^2$ is selected from methyl and Cl;

$R^3$ is selected from:

(a) —H, (b) —OR$^5$, (c) —O—$C_{1-6}$alkyl-O—$C_{1-3}$ alkyl (d) —O—$C_{3-6}$ cycloalkyl, (e) —C(O)R$^5$, (f) $C_{1-6}$alkyl optionally substituted with one to three —OH, fluorine, heterocyclyl optionally substituted with oxo, $C_{3-6}$ cycloalkyl, —CO$_2$R$^5$, —O—$C_{1-6}$alkyl, aryl, —N(R$^5$)(R$^6$), CN, or —C(O)N(R$^5$)(R$^6$), (g) $C_{3-6}$ cycloalkyl optionally substituted with one to three —OH, one to three fluorine, $C_{1-6}$alkyl, —OC$_{1-6}$alkyl, $C_{1-6}$alkyl-OC$_{1-6}$alkyl, $C_{1-6}$alkyl-OH, CF$_3$, CN, —OC$_{3-6}$cycloalkyl, —CO$_2$H, —CO$_2$R$^5$, $C_{3-6}$cycloalkyl, 5-6 membered heteroaryl, $C_{3-6}$ heterocyclyl, N(R$^5$)(R$^6$), or —C(O)N(R$^5$)(R$^6$), (h) —CO$_2$R$^5$, (i) —C(O)N(R$^5$)(R$^6$), (j) —S(O)$_2$N(R$^5$)(R$^6$), (k) —S(O)$_n$—R$^5$ (l) 4-10 membered monocyclic, bicyclic or spirocyclic heterocyclyl group containing N, S or O, (m) aryl, (n) —N(R$^5$)(R$^6$), (o) halogen;

$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —S(O)n-$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or $R^5$ and $R^6$ together with the nitrogen atom to which they are attached form a 5-6 membered heterocyclic ring optionally substituted with methyl; and n is 2.

In a fifteenth embodiment, the present invention relates to a compound as described in embodiment fourteen above, or a pharmaceutically acceptable salt thereof, wherein:

HET is:

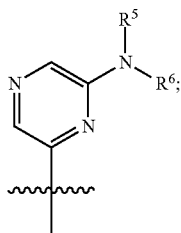

R⁵ and R⁶ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl —O—($C_1$-$C_6$)alkyl, heterocyclyl-OH, heterocyclyl-C(O)-Me, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH; acyl, $C_{3-6}$ cycloalkyl-C(O)—$C_{1-3}$ alkyl, —C(O)—$C_{1-3}$ alkyl-O-Me, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally mono or di substituted with —($C_1$-$C_3$)—OH, —C(O)—NH—$C_3$-$C_6$ heterocyclyl, —C(O)-aryl, —C(O)-heteroaryl —S(O)$_2$—$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or R⁵ and R⁶ together with the nitrogen atom to which they are attached form a 5-6 membered heterocyclic ring optionally substituted with methyl.

In embodiment sixteen, the present invention relates to a compound of formula (I) according to the eleventh embodiment, or a pharmaceutically acceptable salt thereof, wherein:

HET is selected from:

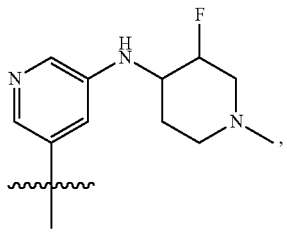

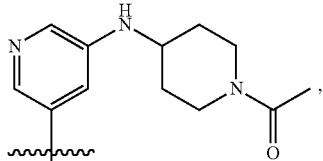

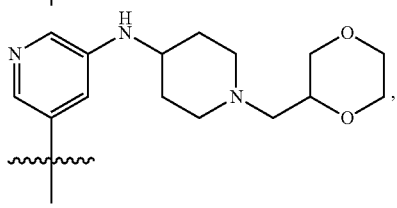

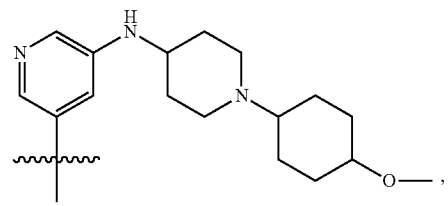

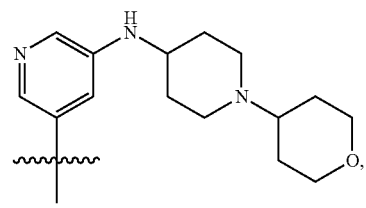

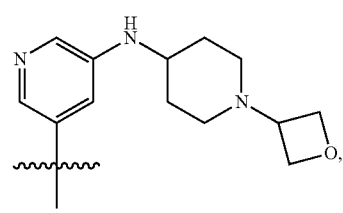

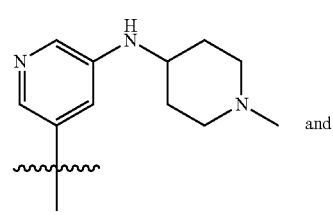

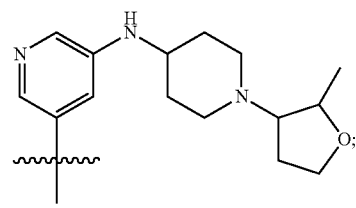 [SMILES: *c1cncc(NC2CCN(C3CCOC3C)CC2)c1]

X is N and Y is CH;
R¹ is F; and
R² is methyl.

In embodiment seventeen, the present invention relates to a compound of formula (I) according to the sixteenth embodiment, or a pharmaceutically acceptable salt thereof, wherein:

HET is:

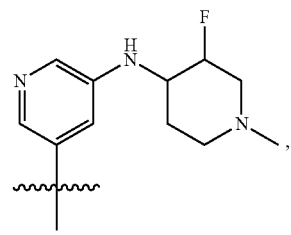

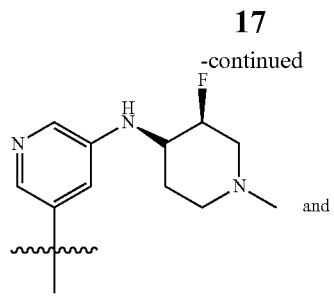
and

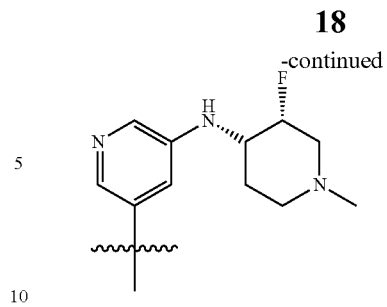

TABLE 1

The following are representative compounds of the invention which can be made by the general synthetic schemes, the examples, and known methods in the art.

| Example | Structure | Structure Name |
|---|---|---|
| 25 | 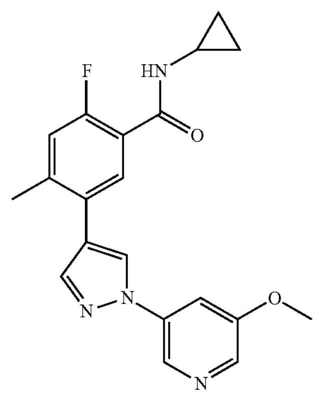 | N-cyclopropyl-2-fluoro-5-[1-(5-methoxypyridin-3-yl)-1H-pyrazol-4-yl]-4-methylbenzamide |
| 26 | 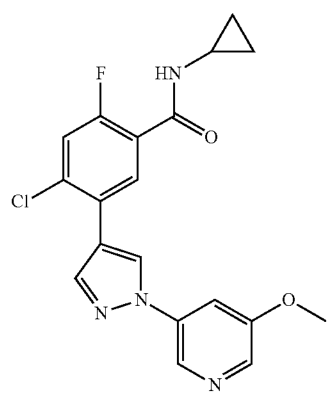 [SMILES: COc1cncc(-n2cc(-c3cc(C(=O)NC4CC4)c(F)cc3Cl)cn2)c1] | 4-chloro-N-cyclopropyl-2-fluoro-5-[1-(5-methoxypyridin-3-yl)-1H-pyrazol-4-yl]benzamide |
| 27 | 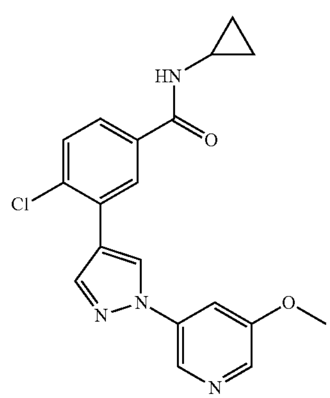 [SMILES: COc1cncc(-n2cc(-c3cc(C(=O)NC4CC4)ccc3Cl)cn2)c1] | 4-chloro-N-cyclopropyl-3-[1-(5-methoxypyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
| --- | --- | --- |
| 28 | 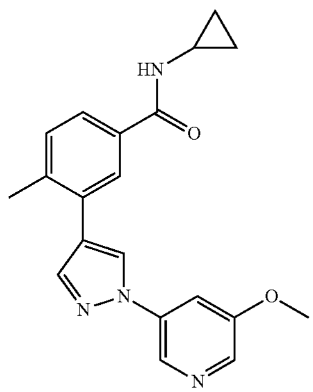 | N-cyclopropyl-3-[1-(5-methoxy-pyridin-3-yl)-1H-pyrazol-4-yl]-4-methylbenzamide |
| 31 | 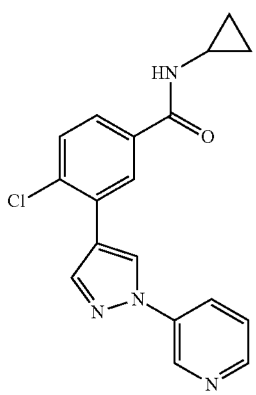 [SMILES: O=C(NC1CC1)c1ccc(Cl)c(-c2cnn(-c3cccnc3)c2)c1] | 4-chloro-N-cyclopropyl-3-[1-(pyridin-3-yl)-1H-pyrazol-4-yl]benzamide |
| 32 | 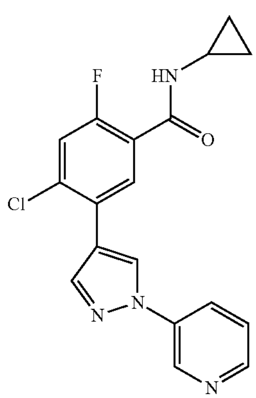 [SMILES: O=C(NC1CC1)c1cc(-c2cnn(-c3cccnc3)c2)c(Cl)cc1F] | 4-chloro-N-cyclopropyl-2-fluoro-5-[1-(pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---|---|---|
| 33 | 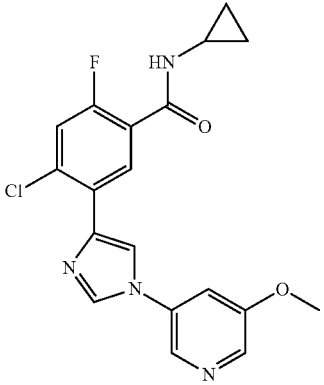 [SMILES: COc1cncc(-n2cnc(-c3cc(C(=O)NC4CC4)c(F)cc3Cl)c2)c1] | 4-chloro-N-cyclopropyl-2-fluoro-5-[1-(5-methoxypyridin-3-yl)-1H-imidazol-4-yl]benzamide |
| 34 | 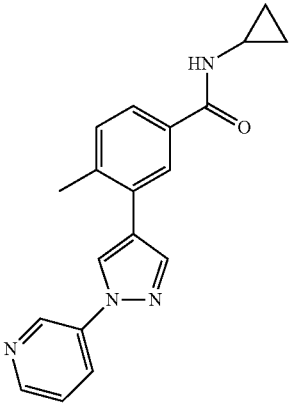 [SMILES: Cc1ccc(C(=O)NC2CC2)cc1-c1cnn(-c2cccnc2)c1] | N-cyclopropyl-4-methyl-3-[1-(pyridin-3-yl)-1H-pyrazol-4-yl]benzamide |
| 35 | 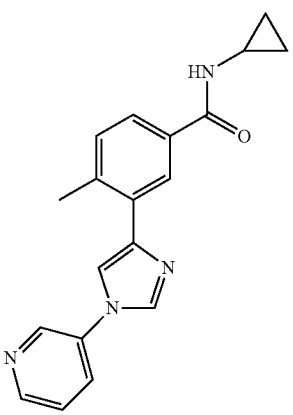 [SMILES: Cc1ccc(C(=O)NC2CC2)cc1-c1cn(-c2cccnc2)cn1] | N-cyclopropyl-4-methyl-3-[1-(pyridin-3-yl)-1H-imidazol-4-yl]benzamide |

TABLE 1-continued

The following are representative compounds of the invention which can be made by the general synthetic schemes, the examples, and known methods in the art.

| Example | Structure | Structure Name |
| --- | --- | --- |
| 36 | 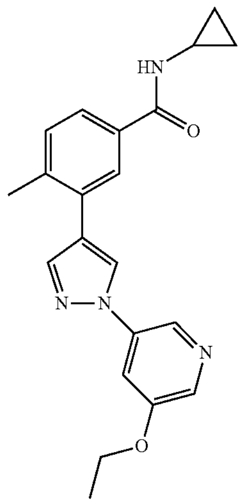 [SMILES: CCOc1cncc(-n2cc(-c3cc(C(=O)NC4CC4)ccc3C)cn2)c1] | N-cyclopropyl-3-[1-(5-ethoxypyridin-3-yl)-1H-pyrazol-4-yl]-4-methyl-benzamide |
| 39 | 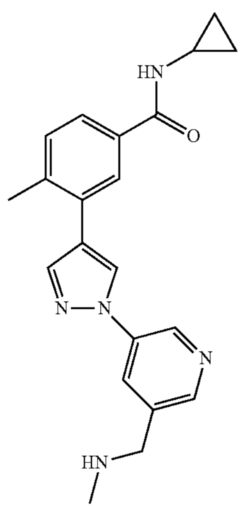 [SMILES: CNCc1cncc(-n2cc(-c3cc(C(=O)NC4CC4)ccc3C)cn2)c1] | N-cyclopropyl-4-methyl-3-(1-{5-[(methylamino)methyl]pyridin-3-yl}-1H-pyrazol-4-yl)benzamide |
| 43 | 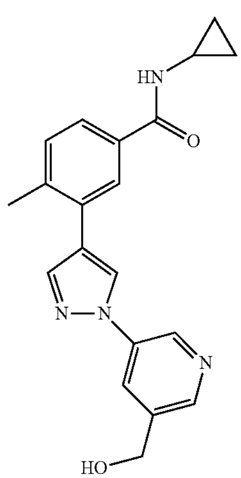 [SMILES: Cc1ccc(C(=O)NC2CC2)cc1-c1cnn(-c2cncc(CO)c2)c1] | N-cyclopropyl-3-{1-[5-(hydroxymethyl)pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 44 | 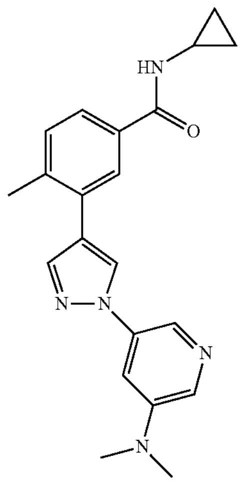 [SMILES: Cc1ccc(C(=O)NC2CC2)cc1-c1cnn(-c2cncc(N(C)C)c2)c1] | N-cyclopropyl-3-{1-[5-(dimethylamino)pyridin-3-yl]-1H-pyrazol-4-yl}-4-methylbenzamide |
| 45 | 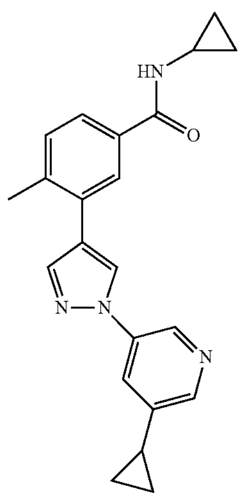 [SMILES: Cc1ccc(C(=O)NC2CC2)cc1-c1cnn(-c2cncc(C3CC3)c2)c1] | N-cyclopropyl-3-[1-(5-cyclopropyl-pyridin-3-yl)-1H-pyrazol-4-yl]-4-methylbenzamide |
| 46 | 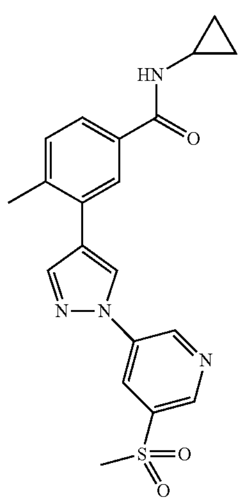 [SMILES: Cc1ccc(C(=O)NC2CC2)cc1-c1cnn(-c2cncc(S(C)(=O)=O)c2)c1] | N-cyclopropyl-3-[1-(5-methanesulfonylpyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 47 | 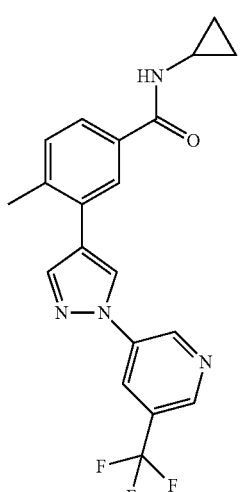 | N-cyclopropyl-4-methyl-3-{1-[5-(trifluoromethyl)pyridin-3-yl]-1H-pyrazol-4-yl}benzamide |
| 48 | 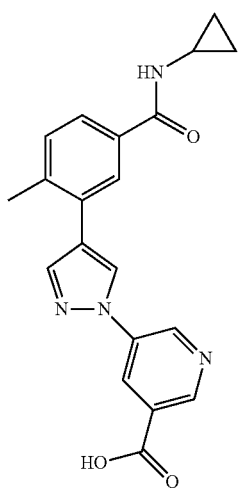 [SMILES: Cc1ccc(C(=O)NC2CC2)cc1-c1cnn(-c2cncc(C(=O)O)c2)c1] | 5-{4-[5-(cyclopropylcarbamoyl)-2-methylphenyl]-1H-pyrazol-1-yl}pyridine-3-carboxylic acid |
| 49 | 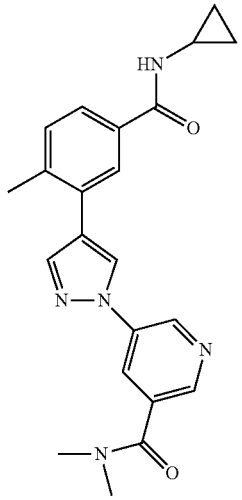 [SMILES: Cc1ccc(C(=O)NC2CC2)cc1-c1cnn(-c2cncc(C(=O)N(C)C)c2)c1] | 5-{4-[5-(cyclopropylcarbamoyl)-2-methylphenyl]-1H-pyrazol-1-yl}-N,N-dimethylpyridine-3-carboxamide |

TABLE 1-continued

The following are representative compounds of the invention which can be made by
the general synthetic schemes, the examples, and known methods in the art.

| Example | Structure | Structure Name |
|---|---|---|
| 50 | 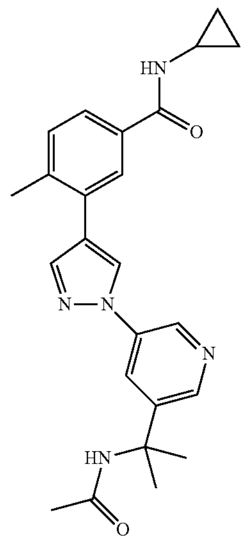 [SMILES: CC(=O)NC(C)(C)c1cncc(-n2cc(-c3cc(C(=O)NC4CC4)ccc3C)cn2)c1] | N-cyclopropyl-3-{1-[5-(2-acetamidopropan-2-yl)pyridin-3-yl]-1H-pyrazol-4-yl}-4-methylbenzamide |
| 51 | 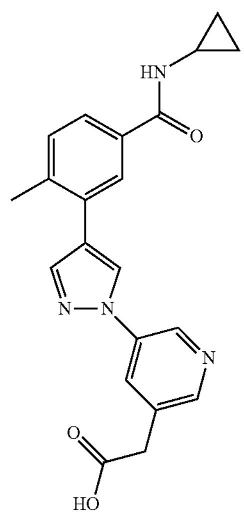 [SMILES: Cc1ccc(C(=O)NC2CC2)cc1-c1cnn(-c2cncc(CC(=O)O)c2)c1] | 2-(5-{4-[5-(cyclopropylcarbamoyl)-2-methylphenyl]-1H-pyrazol-1-yl}pyridin-3-yl)acetic acid |
| 52 | 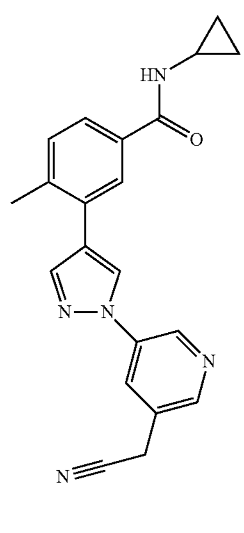 [SMILES: Cc1ccc(C(=O)NC2CC2)cc1-c1cnn(-c2cncc(CC#N)c2)c1] | 3-{1-[5-(cyanomethyl)pyridin-3-yl]-1H-pyrazol-4-yl}-N-cyclopropyl-4-methylbenzamide |

TABLE 1-continued

The following are representative compounds of the invention which can be made by the general synthetic schemes, the examples, and known methods in the art.

| Example | Structure | Structure Name |
|---|---|---|
| 53 | 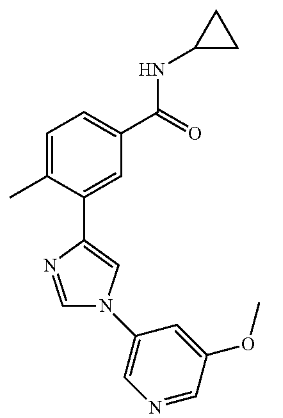 | N-cyclopropyl-3-[1-(5-methoxypyridin-3-yl)-1H-imidazol-4-yl]-4-methyl-benzamide |
| 54 | 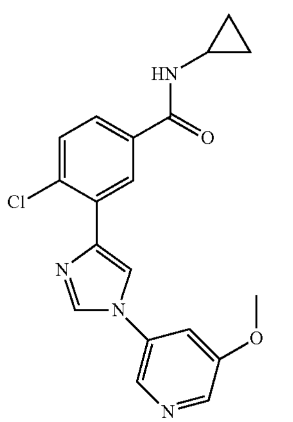 [SMILES: COc1cncc(-n2cnc(-c3cc(C(=O)NC4CC4)ccc3Cl)c2)c1] | 4-chloro-N-cyclopropyl-3-[1-(5-methoxypyridin-3-yl)-1H-imidazol-4-yl]benzamide |
| 55 | 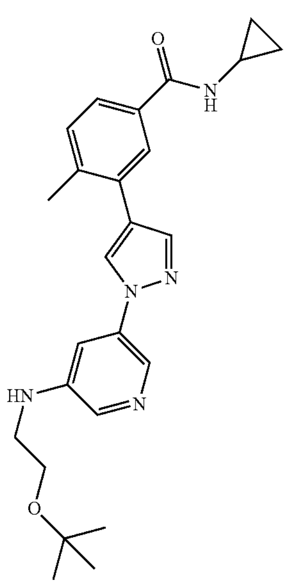 [SMILES: Cc1ccc(C(=O)NC2CC2)cc1-c1cnn(-c2cncc(NCCOC(C)(C)C)c2)c1] | 3-[1-(5-{[2-(tert-butoxy)ethyl]amino}pyridin-3-yl)-1H-pyrazol-4-yl]-N-cyclopropyl-4-methylbenzamide |

TABLE 1-continued

The following are representative compounds of the invention which can be made by the general synthetic schemes, the examples, and known methods in the art.

| Example | Structure | Structure Name |
|---|---|---|
| 56 | 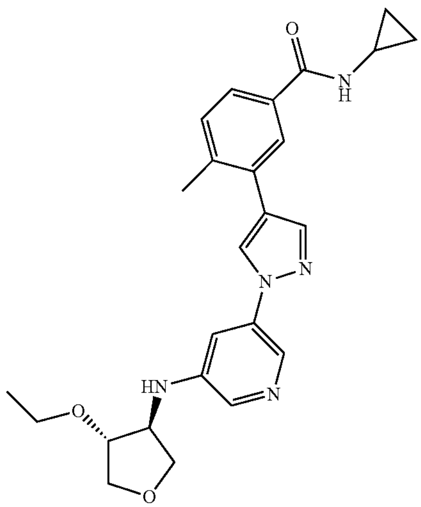 [SMILES: CCO[C@H]1COC[C@@H]1Nc1cncc(-n2cc(-c3cc(C(=O)NC4CC4)ccc3C)cn2)c1] | N-cyclopropyl-3-[1-(5-{[(3S,4R)-4-ethoxyoxolan-3-yl]amino}pyridin-3-yl)-1H-pyrazol-4-yl]-4-methyl-benzamide |
| 57 | 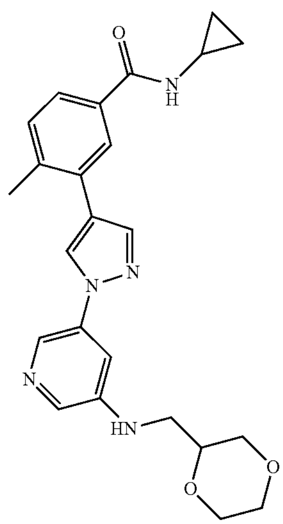 [SMILES: Cc1ccc(C(=O)NC2CC2)cc1-c1cnn(-c2cncc(NCC3COCCO3)c2)c1] | N-cyclopropyl-3-(1-{5-[(1,4-dioxan-2-ylmethyl)amino]pyridin-3-yl}-1H-pyrazol-4-yl)-4-methylbenzamide |
| 58 | 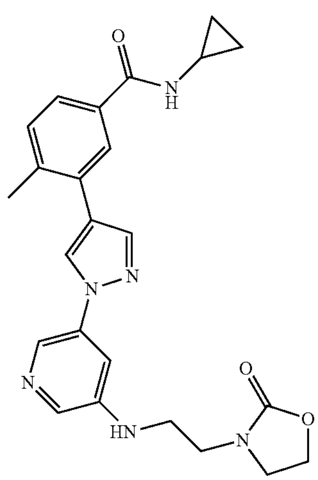 [SMILES: Cc1ccc(C(=O)NC2CC2)cc1-c1cnn(-c2cncc(NCCN3CCOC3=O)c2)c1] | N-cyclopropyl-4-methyl-3-[1-(5-{[2-(2-oxo-1,3-oxazolidin-3-yl)ethyl]amino}pyridin-3-yl)-1H-pyrazol-4-yl]benzamide |

TABLE 1-continued
The following are representative compounds of the invention which can be made by the general synthetic schemes, the examples, and known methods in the art.
| Example | Structure | Structure Name |
|---|---|---|
| 59 | 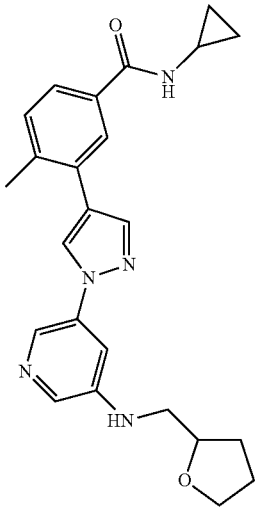 [SMILES: Cc1ccc(C(=O)NC2CC2)cc1-c1cnn(-c2cncc(NCC3CCCO3)c2)c1] | N-cyclopropyl-4-methyl-3-(1-{5-[(oxolan-2-ylmethyl)amino]pyridin-3-yl}-1H-pyrazol-4-yl)benzamide |
| 60 | 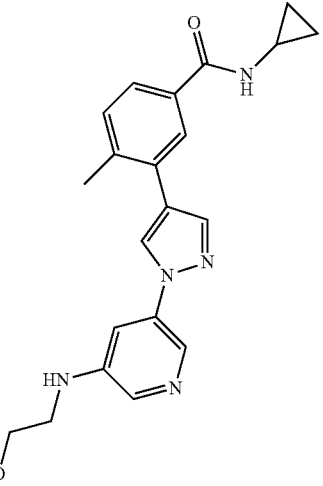 | N-cyclopropyl-3-(1-{5-[(2-methoxyethyl)amino]pyridin-3-yl}-1H-pyrazol-4-yl)-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 63 | 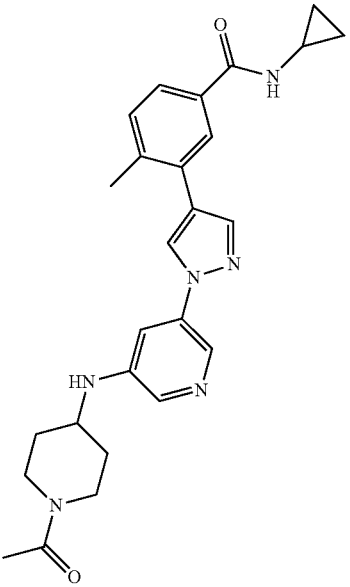 [SMILES: CC(=O)N1CCC(Nc2cncc(-n3cc(-c4cc(C(=O)NC5CC5)ccc4C)cn3)c2)CC1] | 3-(1-{5-[(1-acetylpiperidin-4-yl)amino]pyridin-3-yl}-1H-pyrazol-4-yl)-N-cyclopropyl-4-methyl-benzamide |
| 65 | 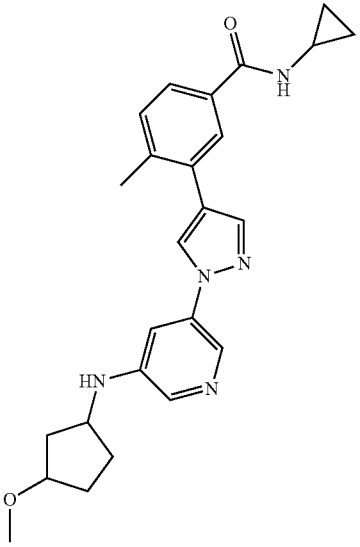 [SMILES: COC1CCC(Nc2cncc(-n3cc(-c4cc(C(=O)NC5CC5)ccc4C)cn3)c2)C1] | N-cyclopropyl-3-(1-{5-[(3-methoxycyclopentyl)amino]pyridin-3-yl}-1H-pyrazol-4-yl)-4-methyl-benzamide |

TABLE 1-continued

The following are representative compounds of the invention which can be made by the general synthetic schemes, the examples, and known methods in the art.

| Example | Structure | Structure Name |
|---------|-----------|----------------|
| 66 | 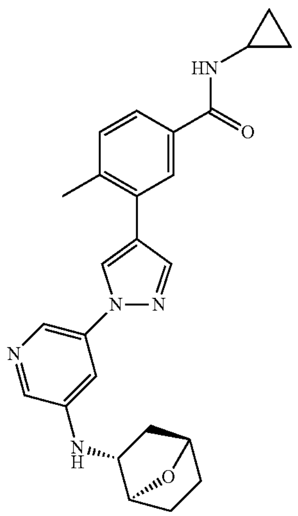 [SMILES: Cc1ccc(C(=O)NC2CC2)cc1-c1cnn(-c2cncc(N[C@@H]3C[C@H]4CC[C@@H]3O4)c2)c1] | N-cyclopropyl-4-methyl-3-[1-(5-{[(1S,2R,4R)-7-oxabicyclo[2.2.1]heptan-2-yl]amino}pyridin-3-yl)-1H-pyrazol-4-yl]benzamide |
| 67 | 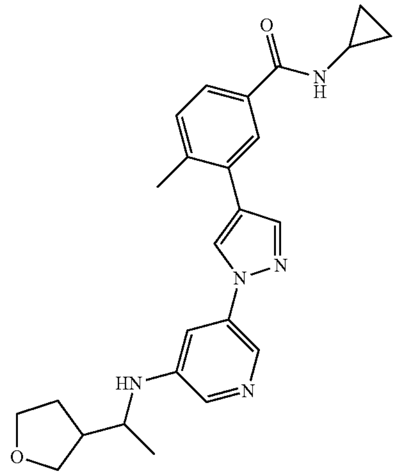 [SMILES: Cc1ccc(C(=O)NC2CC2)cc1-c1cnn(-c2cncc(NC(C)C3CCOC3)c2)c1] | N-cyclopropyl-4-methyl-3-[1-(5-{[1-(oxolan-3-yl)ethyl]amino}pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---------|-----------|----------------|
| 68 | 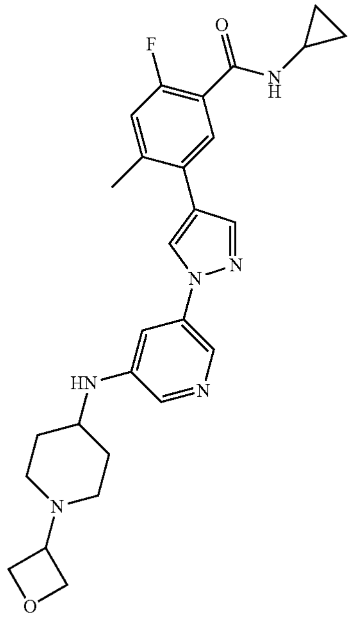 [SMILES: Cc1cc(F)c(C(=O)NC2CC2)cc1-c1cnn(-c2cncc(NC3CCN(C4COC4)CC3)c2)c1] | N-cyclopropyl-2-fluoro-4-methyl-5-[1-(5-{[1-(oxetan-3-yl)piperidin-4-yl]amino}pyridin-3-yl)-1H-pyrazol-4-yl]benzamide |
| 71 | 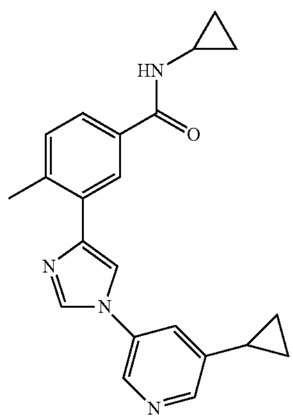 [SMILES: Cc1ccc(C(=O)NC2CC2)cc1-c1cn(-c2cncc(C3CC3)c2)cn1] | N-cyclopropyl-3-[1-(5-cyclopropyl-pyridin-3-yl)-1H-imidazol-4-yl]-4-methylbenzamide |
| 72 | 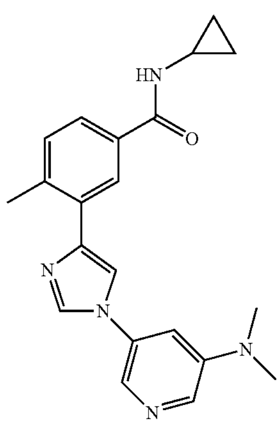 | N-cyclopropyl-3-{1-[5-(dimethyl-amino)pyridin-3-yl]-1H-imidazol-4-yl}-4-methylbenzamide |

TABLE 1-continued

The following are representative compounds of the invention which can be made by the general synthetic schemes, the examples, and known methods in the art.

| Example | Structure | Structure Name |
| --- | --- | --- |
| 73 | 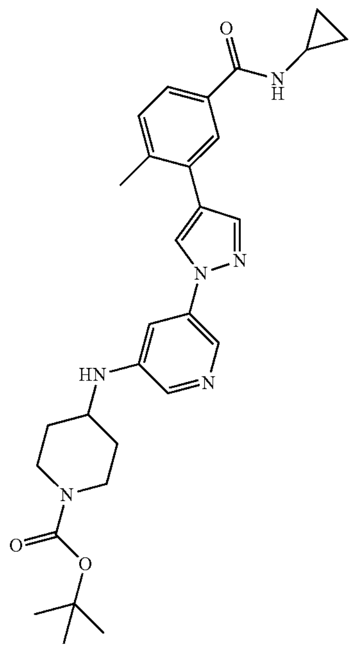 [SMILES: Cc1ccc(C(=O)NC2CC2)cc1-c1cnn(-c2cncc(NC3CCN(C(=O)OC(C)(C)C)CC3)c2)c1] | tert-butyl 4-[(5-{4-[5-(cyclopropylcarbamoyl)-2-methyl-phenyl]-1H-pyrazol-1-yl}pyridin-3-yl)amino]piperidine-1-carboxylate |
| 74 | 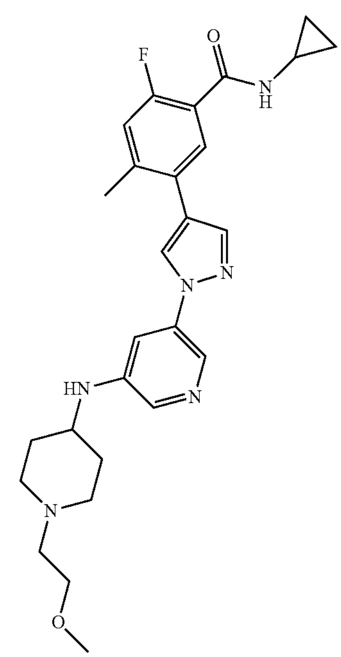 [SMILES: COCCN1CCC(Nc2cncc(-n3cc(-c4cc(C(=O)NC5CC5)c(F)cc4C)cn3)c2)CC1] | N-cyclopropyl-2-fluoro-5-[1-(5-{[1-(2-methoxyethyl)piperidin-4-yl]amino}pyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 75 | 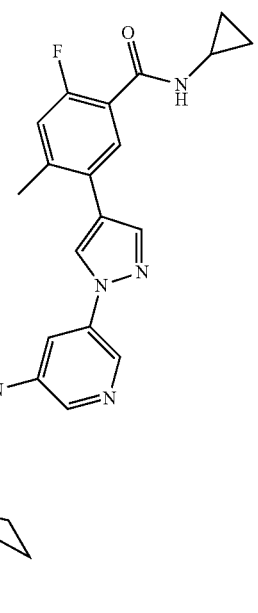 | N-cyclopropyl-2-fluoro-4-methyl-5-[1-(5-{[8-(oxetan-3-yl)-8-azabicyclo[3.2.1]octan-3-yl]amino}pyridin-3-yl)-1H-pyrazol-4-yl]benzamide |
| 76 | 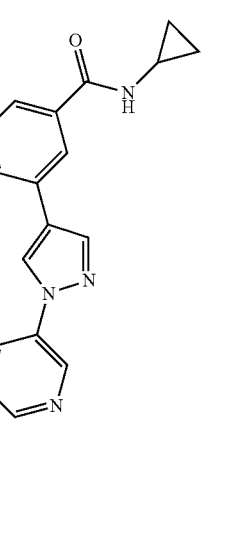 | N-cyclopropyl-4-methyl-3-(1-{5-[(1-methylpiperidin-4-yl)amino]pyridin-3-yl}-1H-pyrazol-4-yl)benzamide |

TABLE 1-continued

The following are representative compounds of the invention which can be made by the general synthetic schemes, the examples, and known methods in the art.

| Example | Structure | Structure Name |
|---|---|---|
| 77 | 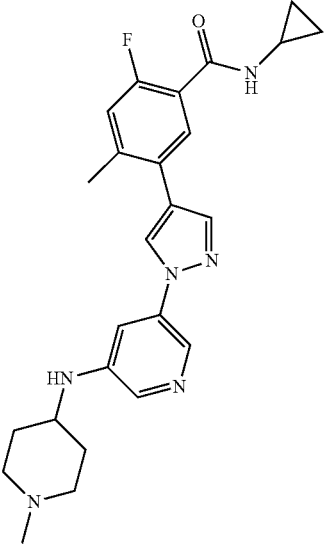 [SMILES: Cc1cc(F)c(C(=O)NC2CC2)cc1-c1cnn(-c2cncc(NC3CCN(C)CC3)c2)c1] | N-cyclopropyl-2-fluoro-4-methyl-5-(1-{5-[(1-methylpiperidin-4-yl)amino]pyridin-3-yl}-1H-pyrazol-4-yl)benzamide |
| 78 | 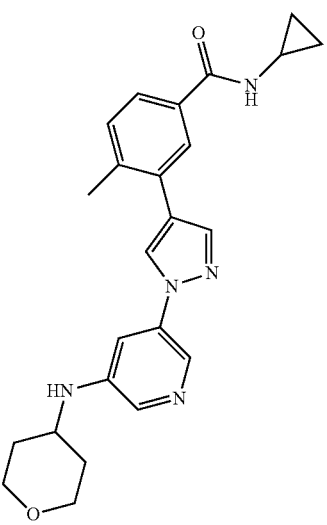 [SMILES: Cc1ccc(C(=O)NC2CC2)cc1-c1cnn(-c2cncc(NC3CCOCC3)c2)c1] | N-cyclopropyl-4-methyl-3-(1-{5-[(oxan-4-yl)amino]pyridin-3-yl}-1H-pyrazol-4-yl)benzamide |

TABLE 1-continued

The following are representative compounds of the invention which can be made by the general synthetic schemes, the examples, and known methods in the art.

| Example | Structure | Structure Name |
|---|---|---|
| 79 | 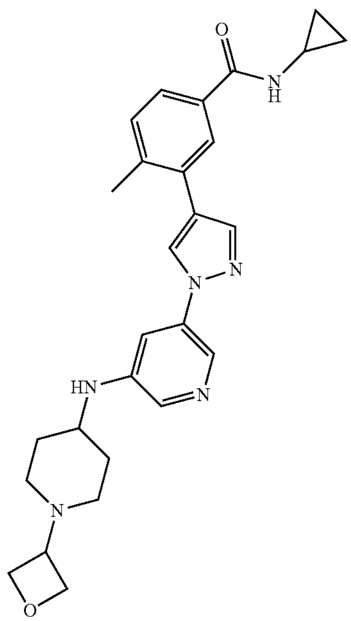 [SMILES: Cc1ccc(C(=O)NC2CC2)cc1-c1cnn(-c2cncc(NC3CCN(C4COC4)CC3)c2)c1] | N-cyclopropyl-4-methyl-3-[1-(5-{[1-(oxetan-3-yl)piperidin-4-yl]amino}pyridin-3-yl)-1H-imidazol-4-yl]benzamide |
| 80 | 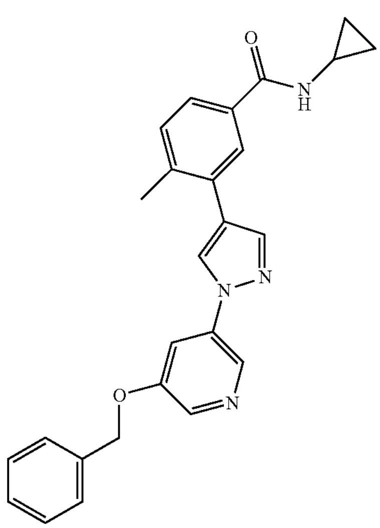 [SMILES: Cc1ccc(C(=O)NC2CC2)cc1-c1cnn(-c2cncc(OCc3ccccc3)c2)c1] | 3-{1-[5-(benzyloxy)pyridin-3-yl]-1H-pyrazol-4-yl}-N-cyclopropyl-4-methylbenzamide |

TABLE 1-continued
The following are representative compounds of the invention which can be made by the general synthetic schemes, the examples, and known methods in the art.
| Example | Structure | Structure Name |
|---|---|---|
| 81 | 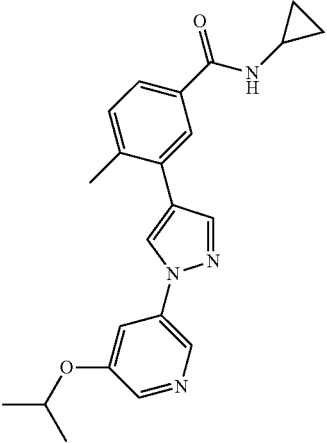 [SMILES: Cc1ccc(C(=O)NC2CC2)cc1-c1cnn(-c2cncc(OC(C)C)c2)c1] | N-cyclopropyl-4-methyl-3-{1-[5-(propan-2-yloxy)pyridin-3-yl]-1H-pyrazol-4-yl}benzamide |
| 92 | 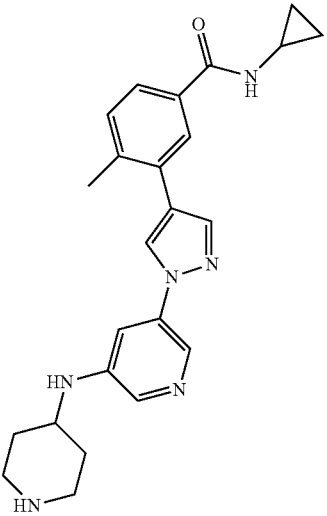 [SMILES: Cc1ccc(C(=O)NC2CC2)cc1-c1cnn(-c2cncc(NC3CCNCC3)c2)c1] | N-cyclopropyl-4-methyl-3-(1-{5-[(piperidin-4-yl)amino]pyridin-3-yl}-1H-pyrazol-4-yl)benzamide |

TABLE 1-continued

The following are representative compounds of the invention which can be made by the general synthetic schemes, the examples, and known methods in the art.

| Example | Structure | Structure Name |
|---------|-----------|----------------|
| 93 | 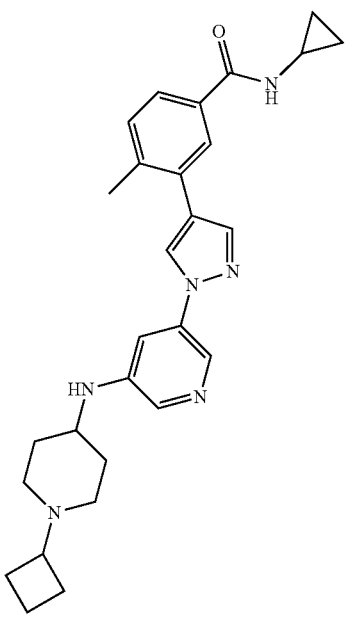 [SMILES: Cc1ccc(C(=O)NC2CC2)cc1-c1cnn(-c2cncc(NC3CCN(C4CCC4)CC3)c2)c1] | 3-(1-{5-[(1-cyclobutylpiperidin-4-yl)amino]pyridin-3-yl}-1H-pyrazol-4-yl)-N-cyclopropyl-4-methyl-benzamide |
| 94 | 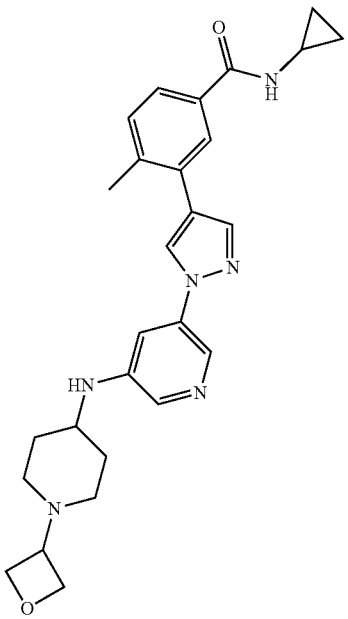 [SMILES: Cc1ccc(C(=O)NC2CC2)cc1-c1cnn(-c2cncc(NC3CCN(C4COC4)CC3)c2)c1] | N-cyclopropyl-4-methyl-3-[1-(5-{[1-(oxetan-3-yl)piperidin-4-yl]amino}pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---|---|---|
| 95 | 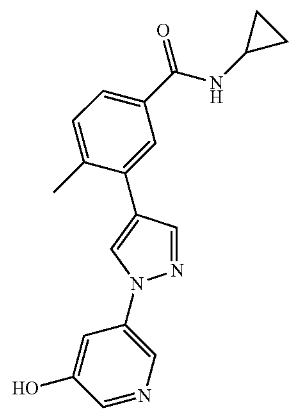 [SMILES: Cc1ccc(C(=O)NC2CC2)cc1-c1cnn(-c2cncc(O)c2)c1] | N-cyclopropyl-3-[1-(5-hydroxypyridin-3-yl)-1H-pyrazol-4-yl]-4-methylbenzamide |
| 96 | 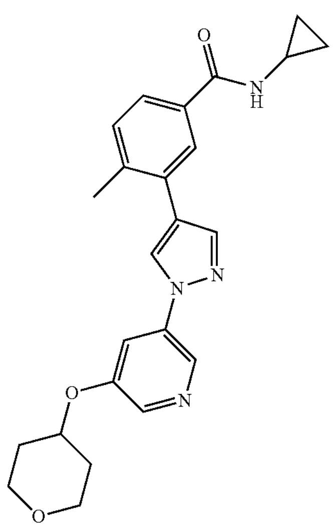 [SMILES: Cc1ccc(C(=O)NC2CC2)cc1-c1cnn(-c2cncc(OC3CCOCC3)c2)c1] | N-cyclopropyl-4-methyl-3-{1-[5-(oxan-4-yloxy)pyridin-3-yl]-1H-pyrazol-4-yl}benzamide |
| 97 | 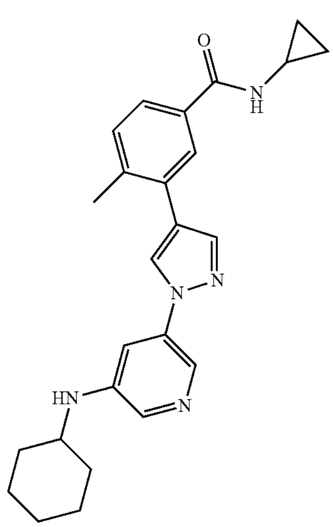 [SMILES: Cc1ccc(C(=O)NC2CC2)cc1-c1cnn(-c2cncc(NC3CCCCC3)c2)c1] | 3-{1-[5-(cyclohexylamino)pyridin-3-yl]-1H-pyrazol-4-yl}-N-cyclopropyl-4-methylbenzamide |

TABLE 1-continued

The following are representative compounds of the invention which can be made by the general synthetic schemes, the examples, and known methods in the art.

| Example | Structure | Structure Name |
|---|---|---|
| 98 | 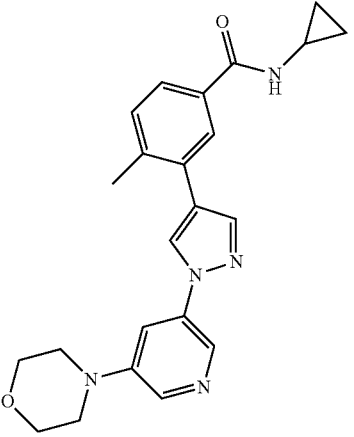 [SMILES: Cc1ccc(C(=O)NC2CC2)cc1-c1cnn(-c2cncc(N3CCOCC3)c2)c1] | N-cyclopropyl-4-methyl-3-{1-[5-(morpholin-4-yl)pyridin-3-yl]-1H-pyrazol-4-yl}benzamide |
| 99 | 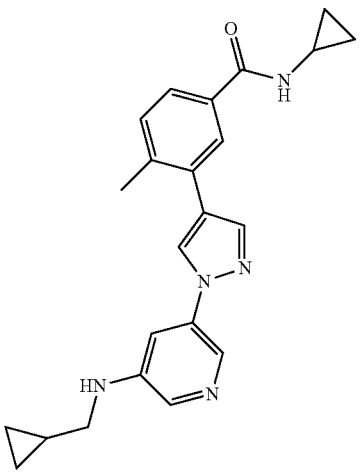 [SMILES: Cc1ccc(C(=O)NC2CC2)cc1-c1cnn(-c2cncc(NCC3CC3)c2)c1] | N-cyclopropyl-3-(1-{5-[(cyclopropylmethyl)amino]pyridin-3-yl}-1H-pyrazol-4-yl)-4-methyl-benzamide |
| 100 | 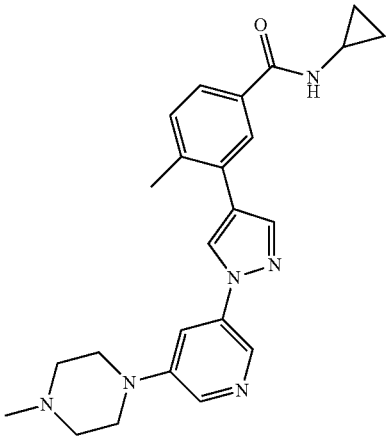 [SMILES: Cc1ccc(C(=O)NC2CC2)cc1-c1cnn(-c2cncc(N3CCN(C)CC3)c2)c1] | N-cyclopropyl-4-methyl-3-{1-[5-(4-methylpiperazin-1-yl)pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
| --- | --- | --- |
| 101 | 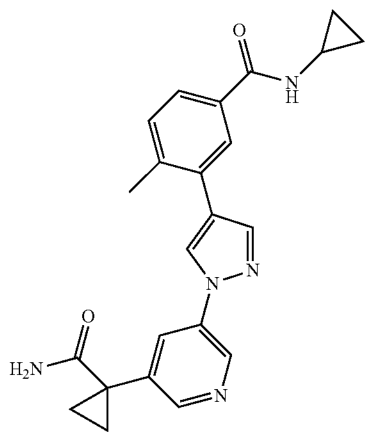 [SMILES: Cc1ccc(C(=O)NC2CC2)cc1-c1cnn(-c2cncc(C3(C(N)=O)CC3)c2)c1] | 3-{1-[5-(1-carbamoylcyclopropyl)pyridin-3-yl]-1H-pyrazol-4-yl}-N-cyclopropyl-4-methylbenzamide |
| 104 | 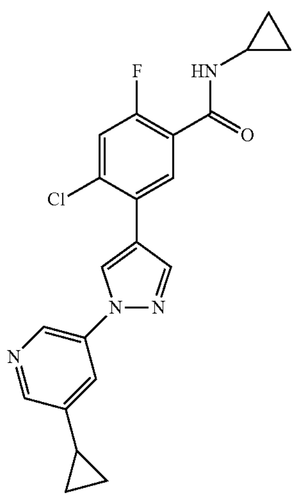 [SMILES: O=C(NC1CC1)c1cc(-c2cnn(-c3cncc(C4CC4)c3)c2)c(Cl)cc1F] | 4-chloro-N-cyclopropyl-5-[1-(5-cyclopropylpyridin-3-yl)-1H-pyrazol-4-yl]-2-fluorobenzamide |
| 105 | 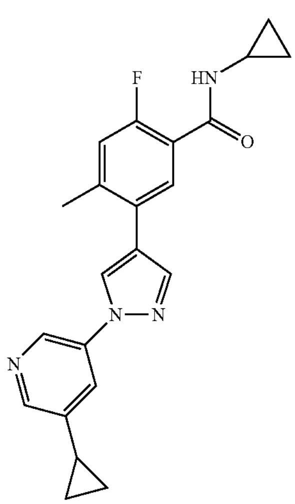 [SMILES: Cc1cc(F)c(C(=O)NC2CC2)cc1-c1cnn(-c2cncc(C3CC3)c2)c1] | N-cyclopropyl-5-[1-(5-cyclopropylpyridin-3-yl)-1H-pyrazol-4-yl]-2-fluoro-4-methylbenzamide |

TABLE 1-continued

The following are representative compounds of the invention which can be made by the general synthetic schemes, the examples, and known methods in the art.

| Example | Structure | Structure Name |
|---|---|---|
| 106 | 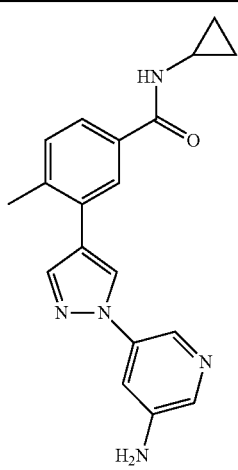 | 3-[1-(5-aminopyridin-3-yl)-1H-pyrazol-4-yl]-N-cyclopropyl-4-methylbenzamide |
| 107 | 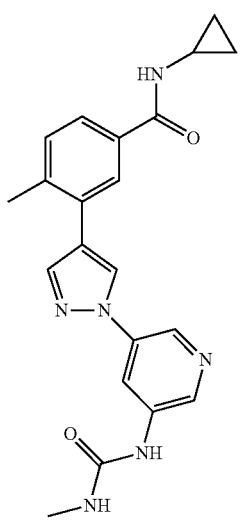 [SMILES: CNC(=O)Nc1cncc(-n2cc(-c3cc(C(=O)NC4CC4)ccc3C)cn2)c1] | N-cyclopropyl-4-methyl-3-(1-{5-[(methylcarbamoyl)amino]pyridin-3-yl}-1H-pyrazol-4-yl)benzamide |
| 108 | 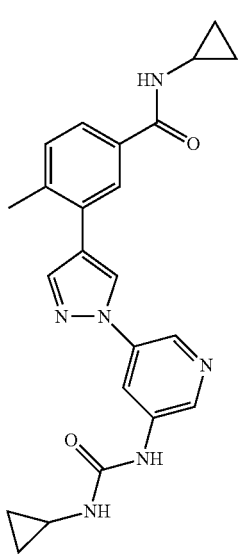 [SMILES: Cc1ccc(C(=O)NC2CC2)cc1-c1cnn(-c2cncc(NC(=O)NC3CC3)c2)c1] | N-cyclopropyl-3-(1-{5-[(cyclopropylcarbamoyl)amino]pyridin-3-yl}-1H-pyrazol-4-yl)-4-methylbenzamide |

TABLE 1-continued

The following are representative compounds of the invention which can be made by the general synthetic schemes, the examples, and known methods in the art.

| Example | Structure | Structure Name |
|---|---|---|
| 109 | 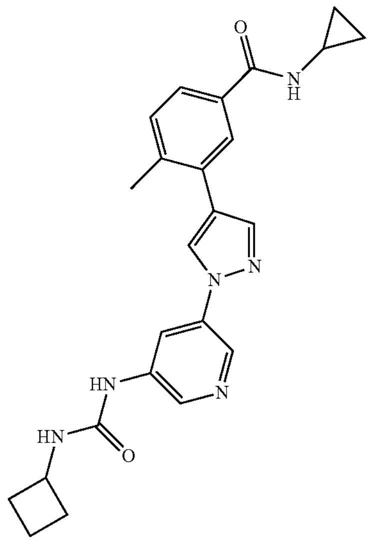 [SMILES: Cc1ccc(C(=O)NC2CC2)cc1-c1cnn(-c2cncc(NC(=O)NC3CCC3)c2)c1] | 3-(1-{5-[(cyclobutylcarbamoyl)amino]pyridin-3-yl}-1H-pyrazol-4-yl)-N-cyclopropyl-4-methylbenzamide |
| 110 | 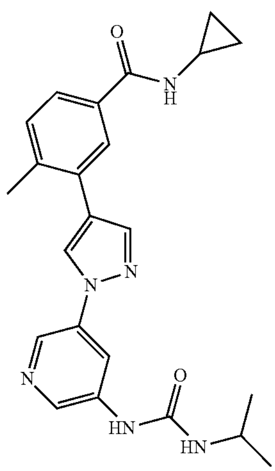 [SMILES: Cc1ccc(C(=O)NC2CC2)cc1-c1cnn(-c2cncc(NC(=O)NC(C)C)c2)c1] | N-cyclopropyl-4-methyl-3-[1-(5-{[(propan-2-yl)carbamoyl]amino}pyridin-3-yl)-1H-pyrazol-4-yl]benzamide |
| 111 | 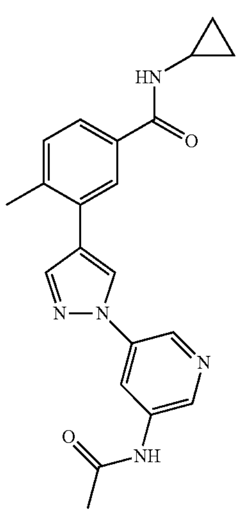 [SMILES: CC(=O)Nc1cncc(-n2cc(-c3cc(C(=O)NC4CC4)ccc3C)cn2)c1] | N-cyclopropyl-3-[1-(5-acetamidopyridin-3-yl)-1H-pyrazol-4-yl]-4-methylbenzamide |

TABLE 1-continued

The following are representative compounds of the invention which can be made by
the general synthetic schemes, the examples, and known methods in the art.

| Example | Structure | Structure Name |
|---|---|---|
| 112 | 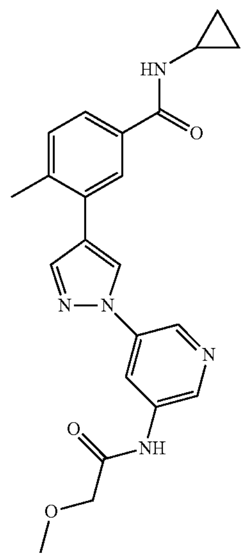 [SMILES: COCC(=O)Nc1cncc(-n2cc(-c3cc(C(=O)NC4CC4)ccc3C)cn2)c1] | N-cyclopropyl-3-{1-[5-(2-methoxyacetamido)pyridin-3-yl]-1H-pyrazol-4-yl}-4-methylbenzamide |
| 113 | 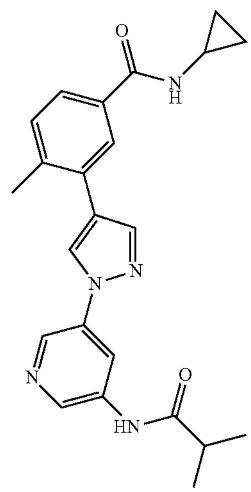 [SMILES: Cc1ccc(C(=O)NC2CC2)cc1-c1cnn(-c2cncc(NC(=O)C(C)C)c2)c1] | N-cyclopropyl-4-methyl-3-{1-[5-(2-methylpropanamido)pyridin-3-yl]-1H-pyrazol-4-yl}benzamide |
| 114 | 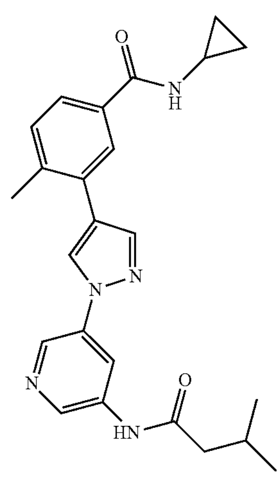 [SMILES: Cc1ccc(C(=O)NC2CC2)cc1-c1cnn(-c2cncc(NC(=O)CC(C)C)c2)c1] | N-cyclopropyl-4-methyl-3-{1-[5-(3-methylbutanamido)pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 115 | 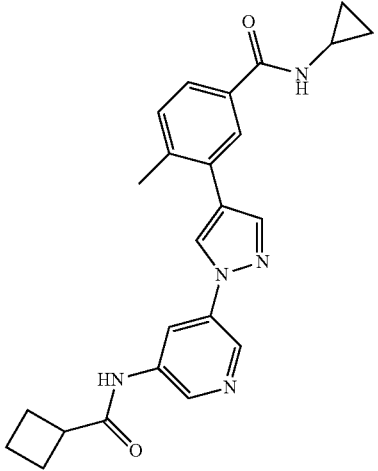 [SMILES: Cc1ccc(C(=O)NC2CC2)cc1-c1cnn(-c2cncc(NC(=O)C3CCC3)c2)c1] | 3-[1-(5-cyclobutaneamidopyridin-3-yl)-1H-pyrazol-4-yl]-N-cyclopropyl-4-methylbenzamide |
| 116 | 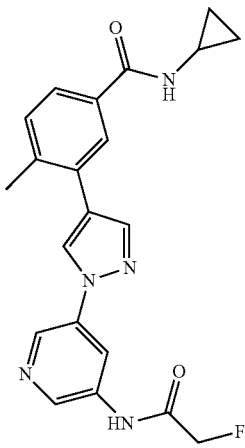 [SMILES: Cc1ccc(C(=O)NC2CC2)cc1-c1cnn(-c2cncc(NC(=O)CF)c2)c1] | N-cyclopropyl-3-{1-[5-(2-fluoroacetamido)pyridin-3-yl]-1H-pyrazol-4-yl}-4-methylbenzamide |
| 117 | 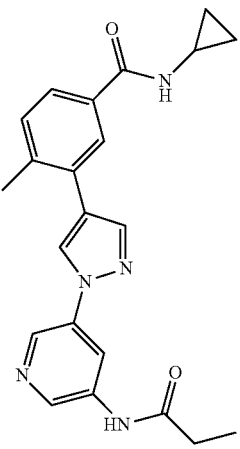 [SMILES: CCC(=O)Nc1cncc(-n2cc(-c3cc(C(=O)NC4CC4)ccc3C)cn2)c1] | N-cyclopropyl-4-methyl-3-[1-(5-propanamidopyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---|---|---|
| 118 | 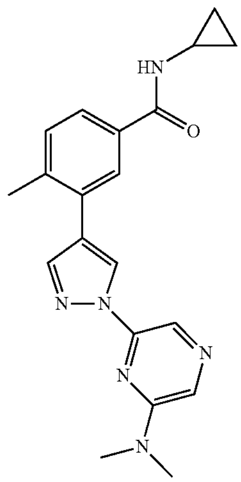 | N-cyclopropyl-3-{1-[6-(dimethylamino)pyrazin-2-yl]-1H-pyrazol-4-yl}-4-methylbenzamide |
| 119 | 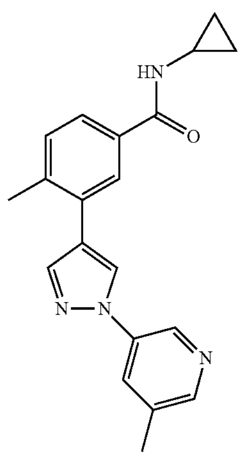 [SMILES: Cc1cncc(-n2cc(-c3cc(C(=O)NC4CC4)ccc3C)cn2)c1] | N-cyclopropyl-4-methyl-3-[1-(5-methylpyridin-3-yl)-1H-pyrazol-4-yl]benzamide |
| 121 | 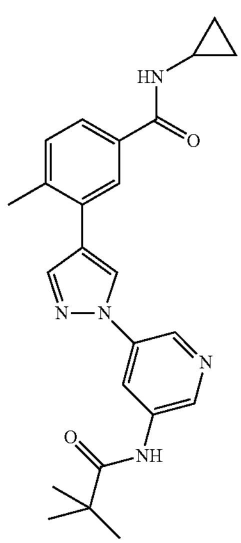 [SMILES: Cc1ccc(C(=O)NC2CC2)cc1-c1cnn(-c2cncc(NC(=O)C(C)(C)C)c2)c1] | N-cyclopropyl-3-{1-[5-(2,2-dimethylpropanamido)pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---|---|---|
| 122 | 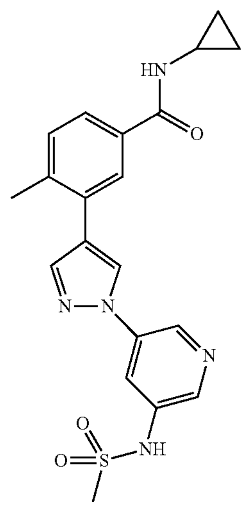 [SMILES: Cc1ccc(C(=O)NC2CC2)cc1-c1cnn(-c2cncc(NS(C)(=O)=O)c2)c1] | N-cyclopropyl-3-[1-(5-methanesulfonamidopyridin-3-yl)-1H-pyrazol-4-yl]-4-methylbenzamide |
| 123 | 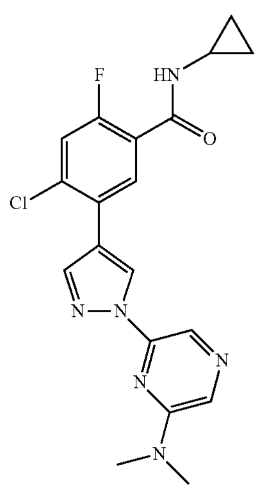 [SMILES: CN(C)c1cncc(-n2cc(-c3cc(C(=O)NC4CC4)c(F)cc3Cl)cn2)n1] | 4-chloro-N-cyclopropyl-5-{1-[6-(dimethylamino)pyrazin-2-yl]-1H-pyrazol-4-yl}-2-fluorobenzamide |
| 124 | 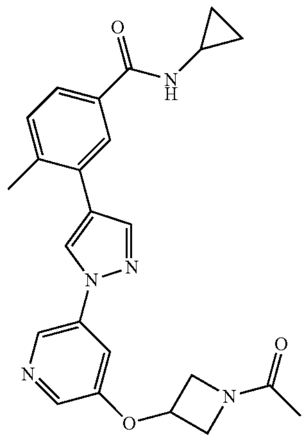 [SMILES: CC(=O)N1CC(Oc2cncc(-n3cc(-c4cc(C(=O)NC5CC5)ccc4C)cn3)c2)C1] | 3-(1-{5-[(1-acetylazetidin-3-yl)oxy]pyridin-3-yl}-1H-pyrazol-4-yl)-N-cyclopropyl-4-methylbenzamide |

TABLE 1-continued

The following are representative compounds of the invention which can be made by the general synthetic schemes, the examples, and known methods in the art.

| Example | Structure | Structure Name |
|---|---|---|
| 125 | 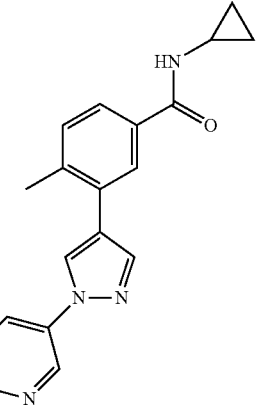 | N-cyclopropyl-4-methyl-3-(1-{5-[(2R)-1-methyl-5-oxopyrrolidin-2-yl]pyridin-3-yl}-1H-pyrazol-4-yl)benzamide |
| 126 | 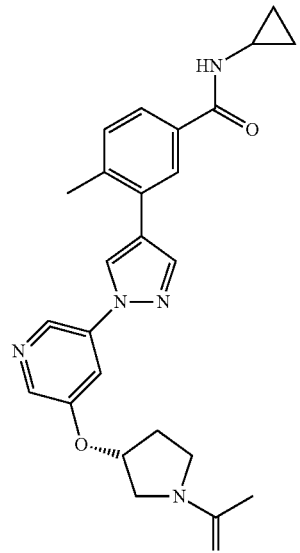 | 3-[1-(5-{[(3R)-1-acetylpyrrolidin-3-yl]oxy}pyridin-3-yl)-1H-pyrazol-4-yl]-N-cyclopropyl-4-methylbenzamide |
| 127 | 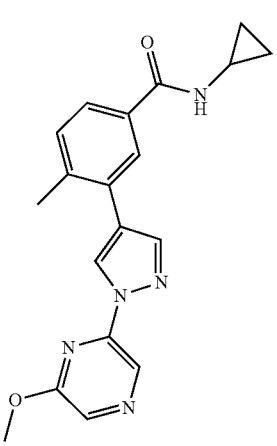 [SMILES: COc1cncc(-n2cc(-c3cc(C(=O)NC4CC4)ccc3C)cn2)n1] | N-cyclopropyl-3-[1-(6-methoxypyrazin-2-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 128 | 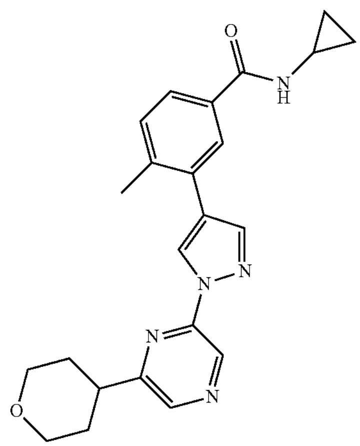 [SMILES: Cc1ccc(C(=O)NC2CC2)cc1-c1cnn(-c2cncc(C3CCOCC3)n2)c1] | N-cyclopropyl-4-methyl-3-{1-[6-(oxan-4-yl)pyrazin-2-yl]-1H-pyrazol-4-yl}benzamide |
| 129 | 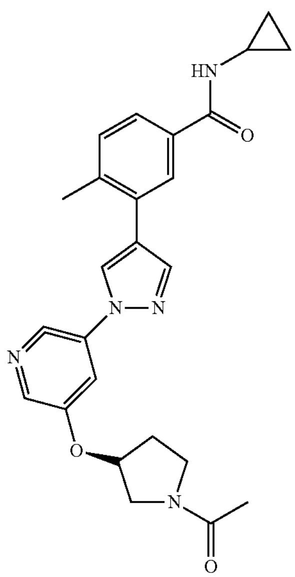 | 3-[1-(5-{[(3S)-1-acetylpyrrolidin-3-yl]oxy}pyridin-3-yl)-1H-pyrazol-4-yl]-N-cyclopropyl-4-methyl-benzamide |
| 131 | 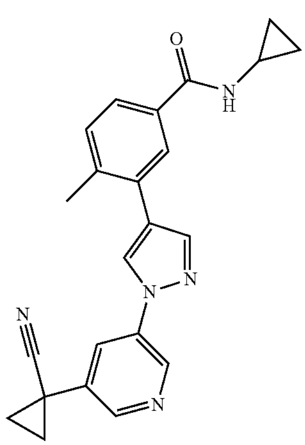 [SMILES: Cc1ccc(C(=O)NC2CC2)cc1-c1cnn(-c2cncc(C3(C#N)CC3)c2)c1] | 3-{1-[5-(1-cyanocyclopropyl)pyridin-3-yl]-1H-pyrazol-4-yl}-N-cyclopropyl-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 135 | 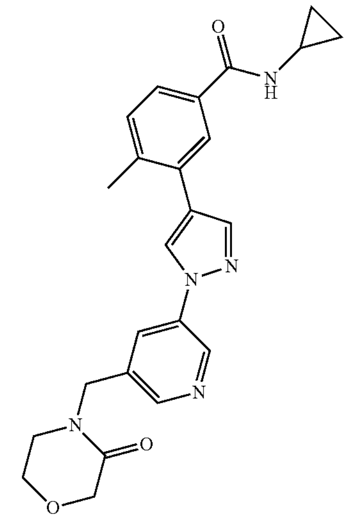 [SMILES: Cc1ccc(C(=O)NC2CC2)cc1-c1cnn(-c2cncc(CN3CCOCC3=O)c2)c1] | N-cyclopropyl-4-methyl-3-(1-{5-[(3-oxomorpholin-4-yl)methyl]pyridin-3-yl}-1H-pyrazol-4-yl)benzamide |
| 136 | 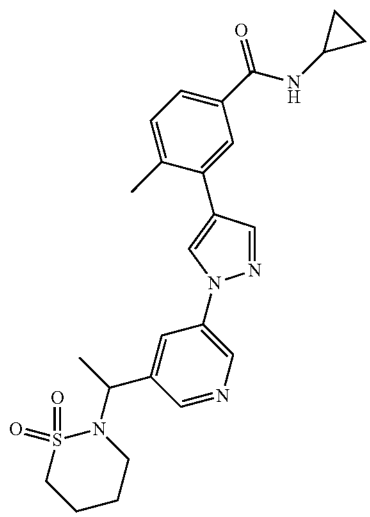 [SMILES: Cc1ccc(C(=O)NC2CC2)cc1-c1cnn(-c2cncc(C(C)N3CCCCS3(=O)=O)c2)c1] | N-cyclopropyl-3-(1-{5-[1-(1,1-dioxo-1$\lambda^6$,2-thiazinan-2-yl)ethyl]pyridin-3-yl}-1H-pyrazol-4-yl)-4-methylbenzamide |
| 137 | 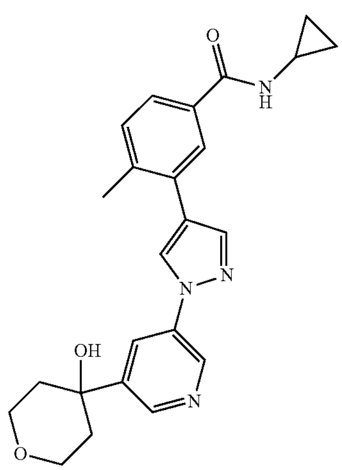 [SMILES: Cc1ccc(C(=O)NC2CC2)cc1-c1cnn(-c2cncc(C3(O)CCOCC3)c2)c1] | N-cyclopropyl-3-{1-[5-(4-hydroxyoxan-4-yl)pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 138 | 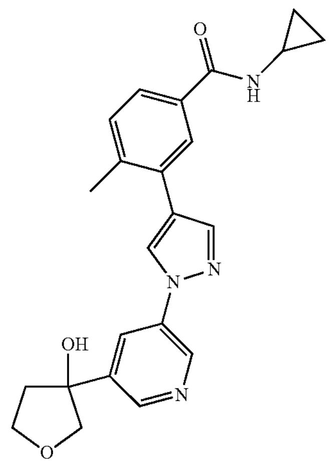 [SMILES: Cc1ccc(C(=O)NC2CC2)cc1-c1cnn(-c2cncc(C3(O)CCOC3)c2)c1] | N-cyclopropyl-3-{1-[5-(3-hydroxy-oxolan-3-yl)pyridin-3-yl]-1H-pyrazol-4-yl}-4-methylbenzamide |
| 140 | 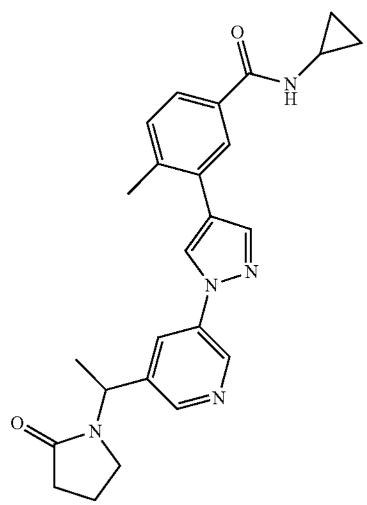 [SMILES: Cc1ccc(C(=O)NC2CC2)cc1-c1cnn(-c2cncc(C(C)N3CCCC3=O)c2)c1] | N-cyclopropyl-4-methyl-3-(1-{5-[1-(2-oxopyrrolidin-1-yl)ethyl]pyridin-3-yl}-1H-pyrazol-4-yl)benzamide |
| 141 | 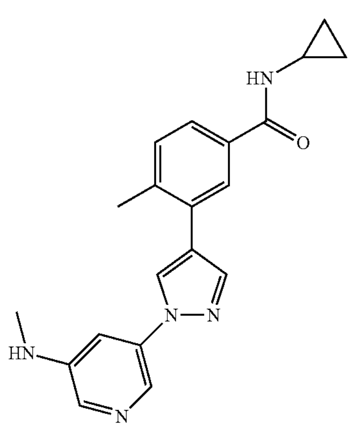 [SMILES: CNc1cncc(-n2cc(-c3cc(C(=O)NC4CC4)ccc3C)cn2)c1] | N-cyclopropyl-4-methyl-3-{1-[5-(methylamino)pyridin-3-yl]-1H-pyrazol-4-yl}benzamide |

TABLE 1-continued

The following are representative compounds of the invention which can be made by the general synthetic schemes, the examples, and known methods in the art.

| Example | Structure | Structure Name |
|---|---|---|
| 142 | 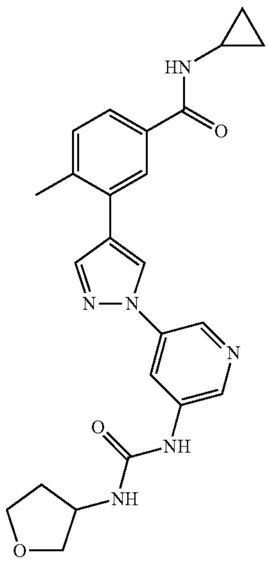 [SMILES: Cc1ccc(C(=O)NC2CC2)cc1-c1cnn(-c2cncc(NC(=O)NC3CCOC3)c2)c1] | N-cyclopropyl-4-methyl-3-[1-(5-{[(oxolan-3-yl)carbamoyl]amino}pyridin-3-yl)-1H-pyrazol-4-yl]benzamide |
| 143 | 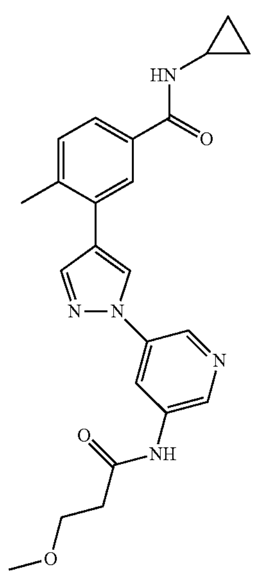 [SMILES: COCCC(=O)Nc1cncc(-n2cc(-c3cc(C(=O)NC4CC4)ccc3C)cn2)c1] | N-cyclopropyl-3-{1-[5-(3-methoxypropanamido)pyridin-3-yl]-1H-pyrazol-4-yl}-4-methylbenzamide |

TABLE 1-continued

The following are representative compounds of the invention which can be made by the general synthetic schemes, the examples, and known methods in the art.

| Example | Structure Name |
|---------|----------------|
| 144 | 3-[1-(5-cyclopropaneamidopyridin-3-yl)-1H-pyrazol-4-yl]-N-cyclopropyl-4-methylbenzamide |
| 145 | N-cyclopropyl-4-methyl-3-{1-[5-(oxolan-3-yloxy)pyridin-3-yl]-1H-pyrazol-4-yl}benzamide |
| 146 | N-cyclopropyl-3-{1-[5-(cyclopropylmethoxy)pyridin-3-yl]-1H-pyrazol-4-yl}-4-methylbenzamide |

TABLE 1-continued
The following are representative compounds of the invention which can be made by the general synthetic schemes, the examples, and known methods in the art.
| Example | Structure | Structure Name |
|---|---|---|
| 147 | 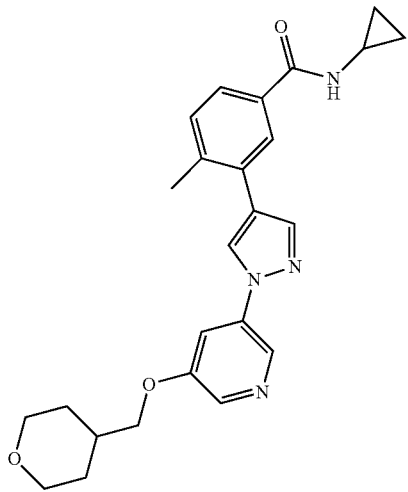 [SMILES: Cc1ccc(C(=O)NC2CC2)cc1-c1cnn(-c2cncc(OCC3CCOCC3)c2)c1] | N-cyclopropyl-4-methyl-3-{1-[5-(oxan-4-ylmethoxy)pyridin-3-yl]-1H-pyrazol-4-yl}benzamide |
| 148 | 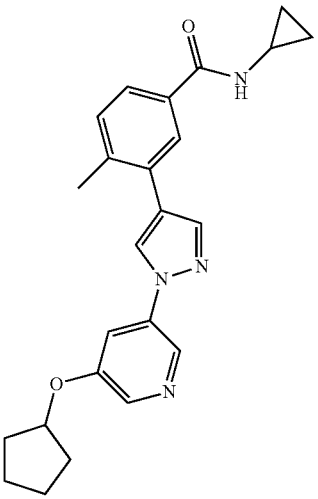 [SMILES: Cc1ccc(C(=O)NC2CC2)cc1-c1cnn(-c2cncc(OC3CCCC3)c2)c1] | 3-{1-[5-(cyclopentyloxy)pyridin-3-yl]-1H-pyrazol-4-yl}-N-cyclopropyl-4-methylbenzamide |

TABLE 1-continued

The following are representative compounds of the invention which can be made by the general synthetic schemes, the examples, and known methods in the art.

| Example | Structure | Structure Name |
| --- | --- | --- |
| 149 | 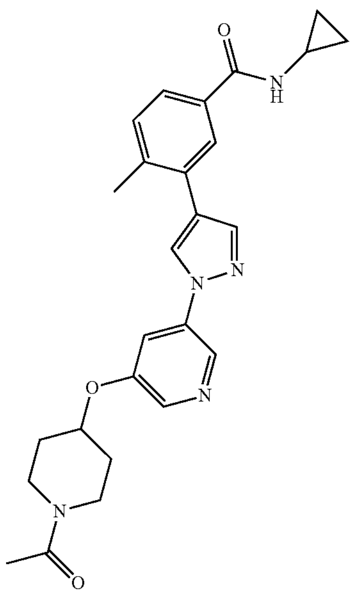 [SMILES: CC(=O)N1CCC(Oc2cncc(-n3cc(-c4cc(C(=O)NC5CC5)ccc4C)cn3)c2)CC1] | 3-(1-{5-[(1-acelylpiperidin-4-yl)oxy]pyridin-3-yl}-1H-pyrazol-4-yl)-N-cyclopropyl-4-methyl-benzamide |
| 150 | 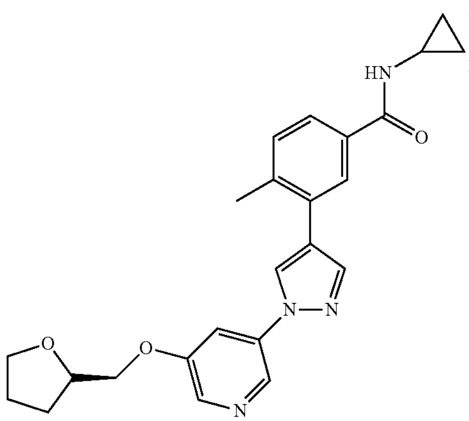 | N-cyclopropyl-4-methyl-3-(1-{5-[(2R)-oxolan-2-ylmethoxy]pyridin-3-yl}-1H-pyrazol-4-yl)benzamide |
| 151 | 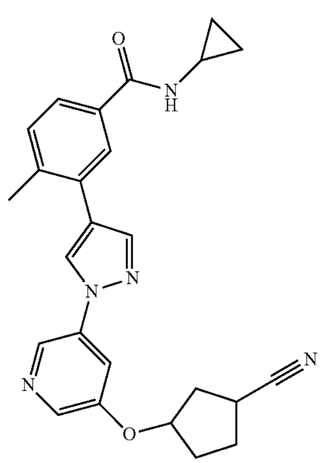 [SMILES: Cc1ccc(C(=O)NC2CC2)cc1-c1cnn(-c2cncc(OC3CCC(C#N)C3)c2)c1] | 3-(1-{5-[(3-cyanocyclopentyl)oxy]pyridin-3-yl}-1H-pyrazol-4-yl)-N-cyclopropyl-4-methylbenzamide |

TABLE 1-continued

The following are representative compounds of the invention which can be made by the general synthetic schemes, the examples, and known methods in the art.

| Example | Structure | Structure Name |
|---------|-----------|----------------|
| 152 | 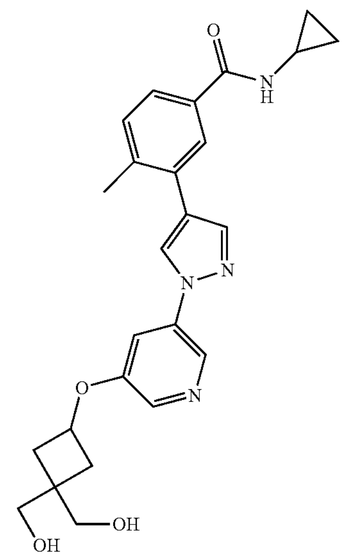 [SMILES: Cc1ccc(C(=O)NC2CC2)cc1-c1cnn(-c2cncc(OC3CC(CO)(CO)C3)c2)c1] | 3-(1-{5-[3,3-bis(hydroxymethyl)cyclobutoxy]pyridin-3-yl}-1H-pyrazol-4-yl)-N-cyclopropyl-4-methylbenzamide |
| 153 | 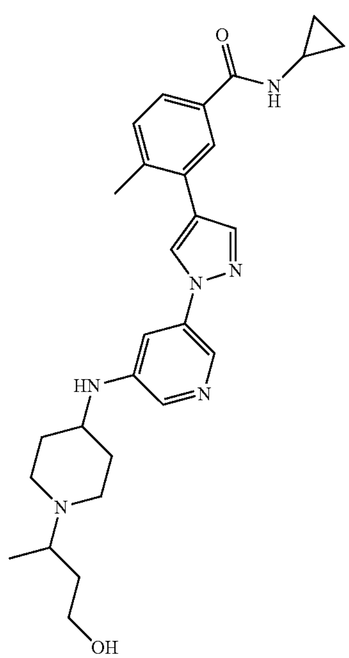 [SMILES: Cc1ccc(C(=O)NC2CC2)cc1-c1cnn(-c2cncc(NC3CCN(C(C)CCO)CC3)c2)c1] | N-cyclopropyl-3-[1-(5-{[1-(4-hydroxybutan-2-yl)piperidin-4-yl]amino}pyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 154 | 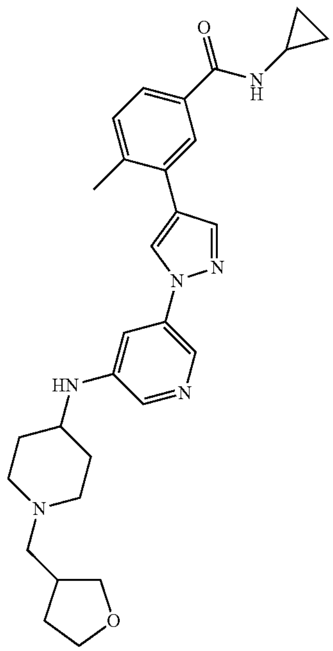 [SMILES: Cc1ccc(C(=O)NC2CC2)cc1-c1cnn(-c2cncc(NC3CCN(CC4CCOC4)CC3)c2)c1] | N-cyclopropyl-4-methyl-3-[1-(5-{[1-(oxolan-3-ylmethyl)piperidin-4-yl]amino}pyridin-3-yl)-1H-pyrazol-4-yl]benzamide |
| 155 | 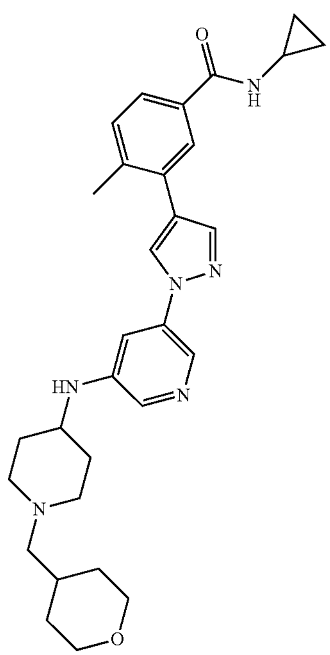 [SMILES: Cc1ccc(C(=O)NC2CC2)cc1-c1cnn(-c2cncc(NC3CCN(CC4CCOCC4)CC3)c2)c1] | N-cyclopropyl-4-methyl-3-[1-(5-{[1-(oxan-4-ylmethyl)piperidin-4-yl]amino}pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---|---|---|
| 156 | 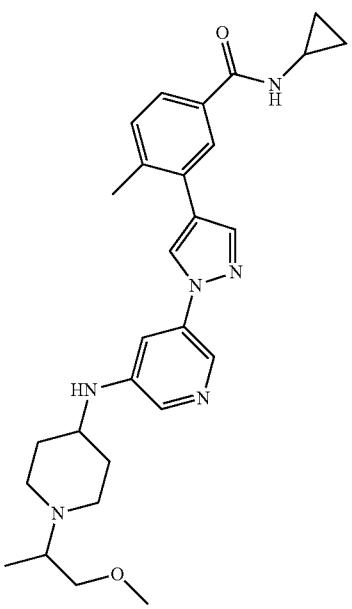 [SMILES: COCC(C)N1CCC(Nc2cncc(-n3cc(-c4cc(C(=O)NC5CC5)ccc4C)cn3)c2)CC1] | N-cyclopropyl-3-[1-(5-{[1-(1-methoxypropan-2-yl)piperidin-4-yl]amino}pyridin-3-yl)-1H-pyrazol-4-yl]-4-methylbenzamide |
| 157 | 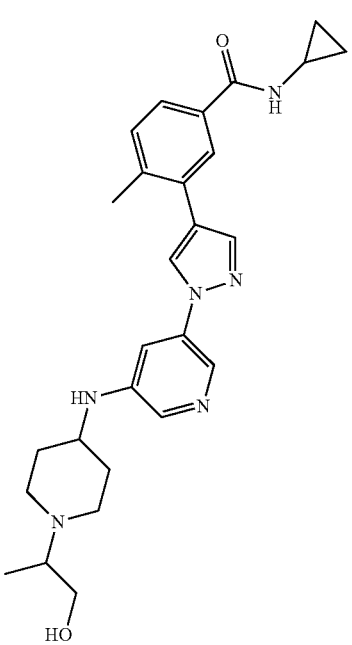 [SMILES: Cc1ccc(C(=O)NC2CC2)cc1-c1cnn(-c2cncc(NC3CCN(C(C)CO)CC3)c2)c1] | N-cyclopropyl-3-[1-(5-{[1-(1-hydroxypropan-2-yl)piperidin-4-yl]amino}pyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 158 | 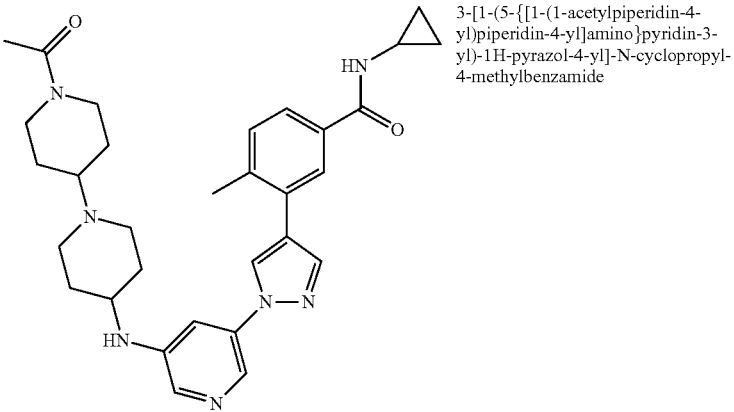 | 3-[1-(5-{[1-(1-acetylpiperidin-4-yl)piperidin-4-yl]amino}pyridin-3-yl)-1H-pyrazol-4-yl]-N-cyclopropyl-4-methylbenzamide |
| 159 | 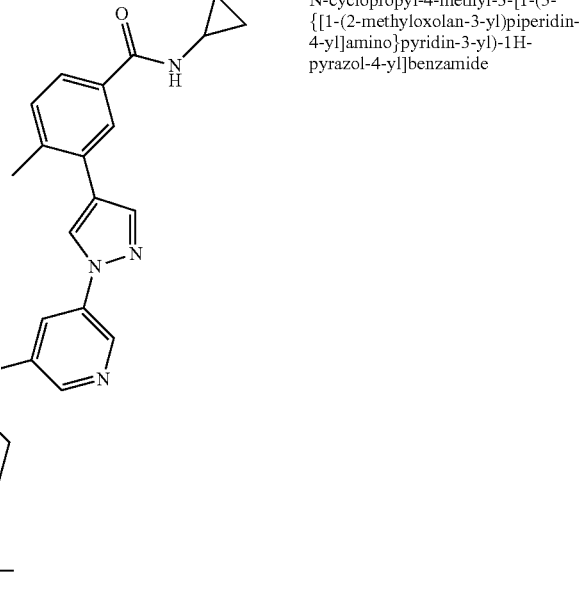 | N-cyclopropyl-4-methyl-3-[1-(5-{[1-(2-methyloxolan-3-yl)piperidin-4-yl]amino}pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---|---|---|
| 160 | 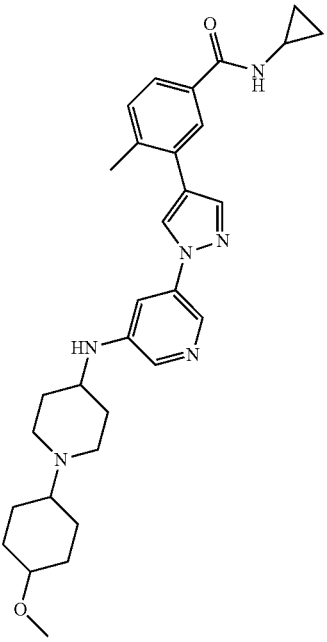 [SMILES: COC1CCC(N2CCC(Nc3cncc(-n4cc(-c5cc(C(=O)NC6CC6)ccc5C)cn4)c3)CC2)CC1] | N-cyclopropyl-3-[1-(5-{[1-(4-methoxycyclohexyl)piperidin-4-yl]amino}pyridin-3-yl)-1H-pyrazol-4-yl]-4-methylbenzamide |
| 161 | 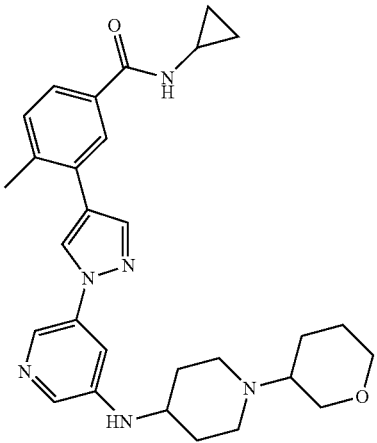 [SMILES: Cc1ccc(C(=O)NC2CC2)cc1-c1cnn(-c2cncc(NC3CCN(C4CCCOC4)CC3)c2)c1] | N-cyclopropyl-4-methyl-3-[1-(5-{[1-(oxan-3-yl)piperidin-4-yl]amino}pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
| --- | --- | --- |
| 162 | 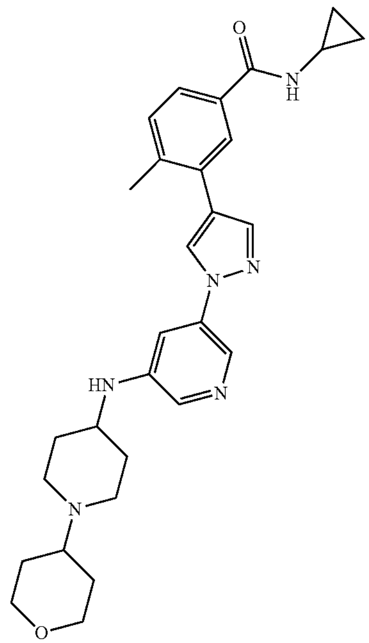 [SMILES: Cc1ccc(C(=O)NC2CC2)cc1-c1cnn(-c2cncc(NC3CCN(C4CCOCC4)CC3)c2)c1] | N-cyclopropyl-4-methyl-3-[1-(5-{[1-(oxan-4-yl)piperidin-4-yl]amino}pyridin-3-yl)-1H-pyrazol-4-yl]benzamide |
| 163 | 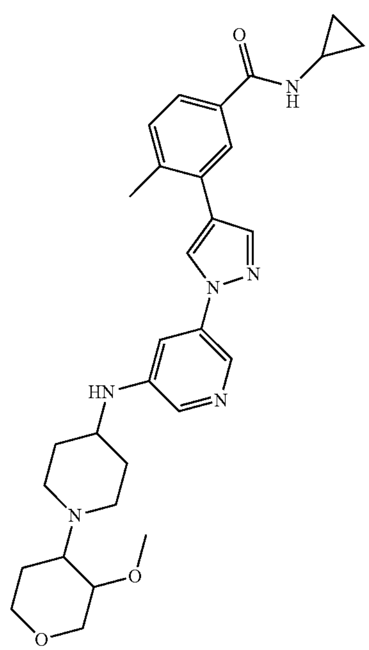 [SMILES: COC1COCCC1N1CCC(Nc2cncc(-n3cc(-c4cc(C(=O)NC5CC5)ccc4C)cn3)c2)CC1] | N-cyclopropyl-3-[1-(5-{[1-(3-methoxyoxan-4-yl)piperidin-4-yl]amino}pyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 164 | 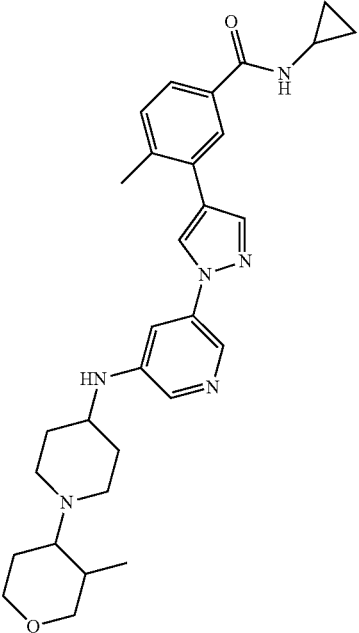 [SMILES: Cc1ccc(C(=O)NC2CC2)cc1-c1cnn(-c2cncc(NC3CCN(C4CCOCC4C)CC3)c2)c1] | N-cyclopropyl-4-methyl-3-[1-(5-{[1-(3-methyloxan-4-yl)piperidin-4-yl]amino}pyridin-3-yl)-1H-pyrazol-4-yl]benzamide |
| 165 | 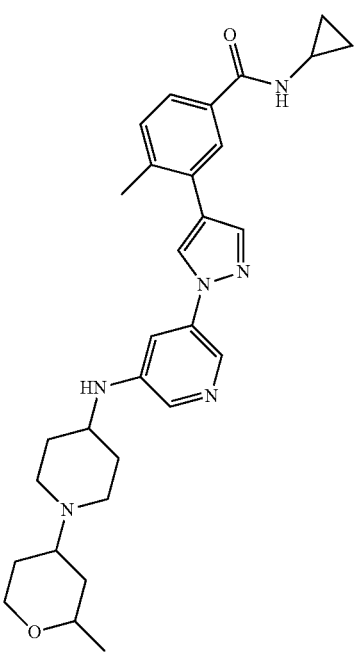 [SMILES: Cc1ccc(C(=O)NC2CC2)cc1-c1cnn(-c2cncc(NC3CCN(C4CCOC(C)C4)CC3)c2)c1] | N-cyclopropyl-4-methyl-3-[1-(5-{[1-(2-methyloxan-4-yl)piperidin-4-yl]amino}pyridin-3-yl)-1H-pyrazol-4-yl]benzamide |

TABLE 1-continued

The following are representative compounds of the invention which can be made by the general synthetic schemes, the examples, and known methods in the art.

| Example | Structure | Structure Name |
|---|---|---|
| 166 | 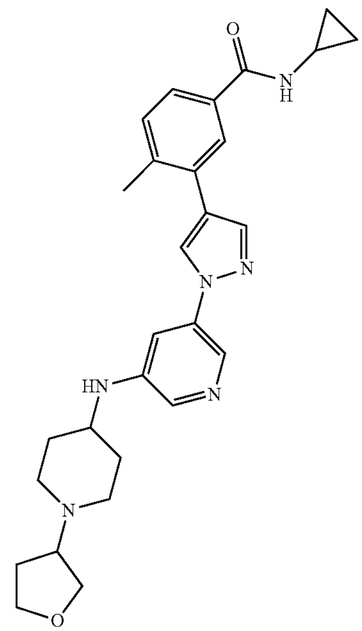 [SMILES: Cc1ccc(C(=O)NC2CC2)cc1-c1cnn(-c2cncc(NC3CCN(C4CCOC4)CC3)c2)c1] | N-cyclopropyl-4-methyl-3-[1-(5-{[1-(oxolan-3-yl)piperidin-4-yl]amino}pyridin-3-yl)-1H-pyrazol-4-yl]benzamide |
| 167 | 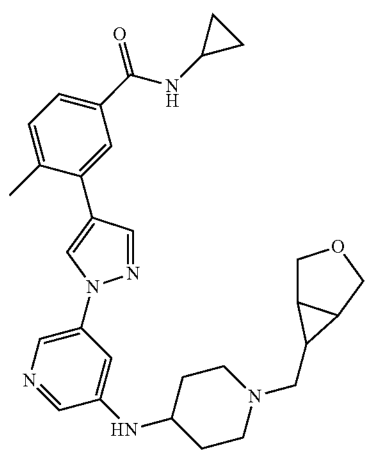 [SMILES: Cc1ccc(C(=O)NC2CC2)cc1-c1cnn(-c2cncc(NC3CCN(CC4C5COCC54)CC3)c2)c1] | N-cyclopropyl-4-methyl-3-(1-{5-[(1-{3-oxabicyclo[3.1.0]hexan-6-ylmethyl}piperidin-4-yl)amino]pyridin-3-yl}-1H-pyrazol-4-yl)benzamide |
| 168 | 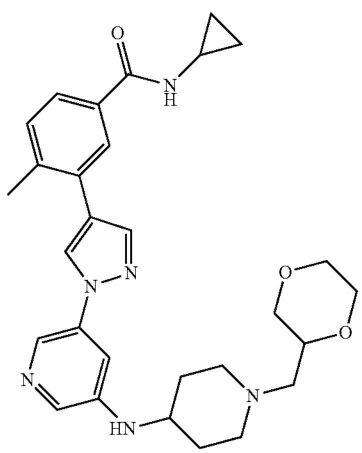 [SMILES: Cc1ccc(C(=O)NC2CC2)cc1-c1cnn(-c2cncc(NC3CCN(CC4COCCO4)CC3)c2)c1] | N-cyclopropyl-3-[1-(5-{[1-(1,4-dioxan-2-ylmethyl)piperidin-4-yl]amino}pyridin-3-yl)-1H-pyrazol-4-yl]-4-methylbenzamide |

TABLE 1-continued

The following are representative compounds of the invention which can be made by the general synthetic schemes, the examples, and known methods in the art.

| Example | Structure | Structure Name |
|---|---|---|
| 169 | 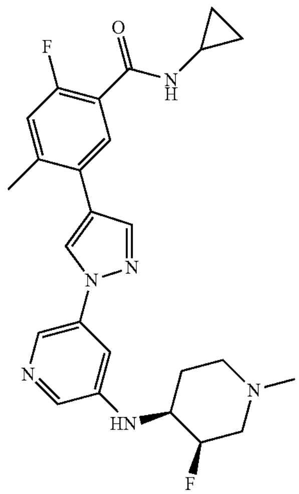 | N-Cyclopropyl-2-fluoro-5-[1(5-{(3R,4S)-3-fluoro-1-methyl-piperidin-4-yl]amino}pyridine-3-yl)-1H-pyrazol-4-yl]-4-methyl-benzamide |
| 170 | 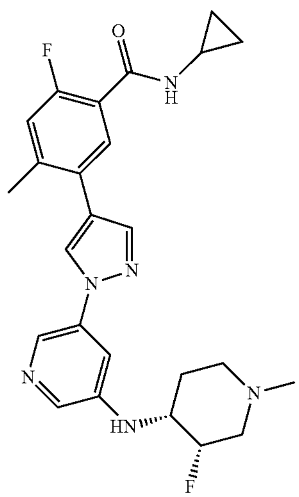 | N-Cyclopropyl-2-fluoro-5-[1(5-{(3S,4R)-3-fluoro-1-methylpiperidin-4-yl]amino}pyridine-3-yl)-1H-pyrazol-4-yl]-4-methylbenzamide |
| 171 | 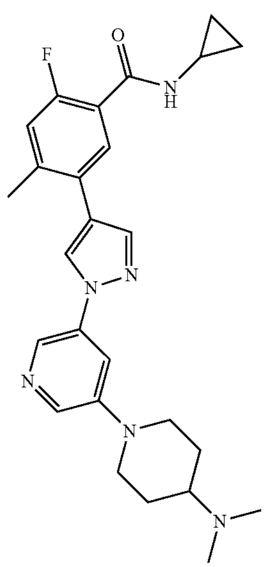 | N-Cyclopropyl-5-[1-(4-dimethyl-amino-3,4,5,6-tetrahydro-2H-[1,3"]bipyridinyl-5"-yl)-1H-pyrazol-4-yl]-2-fluoro-4-methyl-benzamide |

TABLE 1-continued

The following are representative compounds of the invention which can be made by the general synthetic schemes, the examples, and known methods in the art.

| Example | Structure | Structure Name |
| --- | --- | --- |
| 172 | 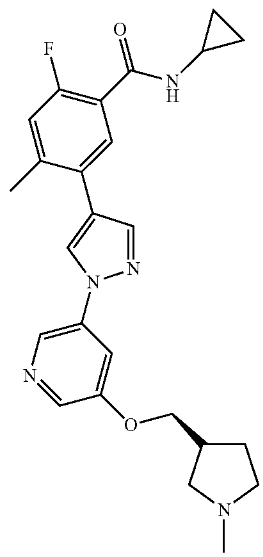 | N-Cyclopropyl-2-fluoro-4-methyl-5-{1-[5-((S)-1-methyl-pyrrolidin-3-ylmethoxy)-pyridin-3-yl]-1H-pyrazol-4-yl}-benzamide |
| 173 | 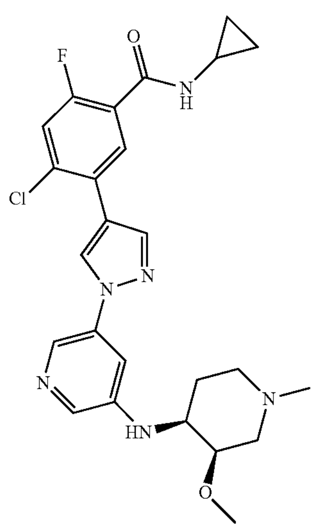 [SMILES: CO[C@@H]1CN(C)CC[C@@H]1Nc1cncc(-n2cc(-c3cc(C(=O)NC4CC4)c(F)cc3Cl)cn2)c1] | 4-Chloro-N-cyclopropyl-2-fluoro-5-{1-[5-((3R,4S)-3-methoxy-1-methyl-piperidin-4-ylamino)-pyridin-3-yl]-1H-pyrazol-4-yl}-benzamide |
| 174 | 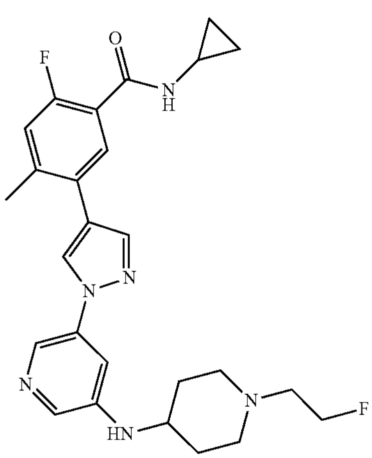 [SMILES: Cc1cc(F)c(C(=O)NC2CC2)cc1-c1cnn(-c2cncc(NC3CCN(CCF)CC3)c2)c1] | N-Cyclopropyl-2-fluoro-5-(1-{5-[1-(2-fluoro-ethyl)-piperidin-4-ylamino]-pyridin-3-yl}-1H-pyrazol-4-yl)-4-methyl-benzamide |

TABLE 1-continued

The following are representative compounds of the invention which can be made by the general synthetic schemes, the examples, and known methods in the art.

| Example | Structure | Structure Name |
|---|---|---|
| 175 | 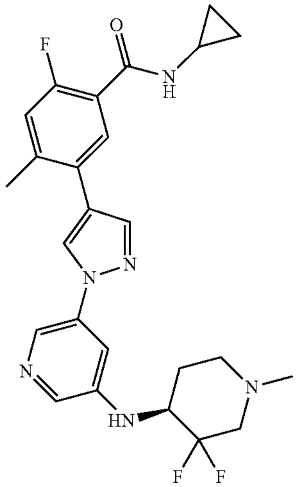 | N-Cyclopropyl-5-{1-[5-((S)-3,3-difluoro-1-methyl-piperidin-4-ylamino)-pyridin-3-yl]-1H-pyrazol-4-yl}-2-fluoro-4-methyl-benzamide |
| 176 | | N-Cyclopropyl-5-{1-[5-((R)-3,3-difluoro-1-methyl-piperidin-4-ylamino)-pyridin-3-yl]-1H-pyrazol-4-yl}-2-fluoro-4-methyl-benzamide | or the pharmaceutically acceptable salts thereof.

In one embodiment, the invention relates to any of the compounds depicted in Table 1 above and the pharmaceutically acceptable salts thereof.

For all compounds disclosed hereinabove in this application, in the event the nomenclature is in conflict with the structure, it shall be understood that the compound is defined by the structure. For compounds with stereogenic centers, the structures show the absolute stereochemistry.

The invention also relates to pharmaceutical preparations, containing as active substance one or more compounds of the invention, or the pharmaceutically acceptable derivatives thereof, optionally combined with conventional excipients and/or carriers.

BRIEF DESCRIPTION OF THE FIGURES

FIG. 2: ORTEP plot of (3R,4S)-3-Fluoro-1-methyl-piperidin-4-yl)-(5-pyrazol-1-yl-pyridin-3-yl)-amine (I-29)

Figure 1:
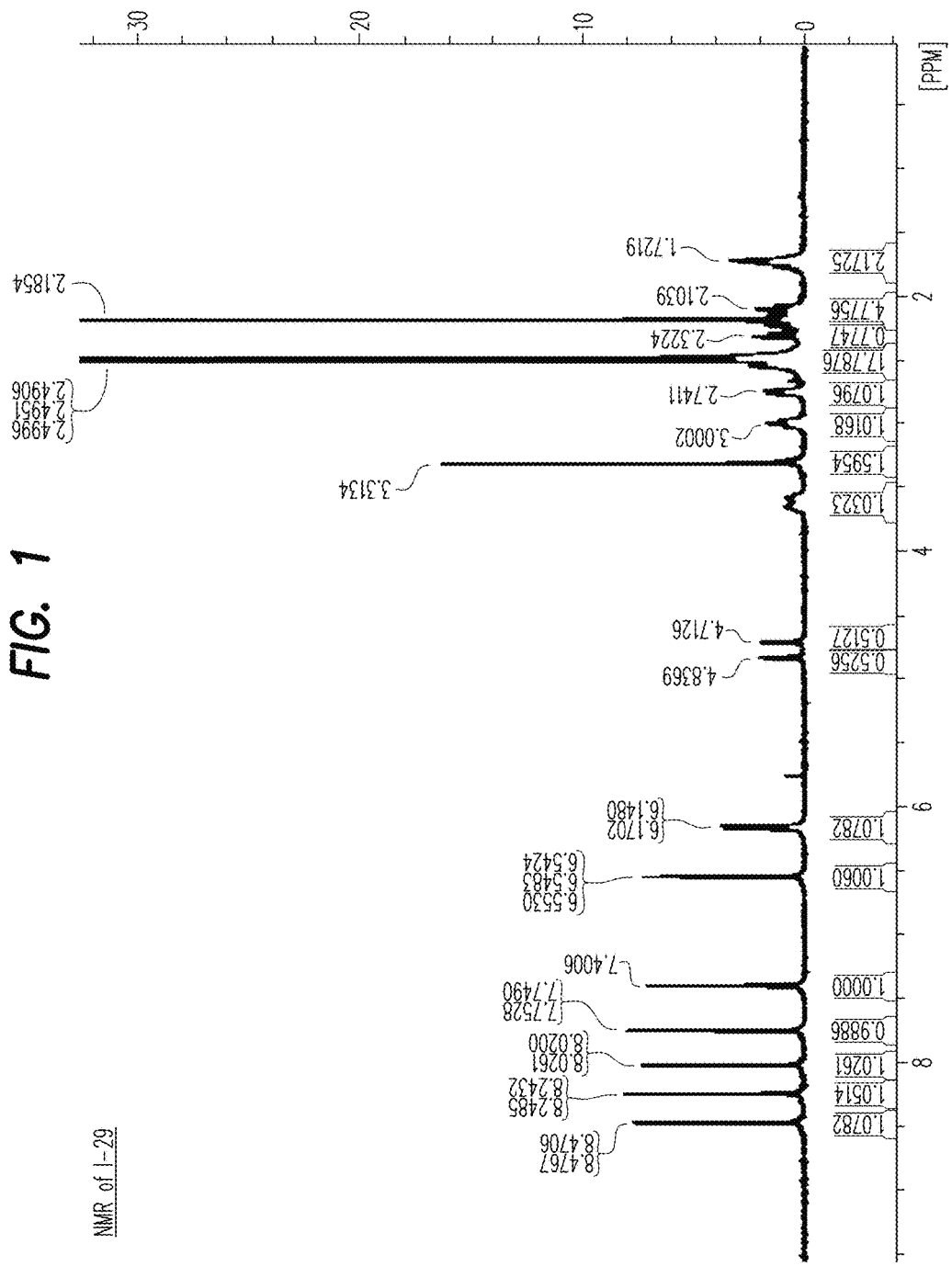
FIG. 1: $^1$H NMR (DMSO, 400 mHz Bruker) of (3R,4S)-3-Fluoro-1-methyl-piperidin-4-yl)-(5-pyrazol-1-yl-pyridin-3-yl)-amine (I-29)
Figure 3:
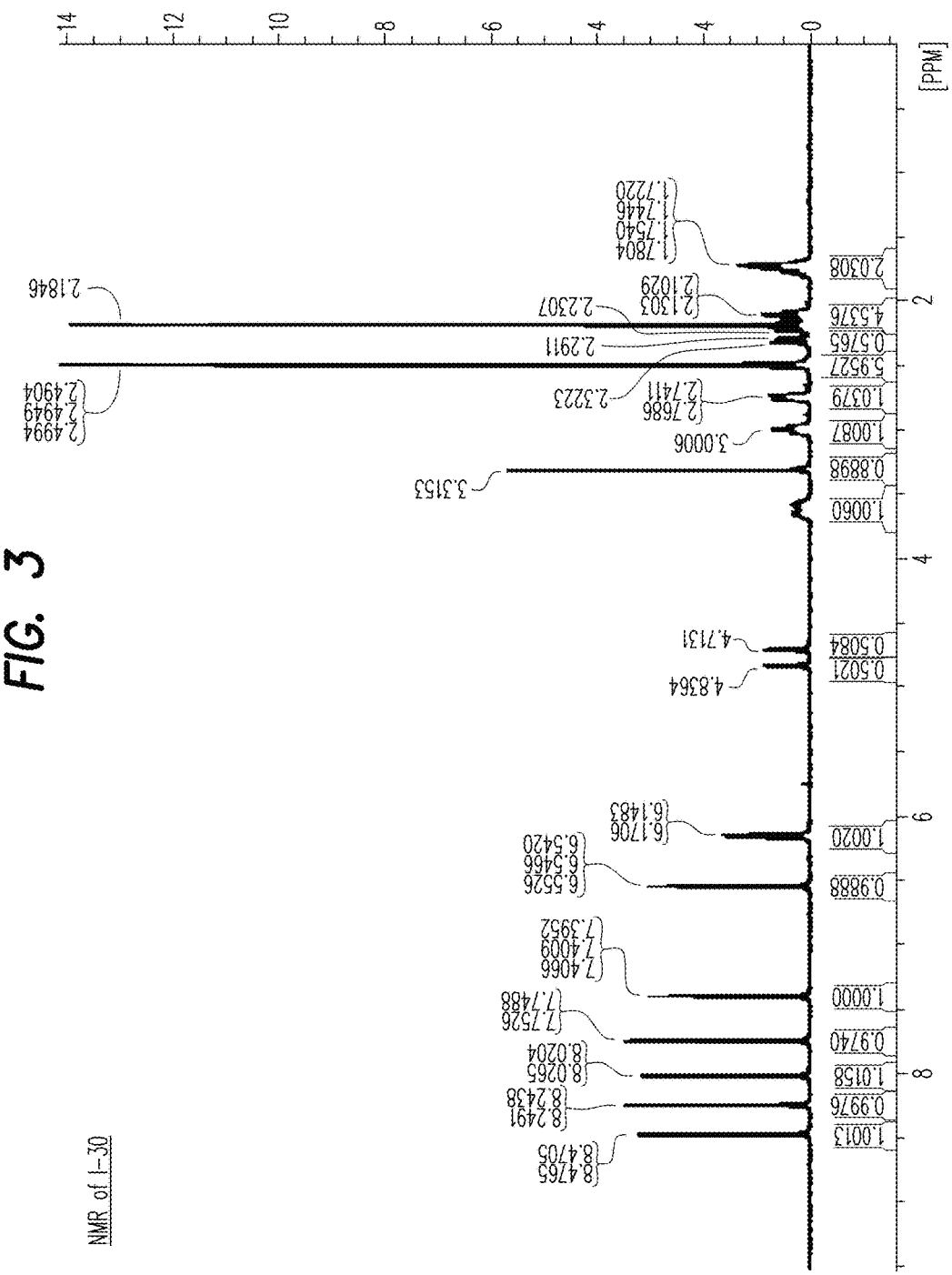
FIG. 3: $^1$H NMR (DMSO, 400 mHz Bruker) of (3S,4R)-3-Fluoro-1-methyl-piperidin-4-yl)-(5-pyrazol-1-yl-pyridin-3-yl)-amine (I-30)
Figure 4:
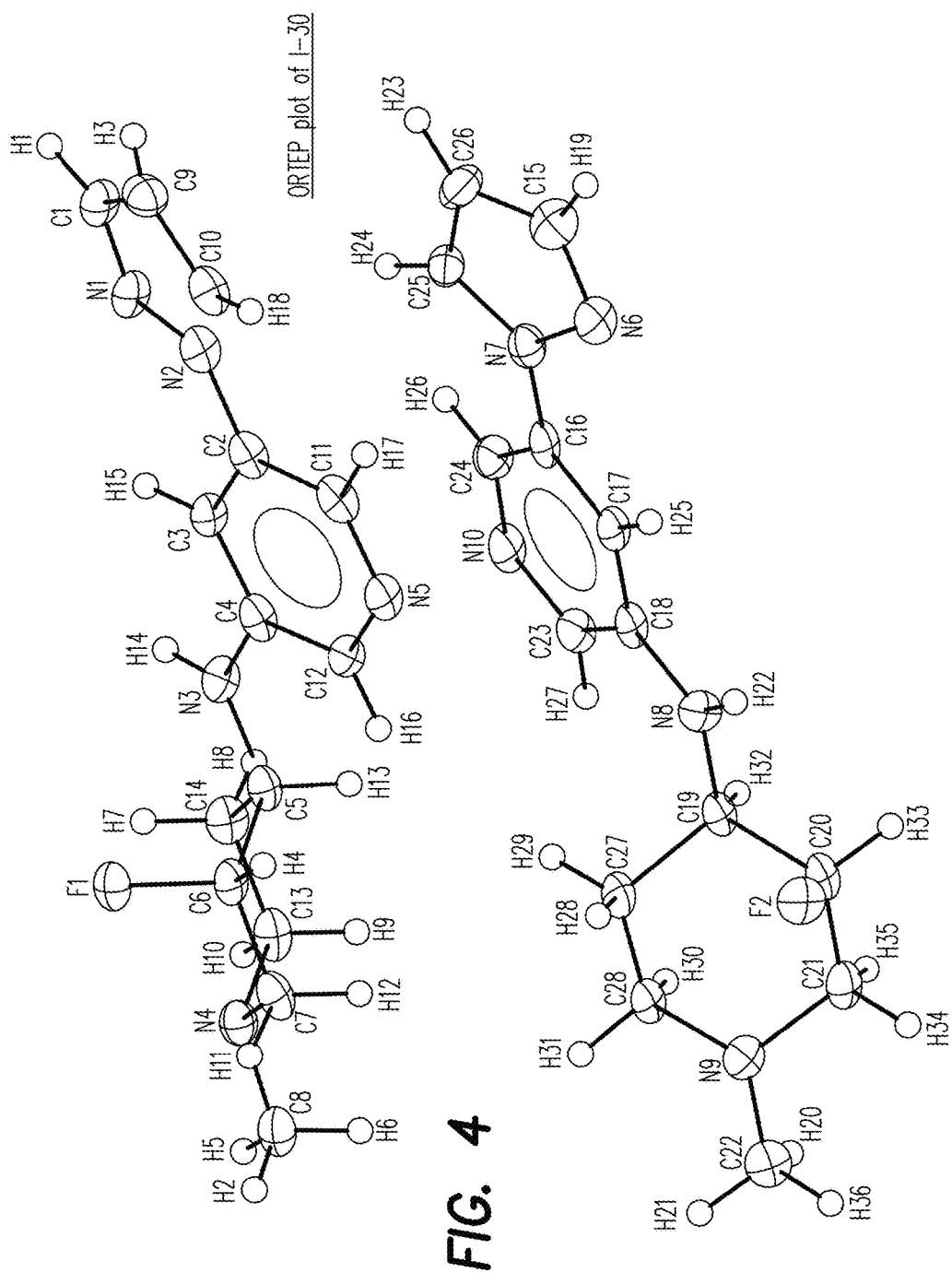
FIG. 4: ORTEP plot of (3S,4R)-3-Fluoro-1-methyl-piperidin-4-yl)-(5-pyrazol-1-yl-pyridin-3-yl)-amine (I-30)

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

It shall be understood that if N is not substituted then it is NH. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" or "$C_{3-10}$ cycloalkyl" refers to a nonaromatic 3 to 10-membered (but preferably, 3 to 6-membered) monocyclic carbocyclic/cycloalkyl radical or a nonaromatic 6 to 10-membered fused bicyclic, bridged bicyclic, or spirocyclic carbocyclic radical. The $C_{3-10}$ carbocycle/cycloalkyl ring may be either saturated or partially unsaturated, and the carbocycle/cycloalkyl ring may be attached by any atom of the cycle which results in the creation of a stable structure. Non-limiting examples of 3 to 10-membered monocyclic carbocycles/cycloalkyl rings include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic/cycloalkyl radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo [2.2.2]heptanyl, bicyclo [2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "aryl" refers to aromatic hydrocarbon rings containing from six to ten carbon ring atoms. The term aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl, benzothiazolyl, dihydroindolyl, azaindolyl, benzothiazolyl, benzpyrrolyl, benzpyrazolyl, pyridopyrazolyl, dihydrobenzofuranyl, benzothienyl, benzodioxanyl, dihydrobenzo[1,4]dioxanyl and benzo[1,3]dioxolyl.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, aryl, cycloalkyl/carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and $N-(C_1-C_4 \text{ alkyl})_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

SYNTHETIC EXAMPLES

| List of abbreviations | |
|---|---|
| Ac | acetyl |
| ACN | acetonitrile |
| aq. | aquatic, aqueous |
| Boc | tert-butyloxycarbonyl |
| Boc₂O | di-tert-butyl dicarbonate |
| Bu | butyl |
| dba | Dibenzylideneacetone |
| Davephos | 2-dimethylamino-2'-dicyclohexylaminophosphinobiphenyl |
| DBA | dibenzylideneacetone |
| DCM | dichloromethane |
| DIPEA | N,N-diisopropylethylamine |
| DMAP | 4-N,N-dimethylaminopyridine |
| DMA | dimethylacetamide |
| DME | 1,2-dimethoxyethane |
| DMF | N,N-dimethylformamide |
| DMSO | dimethylsulphoxide |
| dppf | 1,1'-bis(diphenylphosphino)ferrocene |
| EDC | 1-(3-dimethylaminopropyl)-3-ethylcarbodiimide hydrochloride |
| equiv. | equivalent(s) |
| ESI | electron spray ionization |
| Et | ethyl |
| Et₂O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |

| List of abbreviations | |
|---|---|
| hept | heptane |
| HOBt | 1-hydroxybenzotriazole |
| HPLC | high performance liquid chromatography |
| conc. | concentrated |
| LiHMDS | lithium bis(trimethylsilyl)amide |
| mCPBA | 3-chloroperoxbenzoic acid |
| Me | methyl |
| MeOH | methanol |
| min | minutes |
| MS | mass spectrometry |
| MTBE | methyl tertiary butyl ether |
| NBS | N-bromo-succinimide |
| NIS | N-iodo-succinimide |
| NMP | N-methylpyrrolidone |
| Rt | retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tertiary-butyl |
| TEA | triethylamine |
| temp. | temperature |
| tert | tertiary |
| TFA | trifluoroacetic acid |
| THF | tetrahydrofuran |
| TLC | thin layer chromatography |
| TsOH | p-toluenesulphonic acid |

General Synthetic Methods and Synthesis of Intermediates

The compounds of the invention may be prepared by the methods and examples presented below and methods known to those of ordinary skill in the art. In each of the examples below, the groups HET, X, Y, $R^1$ and $R^2$ are as defined above for general formula I unless noted. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or Preparatory HPLC.

Intermediates

Synthesis of 2-fluoro-5-iodo-4-methyl-benzoic acid
(I-1)

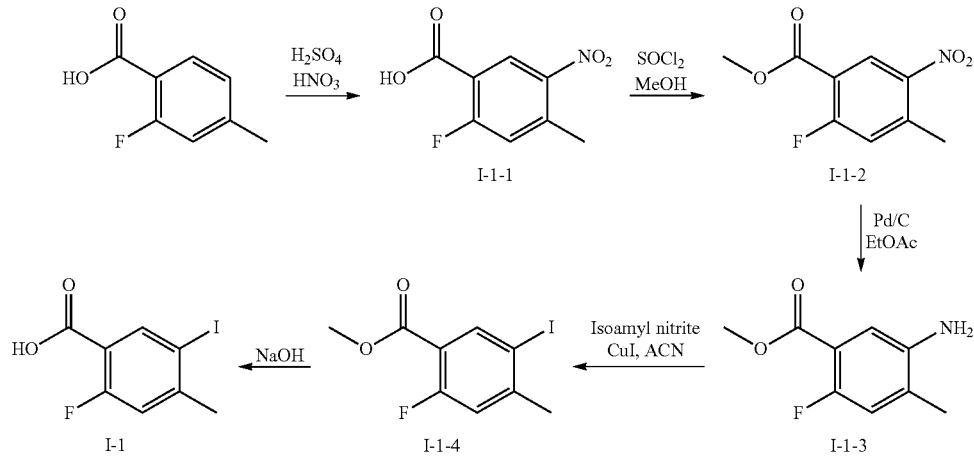

To a stirred solution of 2-fluoro-4-methyl benzoic acid (26 g, 168 mmol) in concentrated H₂SO₄ (260 mL) is dropwise added freshly prepared nitration mixture [concentrated H₂SO₄ (10.7 mL)+70% HNO₃ (11.9 mL)] at 0° C. over 45 min. The resultant solution is stirred for 3 h at 0° C. The reaction mixture is quenched with ice water. The resulting heterogeneous solution is extracted with ethyl acetate. The combined organic layer is washed with water, brine, dried over anhydrous MgSO₄, filtered and concentrated under reduced pressure to afford 30 g of crude 2-fluoro-4-methyl-5-nitro-benzoic acid (I-1-1).

To a stirred solution of I-1-1 (30 g, 150 mmol) in methanol (300 mL) is added thionyl chloride (22.5 mL, 301 mmol) dropwise at 10° C. The resultant solution is warmed to reflux. After 12 h, the solvent is concentrated under reduced pressure and the crude residue is partitioned between ethyl acetate and water. The organic layer is separated and washed with saturated NaHCO₃ solution, water, brine, dried over anhydrous MgSO₄, filtered and concentrated under reduced pressure to afford 30 g of methyl 2-fluoro-4-methyl-5-nitro-benzoate (I-1-2).

The solution of methyl I-1-2 (30 g, 141 mmol) in methanol (600 mL) was charged to a 2 liter Parr pressure vessel. Palladium, 10% on carbon (3 g, 28 mmol), is then added under nitrogen atmosphere. The Parr vessel is put under a hydrogen atmosphere (45 psi). After 12 h, the reaction mass is filtered through celite and the filtrate is concentrated under reduced pressure to afford 26 g of methyl 5-amino-2-fluoro-4-methyl-benzoate (I-1-3).

To a stirred solution of I-1-3 (26 g, 142 mmol) in acetonitrile (540 mL) at −5° C. is dropwise added isoamyl nitrite (21.7 g, 184 mmol). After 5 min, copper (I) iodide (56 g, 369 mmol) is added portion wise to the reaction mixture and the resultant mixture is slowly heated to 65° C. for 2 h. The solution is filtered through celite and the filtrate is concentrated under reduced pressure. Flash column chromatography (silical gel, eluent with 5% ethyl acetate in hexane) yields 20 g of methyl 2-fluoro-5-iodo-4-methyl-benzoate (I-1-4).

To a stirred solution of I-1-4 (20 g, 68 mmol) in THF: MeOH:H₂O (1:1:1, 300 mL) is added solid NaOH (4 g, 102 mmol) at room temperature. The resultant solution is stirred for 3 h at room temperature. The solvent is concentrated under reduced pressure and the residue is diluted with water (500 mL) and washed with ethyl acetate (2×150 mL). The pH of the aqueous layer is adjusted to pH 2 by addition of 10% aqueous HCl and then extracted with DCM (3×150 mL). The combined organic layer is washed with water (2×100 mL), brine (200 mL), dried over anhydrous MgSO₄, filtered and concentrated under reduced pressure to afford 2-fluoro-5-iodo-4-methyl-benzoic acid (I-1).

The following intermediates are synthesized according to the procedure described in Example 1:

4-Chloro-2-fluoro-5-iodo-benzoic acid (I-2)
4-Chloro-2-fluoro-5-bromo-benzoic acid (I-3)

Synthesis of N-cyclopropyl-4-methyl-3-(1H-pyrazol-4-yl)benzamide (I-4)

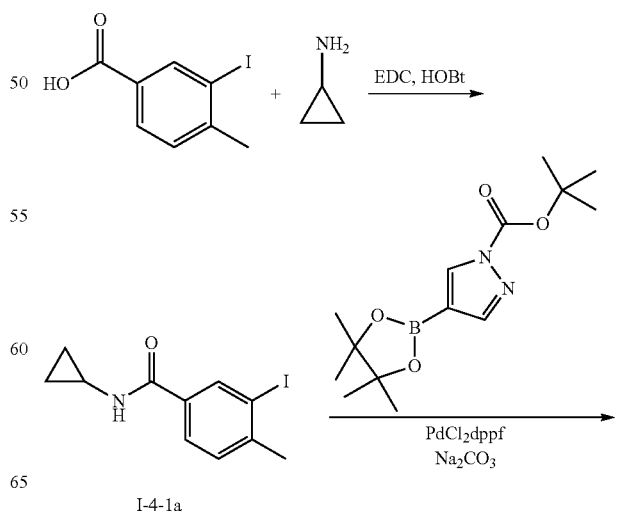

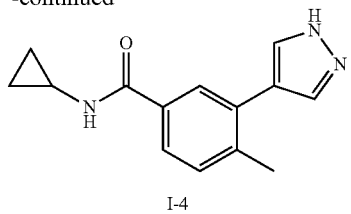

I-4

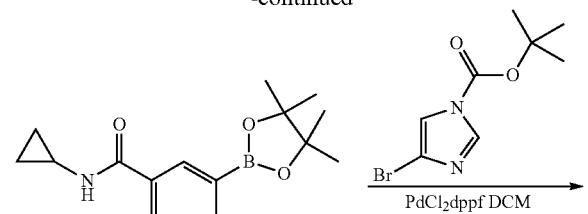

I-8-1

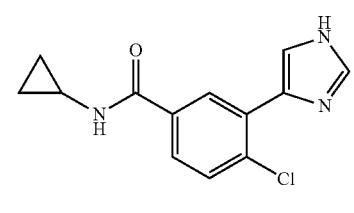

I-8

To a stirred solution of 3-iodo-4-methyl-benzoic acid (42 g, 160 mmol) in DMF (400 mL) at room temperature, is added EDC HCl (92 g, 481 mmol) followed by HOBt (32 g, 240 mmol). The reaction mixture is stirred for 30 min followed by the addition of cyclopropylamine (13.3 mL, 192 mmol) and DIPEA (140 mL, 802 mmol). After 16 h, the reaction is quenched with water and extracted with EtOAc. The combined organic layer is washed with brine, dried over anhydrous $MgSO_4$, and evaporated under reduced pressure. The crude material is washed with 20% EtOAc in hexane (200 mL) to afford 45 g of N-cyclopropyl-3-iodo-4-methyl-benzamide (I-4-1a).

The following intermediates are synthesized according to the general procedure described for Intermediate I-4-1a:

5-Bromo-N-cyclopropyl-2-fluoro-4-methyl-benzamide (I-4-1b)

4-Chloro-N-cyclopropyl-3-iodo-benzamide (I-4-1c)

4-Chloro-N-cyclopropyl-2-fluoro-benzamide (I-4-1d) To a solution of I-4-1a (20 g, 66.4 mmol) in 1,4-dioxane (500 mL), at ambient temperature, is added tert-butyl 4-(4,4,5,5-tetramethyl-1,3,2-dioxaborolan-2-yl)pyrazole-1-carboxylate (23.4 g, 79.7 mmol) followed by $Na_2CO_3$ (21.1 g, 199 mmol) and water (150 mL). The reaction mixture is degassed and refilled with nitrogen two times. $PdCl_2$(dppf) (5.4 g, 6.6 mmol) is added and the reaction mixture is heated at 110° C. for 4 h. The reaction mixture is cooled and evaporated under reduced pressure. The crude residue is purified by flash column chromatography on silica gel (eluent with 3% MeOH in EtOAc) to yield 15.2 g of N-cyclopropyl-4-methyl-3-(1H-pyrazol-4-yl)benzamide (I-4).

The following intermediates are synthesized according to the general procedure described in I-4:

N-Cyclopropyl-2-fluoro-4-methyl-5-(1H-pyrazol-4-yl)benzamide (I-5)

4-Chloro-N-cyclopropyl-2-fluoro-5-(1H-pyrazol-4-yl)benzamide (I-6)

4-Chloro-N-cyclopropyl-3-(1H-pyrazol-4-yl)benzamide (I-7)

Synthesis of 4-chloro-N-cyclopropyl-3-(1H-imidazol-4-yl)benzamide (I-8)

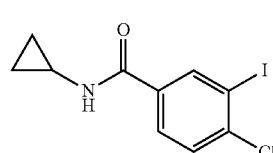

I-4-1c

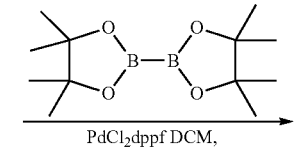

To a degassed stirred solution of compound I-4-1c (5 g, 15.5 mmol), bis(pinacolato)diboron (11.8 g, 46.7 mmol) and KOAc (5 g, 46.7 mmol) in toluene (150 mL) is added $PdCl_2$(dppf)$CH_2Cl_2$ adduct (0.6 g, 0.15 mmol) under nitrogen atmosphere. The resulting mixture is again degassed under nitrogen atmosphere and then heated to 95° C. for 24 h. The reaction mass is cooled to ambient temperature and the catalyst if filtered through Celite. The filtrate is concentrated under reduced pressure and the residue is purified via flash column chromatography (silica-gel, 10% ethyl acetate in hexane) to afford 4.6 g of 4-chloro-N-cyclopropyl-3-(4,4,5,5-tetramethyl-1,3,2-dioxaborolan-2-yl)benzamide (I-8-1).

To a degassed stirred solution of tert-butyl 4-bromoimidazole-1-carboxylate (2.5 g, 10.2 mmol) and I-8-1 (4.9 g, 15.2 mmol) in a mixture of 1,4-dioxane (63 mL) and water (30 mL) is added $Na_2CO_3$ (3.2 g, 30.4 mmol) followed by $PdCl_2$(dppf) $CH_2Cl_2$ (0.82 g, 1.1 mmol). The reaction mixture is degassed and the resultant solution is stirred at 100° C. for 16 h. The reaction mixture is cooled to room temperature, filtered and concentrated under reduced pressure. The crude mixture is purified by flash column chromatography on silica gel (eluent with 50% to 100% ethyl acetate in hexane) to afford 1.1 g of 4-chloro-N-cyclopropyl-3-(1H-imidazol-4-yl)benzamide (I-8).

The following intermediates are synthesized according to I-8:

4-Chloro-N-cyclopropyl-3-(1H-imidazol-4-yl)benzamide (I-9)

Synthesis of tert-butyl 4-[(5-bromo-3-pyridyl)amino]piperidine-1-carboxylate (I-15)

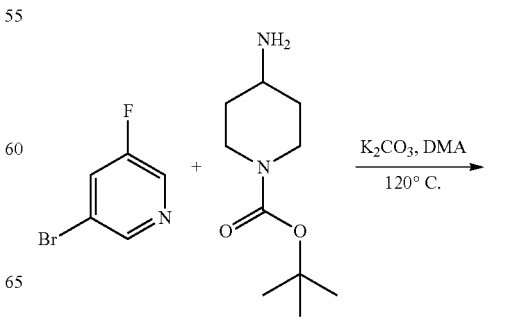

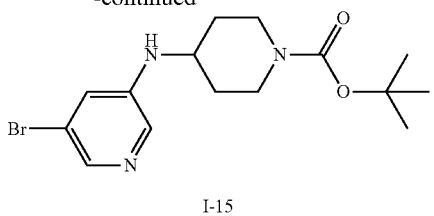

I-15

In 3 separate 20 mL microwavable pressure tubes, is added equal amounts of 3-bromo-5-fluoropyridine (2.0 g, 11.4 mmol per pressure tube), tert-butyl 4-aminopiperidine-1-carboxylate (3.41 g, 17.1 mmol per pressure tube), DMA (2.8 mL per pressure tube) and K$_2$CO$_3$ (1.57 g, 11.4 mmol per pressure tube). The pressure tubes are flushed with Ar, sealed and heated to 120 degrees C. After 96 h, the reaction mixtures are combined and partitioned between EtOAc and water. The layers are separated and the aqueous layer is extracted with EtOAc (2×). The combined organic layer is washed with water and brine, dried over MgSO$_4$, filtered and concentrated. Flash chromatography (120 g silica, 0-10% MeOH in DCM) affords 3.61 g of tert-butyl 4-[(5-bromo-3-pyridyl)amino]piperidine-1-carboxylate (I-15).

The following intermediates are synthesized according to the I-15 using either commercially available amine or amine previously described in the literature:

5-Bromo-N-[1-(2-methoxyethyl)-4-piperidyl]pyridin-3-amine (I-16)

exo-N-(5-Bromo-3-pyridyl)-8-(oxetan-3-yl)-8-azabicyclo[3.2.1]octan-3-amine (I-17)

5-Bromo-N-tetrahydropyran-4-yl-pyridin-3-amine (I-18)

Synthesis of 5-bromo-N-[1-(oxetan-3-yl)-4-piperidyl]pyridin-3-amine (I-19)

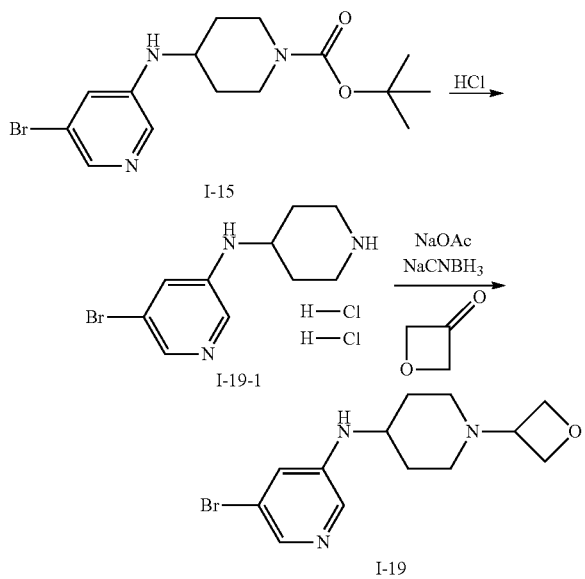

To a solution of I-15 (2.8 g, 7.9 mmol) in DCM (40 mL) is added 4M HCl in dioxane (30 mL, 120 mmol) dropwise. After 5 h, the reaction solution is decanted leaving behind a residue. DCM is added to the residue and stirred for 30 minutes. The solution is decanted and the residue is dried in vacuo to afford 2.95 g of 5-bromo-N-(4-piperidyl)pyridin-3-amine dihydrochloride (I-19-1) which is used without further purification.

To a mixture of I-19-1 (0.90 g, 2.7 mmol) in MeOH (18 mL) is added oxetan-3-one (1.34 mL, 20.5 mmol) and sodium acetate (0.953 g, 11.6 mmol). The reaction is stirred for 90 minutes, and then sodium cyanoborohydride (1.29 g, 20.5 mmol) is added. The solution is allowed to stir at room temperature for 4.5 h. The reaction is concentrated in vacuo and then re-dissolved in MeOH. Purification via reversed phase HPLC (mobile phase: ACN, H$_2$O with ammonium carbonate as base modifier) affords, after lyopholization, 0.35 g of 5-bromo-N-[1-(oxetan-3-yl)-4-piperidyl]pyridin-3-amine (I-19).

Synthesis of 3-[1-(5-bromo-3-pyridyl)pyrazol-4-yl]-N-cyclopropyl-4-methyl-benzamide (I-20)

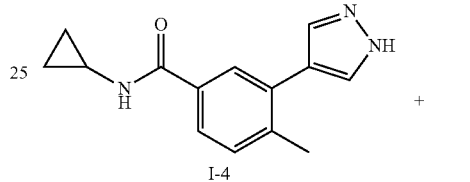

I-4

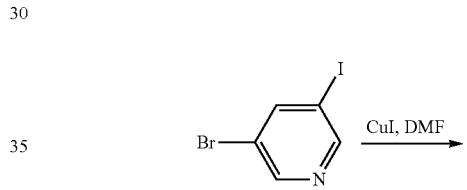

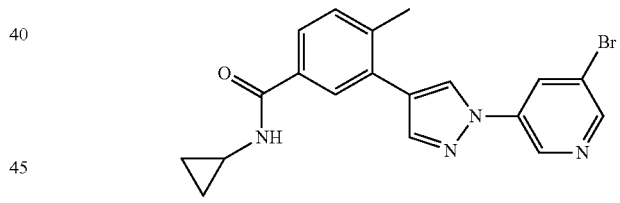

I-20

Pyrazole I-4 (5.0 g, 20.7 mmol), 3-bromo-5-iodo-pyridine (6.47 g, 22.8 mmol), CuI (1.58 g, 8.3 mmol), K$_3$PO$_4$ (9.0 g, 41.1 mmol) and trans-1,2-bis(methylamino)cyclohexane (2.62 mL, 16.6 mmol) are combined in DMF (50 mL) and stirred at room temperature. After 20 h, the reaction is partitioned between EtOAc and water, stirred vigorously and then allowed to stand. The layers are separated and the extraction process is repeated (2×). The combined organic extracts are washed with water (2×), brine, dried over MgSO$_4$, filtered and concentrated. Flash silica gel chromatography (MeOH in DCM; 0-10%) affords 4.65 g of 3-[1-(5-bromo-3-pyridyl)pyrazol-4-yl]-N-cyclopropyl-4-methyl-benzamide (I-20).

The following compound is prepared in an analogous fashion as I-20 using I-5:

5-[1-(5-Bromo-pyridin-3-yl)-1H-pyrazol-4-yl]-N-cyclopropyl-2-fluoro-4-methyl-benzamide (I-20b)

Synthesis of 3-[1-(5-methoxy-3-pyridyl)imidazol-4-yl]-4-methyl-benzoic acid (I-22)

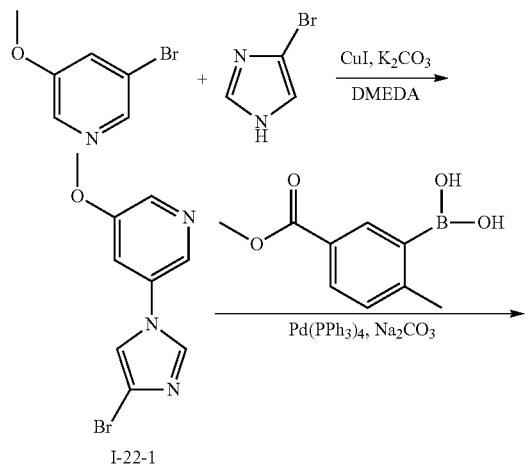

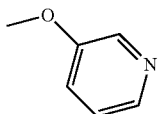

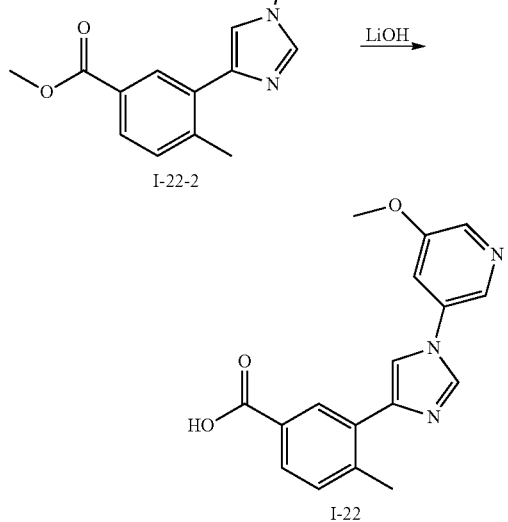

To a stirred solution of 3-bromo-5-methoxy-pyridine (5.00 g, 27 mmol) and 4-bromo-1H-imidazole (3.91 g, 27 mmol) in 50 mL DMF at 0° C. are added potassium carbonate (7.35 g, 53 mmol), CuI (0.506 g, 2.66 mmol), and N,N'-dimethylethylenediamine (0.145 mL, 1.33 mmol). The reaction is stirred 30 min at 0° C. then heated to 150° C. for 14 h. The reaction is quenched with ice water and extracted with EtOAc (2×150 mL). The combined organic layers are washed with water (3×), dried over Na₂SO₄ and concentrated under reduced pressure to afford 5 g of crude 3-(4-Bromoimidazol-1-yl)-5-methoxy-pyridine (I-22-1).

The following intermediates were prepared in analogous fashion to intermediate I-22-1:
3-(4-Bromopyrazol-1-yl)-5-methoxy-pyridine (I-23a)
3-(4-Bromopyrazol-1-yl)-5-cyclopropyl-pyridine (I-23b)

Intermediate I-22-1 (0.20 g, 0.79 mmol), (5-methoxycarbonyl-2-methyl-phenyl)boronic acid (0.153 g, 0.787 mmol), tetrakis (triphenylphosphine)palladium (0) (45.5 mg, 0.039 mmol), and sodium carbonate (0.250 g, 2.36 mmol), are combined with 2 mL of 1,4-dioxane and 1 mL water are combined in a microwave vial that is sealed and purged with argon. The reaction is heated at 130° C. in a microwave reactor for 30 min. The reaction is concentrated under reduced pressure and the residue diluted with EtOAc and water causing a solid to precipitate from solution. The formed solid is collected by filtration and dried to afford 0.100 g of methyl 3-[1-(5-methoxy-3-pyridyl)imidazol-4-yl]-4-methyl-benzoate (I-22-2).

To a solution of I-22-2 (0.10 g, 0.31 mmol) in 4 mL THF is added 2 mL water and lithium hydroxide monohydrate (0.025 mg, 0.60 mmol). The reaction is stirred at room temperature overnight, and then concentrated under reduced pressure. Additional water is added and the solution is acidified with 4 M HCl until a white solid precipitates. The formed solid is collected by vacuum filtration to afford 0.070 g of 3-[1-(5-methoxy-3-pyridyl)imidazol-4-yl]-4-methyl-benzoic acid (I-22).

The following intermediate is prepared according to I-22:
4-Chloro-3-[1-(5-methoxy-3-pyridyl)imidazole-4-yl]benzoic acid (I-22b)

Synthesis of 3-Methoxy-5-[4-(4,4,5,5-tetramethyl-[1,3,2]dioxaborolan-2-yl)-pyrazol-1-yl]-pyridine (I-24a)

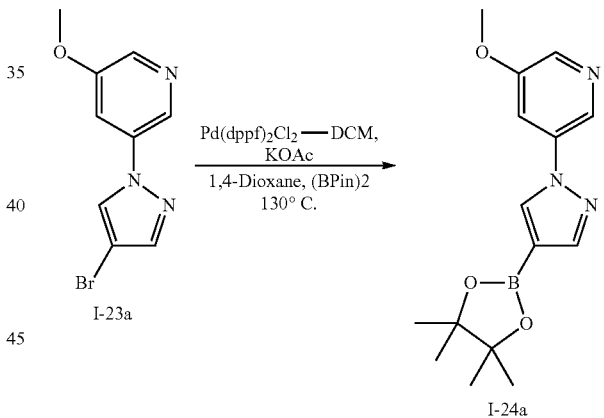

Bromide I-23a (1.0 g, 3.9 mmol), bis(pinacolato)diboron (2.0 g, 7.8 mmol) and KOAc (1.16 g, 11.8 mmol) are combined in 1,4-dioxane (15 mL). The Pd catalyst is added and the mixture is sparged with Ar for 5 minutes. The reaction vessel is sealed and heated at 120° C. for 5 h, then cooled to room temperature. The mixture is diluted with EtOAc and filtered through Celite. The Celite is washed with EtOAc and the filtrate is concentrated in vacuo. The crude product is purified by column chromatograph on silica (1% MeOH/DCM) to afford 378 mg of 3-Methoxy-5-[4-(4,4,5,5-tetramethyl-[1,3,2]dioxaborolan-2-yl)-pyrazol-1-yl]-pyridine (I-24a).

The following intermediate is prepared according to I-24a:
3-Cyclopropyl-5-[4-(4,4,5,5-tetramethyl-[1,3,2]dioxaborolan-2-yl)-pyrazol-1-yl]-pyridine (I-24b)

123

Synthesis of tert-Butyl-(3S,4R)-4-(benzylamino)-3-fluoropiperidine-1-caboxylate and tert-Butyl-(3R,4S)-4-(benzylamino)-3-fluoropiperidine-1-caboxylate (I-25 and I-26)

124

Synthesis of Tert-butyl (3R,4S)-4-[(5-bromopyridin-3-yl)amino]-3-fluoropiperidine-1-carboxylate (I-27)

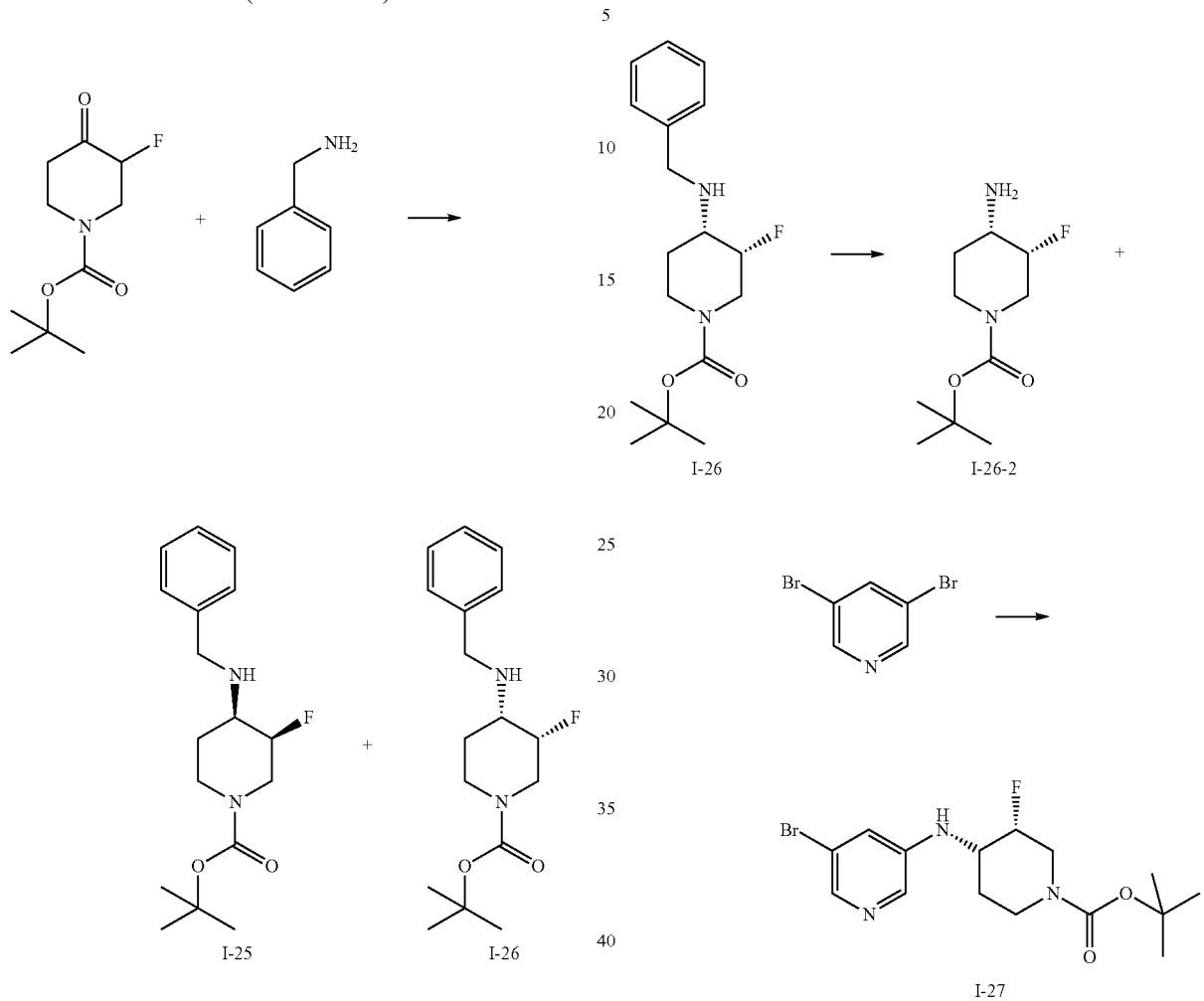

Tert-Butyl-3-fluoro-4-oxopiperidine-lcaboxylate (3.6 g, 16.8 mmol) was dissolved in DCM (50 mL) and cooled to 0° C. under $N_2$. N-benzylamine (1.9 mL, 17.4 mmol) was added followed by sodium triacetoxyborohydride (5.3 g, 25.3 mmol) and the reaction mixture was allowed to warm to RT and stir for 2 h. To the mixture was added an 20% aqueous solution of $K_2CO_3$ (30 mL) and allowed to stir for 10 minutes. The organic layer was separated, washed with water, dried with $MgSO_4$, filtered and concentrated. The resulting residue was purified by silica gel chromatography (0-100% EtOAc in hexanes). The resulting racemic mixture was separated by chiral HPLC (ES Chromega chiral CCA 3×25 cm column with 4% MeOH (4 mM NH3) in supercritical CO2 for 7 min at 130 g/min. Column at 40*C and ABPR at 140 bar) to give I-25 (1.4 g, 4.5 mmol) and I-26 (1.4 g, 4.5 mmol).

I-26 (2.1 g, 6.8 mmol) was dissolved in EtOH (25 mL) and to this was added ammonium formate (1.7 g, 27.2 mmol) and water (3.0 mL) and the mixture allowed to stir for 10 min. To this was added 10% Pd/C (1.0 g) and the reaction heated at 100° C. for 1 h. The mixture was cooled to RT, filtered through celite and washed with MeOH. The resulting solution was concentrated to give I-26-2 tert-butyl (3R,4S)-4-amino-3-fluoropiperidine-1-carboxylate (1.2 g, 5.7 mmol) which used without further purification.

In a microwave reaction vessel was added tert-butyl (3R,4S)-4-amino-3-fluoropiperidine-1-carboxylate (0.5 g, 2.3 mmol), 3,5-dibromopyridine (0.81 g, 3.4 mmol), sodium tert-butoxide (0.53 g, 5.5 mmol), $Pd_2(dpa)_3$ (0.1 g, 0.11 mmol) and BINAP (0.2 g, 0.33 mmol) and the flask was purged with $N_2$ for 5 min. Pre-degassed toluene (10 mL) was added and the reaction vial was sealed. The resulting red slurry was heated at 120° C. in a heating block for 6 h. The mixture was cooled to RT, filtered through celite and concentrated. The resulting crude material was purified by silica gel chromatography (0-100% EtOAc in heptanes) to give I-27 tert-butyl (3R,4S)-4-[(5-bromopyridin-3-yl)amino]-3-fluoropiperidine-1-carboxylate (0.39 g, 1.0 mmol).

Synthesis of Tert-butyl (3S,4R)-4-[(5-bromopyridin-3-yl)amino]-3-fluoropiperidine-1-carboxylate (I-28)

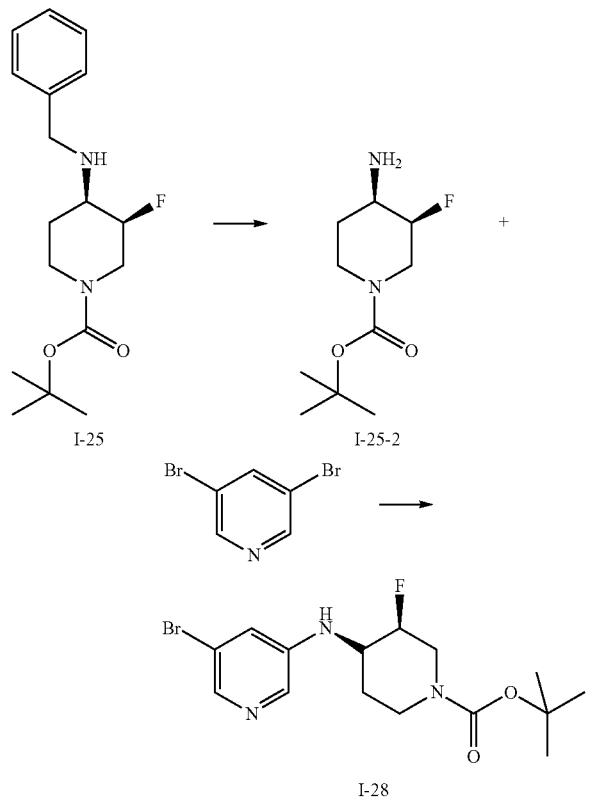

I-28 was prepared in an analogous fashion as I-27 starting from I-25.

Synthesis of ((3R,4S)-3-Fluoro-1-methyl-piperidin-4-yl)-(5-pyrazol-1-yl-pyridin-3-yl)-amine (I-29)

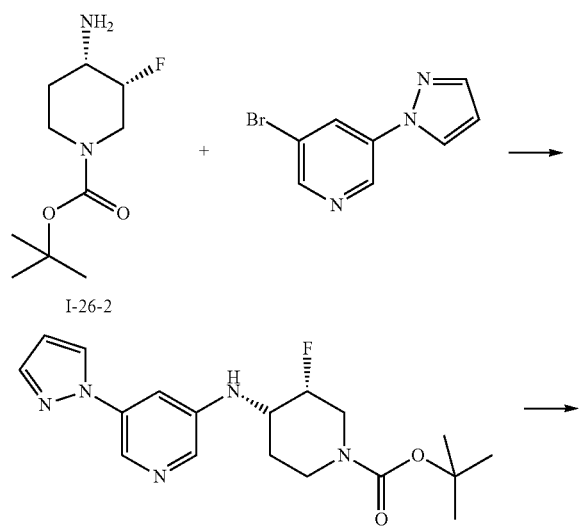

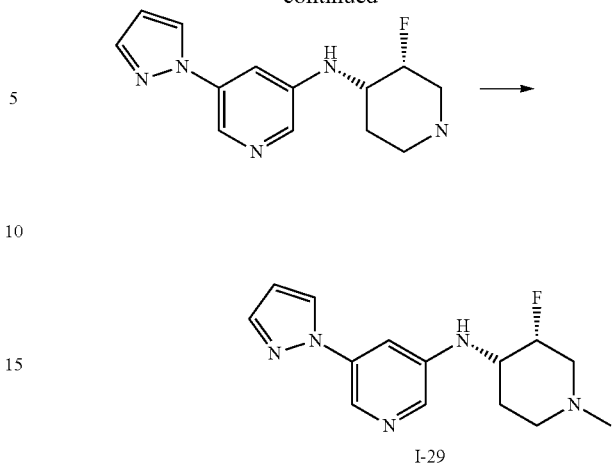

3-Bromo-5-(1H-pyrazol-1-yl)pyridine (0.50 g, 2.2 mmol) is placed in a microwave vial with I-26-2 (0.54 g, 2.5 mmol), sodium phenoxide (0.27 g, 2.3 mmol), 5-[Di(1-adamantyl)phosphino]1',3',5'-triphenyl-1'H[1,4']bipyrazole (0.030 g, 0.022 mmol) and allyl palladium (II) chloride dimer (0.008 g, 0.022 mmol) and dioxane (2.5 mL). The mixture is capped and heated at 110° C. for 2 h. The mixture is filtered through celite and the filtrate concentrated and purified by silica gel chromatography (0-100% EtOAc in heptanes) to give tert-butyl (3R,4S)-3-fluoro-4-{[5-(1H-pyrazol-1-yl)-pyridin-3-yl]amino}piperidine-cabarboxylate (0.67 g, 1.85 mmol, >98% ee).

Tert-butyl (3R,4S)-3-fluoro-4-{[5-(1H-pyrazol-1-yl)-pyridin-3-yl]amino}piperidine-cabarboxylate (0.15 g, 0.41 mmol) is dissolved in DCM (10 mL) and to this is added 4N HCl in dioxane (1.0 mL, 4.0 mmol) and the reaction stirred at RT for 3 h. The mixture was concentrated to give N-[(3R,4S)-3-fluoropiperidin-4-yl]-5-(1H-pyrazol-1-yl)pyridine-3-amine hydrochloride (0.14 g, 0.42 mmol).

N-[(3R,4S)-3-fluoropiperidin-4-yl]-5-(1H-pyrazol-1-yl)pyridine-3-amine hydrochloride (0.18 g, 0.55 mmol) is dissolved in MeOH (6.0 mL) and to this is added formaldehyde (37% wt in water, 0.31 mL, 4.2 mmol) and sodium acetate (0.23 g, 2.7 mmol). The reaction is stirred at RT for 90 min. Sodium cyanoborohyride (0.26 g, 4.3 mmol) is added. The mixture is stirred for 2 h at RT. The mixture is concentrated and water added. The resulting crude product was dissolved in DMF and purified directly by prep-HPLC to give I-29 (0.35 g, 0.13 mmol).

I-29 was recrystallized from methanol with slow evaporation. Suitable single crystals of I-29 were selected and placed on a Bruker APEX-II CCD diffractometer. The crystal was kept at 100.02 K during data collection. Using Olex2, the structure was solved with the olex2.solve structure solution program using charge flipping and refined with the olex2 refinement package using Gauss-Newton minimization which confirmed the assignment of the absolute stereochemistry as described.

Synthesis of ((3S,4R)-3-Fluoro-1-methyl-piperidin-4-yl)-(5-pyrazol-1-yl-pyridin-3-yl)-amine (I-30)

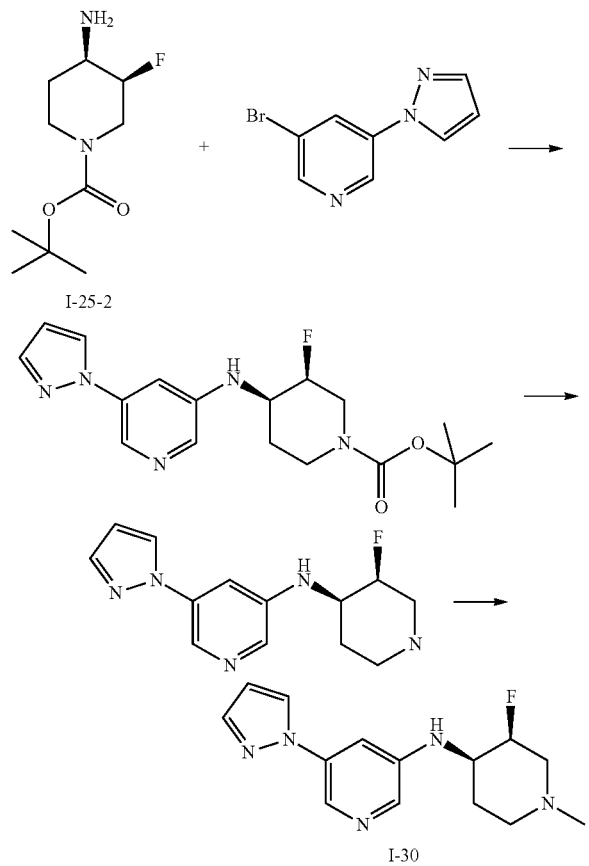

I-30 was prepared in an analogous fashion as I-29 starting with I-25-2.

I-30 was recrystallized from methanol with slow evaporation. Suitable single crystals of I-30 were selected and placed on a Bruker APEX-II CCD diffractometer. The crystal was kept at 100.02 K during data collection. Using Olex2, the structure was solved with the olex2.solve structure solution program using charge flipping and refined with the olex2 refinement package using Gauss-Newton minimization which confirmed the assignment of the absolute stereochemistry as described.

Final Compounds

N-Cyclopropyl-2-fluoro-5-[1-(5-methoxy-pyridin-3-yl)-1H-pyrazol-4-yl]-4-methyl-benzamide

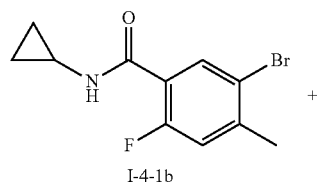

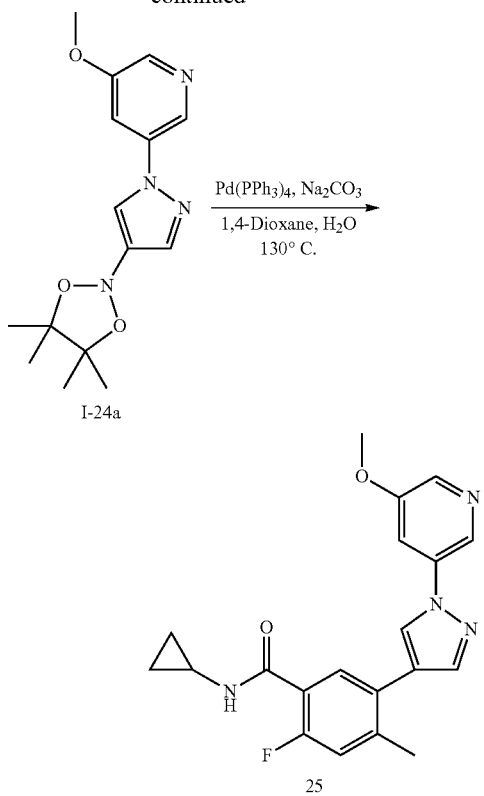

Bromide I-4-1b (0.100 g, 0.367 mmol), I-24a (111 mg, 0.37 mmol), tetrakis-(triphenylphosphine)palladium(0) (21.2 mg, 0.018 mmol), and sodium carbonate (117 mg, 1.1 mmol) are sealed in a microwave vial and purged with argon. To this is added 2 mL of 1,4-dioxane and 1 mL of water. The vial is heated in the microwave at 130° C. for 30 min. The solution is concentrated and the residue diluted with EtOAc. The organic layer is washed with water (2×), brine, then dried over $MgSO_4$, filtered and concentrated under reduced pressure. The residue is purified via flash silica gel chromatography (20-100% EtOAc in heptane) to give 0.104 g of the title compound (25).

The following compounds are synthesized according to the procedure for 25:

4-Chloro-N-cyclopropyl-2-fluoro-5-[1-(5-methoxy-pyridin-3-yl)-1H-pyrazol-4-yl]-benzamide (26)

4-Chloro-N-cyclopropyl-3-[1-(5-methoxy-pyridin-3-yl)-1H-pyrazol-4-yl]-benzamide (27)

N-Cyclopropyl-3-[1-(5-methoxy-pyridin-3-yl)-1H-pyrazol-4-yl]-4-methyl-benzamide (28)

4-Chloro-N-cyclopropyl-3-(1-pyridin-3-yl-1H-pyrazol-4-yl)-benzamide (31)

4-Chloro-N-cyclopropyl-2-fluoro-5-(1-pyridin-3-yl-1H-pyrazol-4-yl)-benzamide (32)

4-Chloro-N-cyclopropyl-2-fluoro-5-[1-(5-methoxy-pyridin-3-yl)-1H-imidazol-4-yl]-benzamide (33)

N-Cyclopropyl-4-methyl-3-(1-pyridin-3-yl-1H-pyrazol-4-yl)-benzamide (34)

N-Cyclopropyl-4-methyl-3-(1-pyridin-3-yl-1H-imidazol-4-yl)-benzamide (35)

129

N-Cyclopropyl-3-[1-(5-ethoxy-pyridin-3-yl)-1H-pyrazol-4-yl]-4-methyl-benzamide (36)

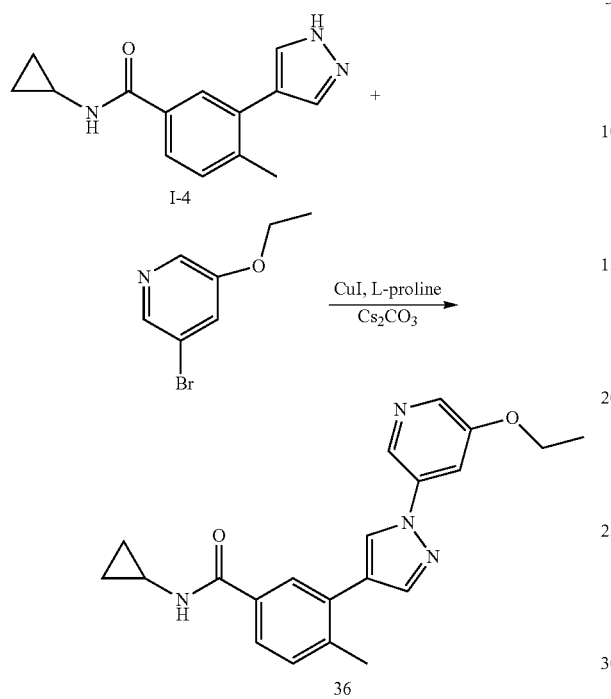

Pyrazole I-4 (0.100 g, 0.414 mmol), 3-bromo-5-ethoxy-pyridine (0.092 g, 0.46 mmol), CuI (0.0079 g, 0.041 mmol), L-proline (0.0095 g, 0.083 mmol) and cesium carbonate (0.203 g, 0.622 mmol) are combined in a microwave vial and 1 mL of DMF is added. The reaction vessel is sealed and purged with argon. The reaction is heated in a microwave reactor at 150° C. for 30 min. The mixture is filtered and the crude material is purified by reverse phase HPLC (ACN/H$_2$O with 0.1% (NH$_4$)$_2$CO$_3$) to afford 0.037 g of the title compound (36).

The following compounds are synthesized according to the procedure for example 36:

N-Cyclopropyl-4-methyl-3-[1-(5-methylaminomethyl-pyridin-3-yl)-1H-pyrazol-4-yl]-benzamide (39)

N-Cyclopropyl-3-[1-(5-hydroxymethyl-pyridin-3-yl)-1H-pyrazol-4-yl]-4-methyl-benzamide (43)

N-Cyclopropyl-3-[1-(5-dimethylamino-pyridin-3-yl)-1H-pyrazol-4-yl]-4-methyl-benzamide (44)

N-Cyclopropyl-3-[1-(5-cyclopropyl-pyridin-3-yl)-1H-pyrazol-4-yl]-4-methyl-benzamide (45)

N-Cyclopropyl-3-[1-(5-methanesulfonyl-pyridin-3-yl)-1H-pyrazol-4-yl]-4-methyl-benzamide (46)

N-Cyclopropyl-4-methyl-3-[1-(5-trifluoromethyl-pyridin-3-yl)-1H-pyrazol-4-yl]-benz amide (47)

5-[4-(5-Cyclopropylcarbamoyl-2-methyl-phenyl)-pyrazol-1-yl]-nicotinic acid (48)

5-[4-(5-Cyclopropylcarbamoyl-2-methyl-phenyl)-pyrazol-1-yl]-N,N-dimethyl-nicotinamide (49)

3-{1-[5-(1-Acetylamino-1-methyl-ethyl)-pyridin-3-yl]-1H-pyrazol-4-yl}-N-cyclopropyl-4-methyl-benzamide (50)

{5-[4-(5-Cyclopropylcarbamoyl-2-methyl-phenyl)-pyrazol-1-yl]-pyridin-3-yl}-acetic acid (51)

3-[1-(5-Cyanomethyl-pyridin-3-yl)-1H-pyrazol-4-yl]-N-cyclopropyl-4-methyl-benzamide (52)

130

N-Cyclopropyl-3-[1-(5-methoxy-pyridin-3-yl)-1H-imidazol-4-yl]-4-methyl-benzamide (53)

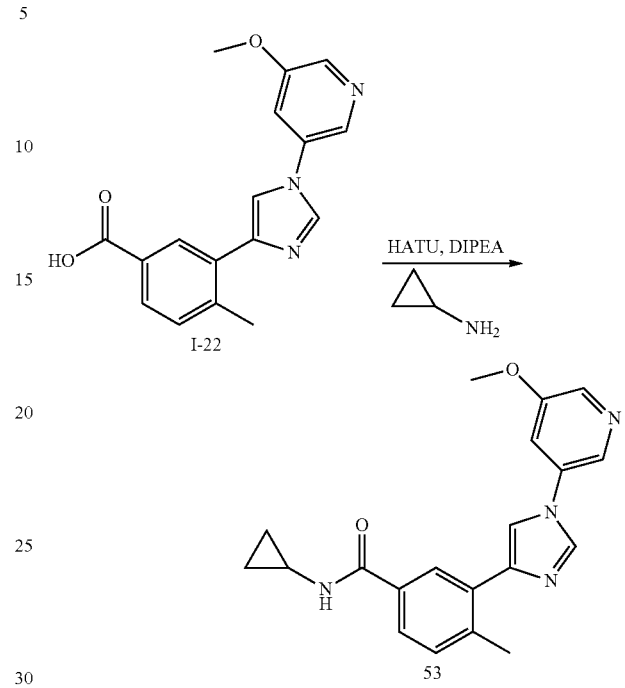

Intermediate I-22 (0.070 g, 0.22 mmol), cyclopropylamine (0.125 mL, 1.81 mmol), HATU (0.947 g, 0.250 mmol), and N,N-diisopropylethylamine (0.079 mL, 0.453 mmol) are combined in DMF (8 mL) and stirred at room temperature overnight. The reaction is purified by preparatory reverse phase HPLC (5-100% ACN/H$_2$O) to afford 0.039 g of the title compound (53).

The following compound is synthesized according to the procedure for Example 53:

4-Chloro-N-cyclopropyl-3-[1-(5-methoxy-pyridin-3-yl)-1H-imidazol-4-yl]-benzamide (54)

3-{1-[5-(2-tert-Butoxy-ethylamino)-pyridin-3-yl]-1H-pyrazol-4-yl}-N-cyclopropyl-4-methyl-benzamide (55)

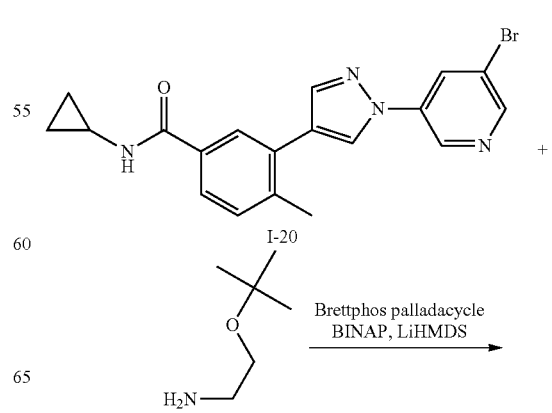

Synthesis of N-cyclopropyl-2-fluoro-4-methyl-5-{1-[5-(1-oxetan-3-yl-piperidin-4-ylamino)-pyridin-3-yl]-1H-pyrazol-4-yl}-benzamide (68)

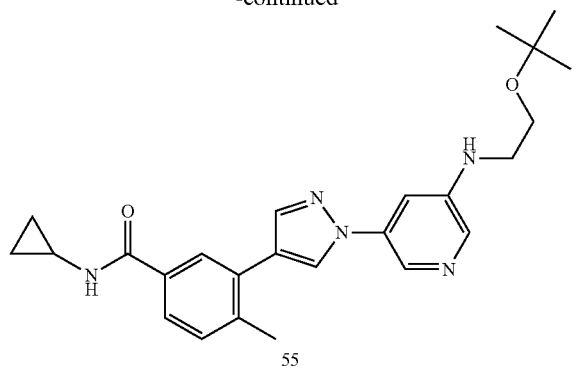

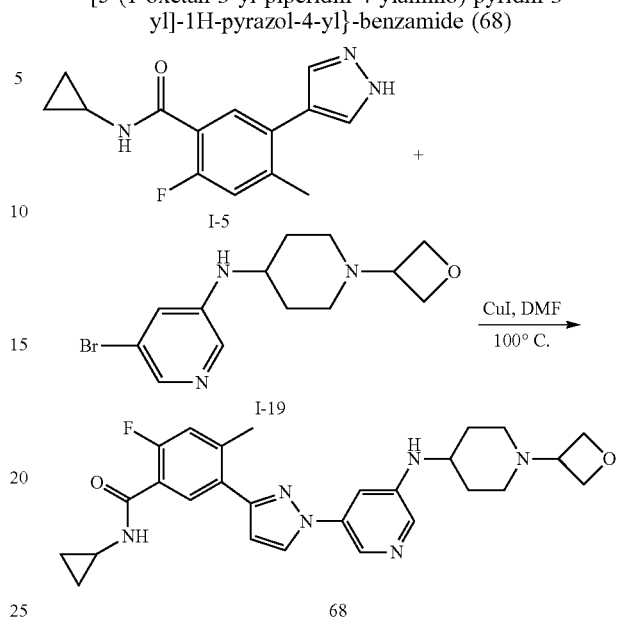

To a mixture of 2-(dicyclohexylphosphino)-3,6-dimethoxy-2',4',6'-triisopropyl-1,1'-biphenyl (0.0070 g (0.013 mmol) and Brettphos palladacycle (0.0104 g, 0.013 mmol) is added a solution of I-20 (0.050 g, 0.13 mmol) in 1 mL of THF. The vial is sealed and lithium bis(trimethylsilyl)amide (0.315 mL (0.315 mmol) is added. The vessel is flushed with argon and heated to 80° C. overnight. To this mixture is added water and the solution is extracted twice with EtOAc. The combined organic extracts are gravity eluted through a Biotage Si-thiol cartridge and the cartridge flushed with additional 1 mL of EtOAc. The collected sample is concentrated under reduced pressure and the residue purified via reverse phase HPLC to afford 0.005 g of the title compound (55).

The following intermediates are synthesized according to the Example 55 using commercially available amines or amines previously described in the literature:

N-Cyclopropyl-3-{1-[5-(3S,4R)-4-ethoxy-tetrahydro-furan-3-ylamino)-pyridin-3-yl]-1H-pyrazol-4-yl}-4-methyl-benzamide (56)

N-Cyclopropyl-3-(1-{5-[([1,4]dioxan-2-ylmethyl)-amino]-pyridin-3-yl}-1H-pyrazol-4-yl)-4-methyl-benzamide (57)

N-Cyclopropyl-4-methyl-3-(1-{5-[2-(2-oxo-oxazolidin-3-yl)-ethylamino]-pyridin-3-yl}-1H-pyrazol-4-yl)-benzamide (58)

N-Cyclopropyl-4-methyl-3-(1-{5-[(tetrahydro-furan-2-ylmethyl)-amino]-pyridin-3-yl}-1H-pyrazol-4-yl)-benzamide (59)

N-Cyclopropyl-3-{1-[5-(2-methoxy-ethylamino)-pyridin-3-yl]-1H-pyrazol-4-yl}-4-methyl-benzamide (60)

3-{1-[5-(1-Acetyl-piperidin-4-ylamino)-pyridin-3-yl]-1H-pyrazol-4-yl}-N-cyclopropyl-4-methyl-benzamide (63)

N-Cyclopropyl-3-{1-[5-(3-methoxy-cyclopentylamino)-pyridin-3-yl]-1H-pyrazol-4-yl}-4-methyl-benzamide (65)

N-Cyclopropyl-4-methyl-3-(1-{5-[(1S,2R,4R)-(7-oxa-bi-cyclo[2.2.1]hept-2-yl)amino]-pyridin-3-yl}-1H-pyrazol-4-yl)-benzamide (66)

N-Cyclopropyl-4-methyl-3-(1-{5-[1-(tetrahydro-furan-3-yl)-ethylamino]-pyridin-3-yl}-1H-pyrazol-4-yl)-benzamide (67)

Pyrazole I-5 (0.175 g; 0.680 mmol), bromide I-19 (0.221 g, 0.710 mmol), copper iodide (0.051 g, 0.27 mmol), potassium phosphate (0.287 g, 1.35 mmol) and trans-1,2-bis (methylamino)cyclohexane (0.085 mL, 0.54 mmol) are combined in DMF (1.75 mL) and heated to 100° C. After 18 h, the reaction is concentrated under reduced pressure and partitioned between EtOAc and H$_2$O. The layers are separated and the aqueous layer is extracted with EtOAc. The combined EtOAc layers are washed with brine, dried over MgSO$_4$, filtered and concentrated under reduced pressure. The crude residue is purified via reversed phase HPLC (mobile phase: ACN, H$_2$O with ammonium carbonate as base modifier) to afford, after lyopholization, 0.255 g of the title compound (68).

The following compounds are synthesized according to the Example 68 using commercially available heteroaryl bromide and/or intermediates described herein:

N-Cyclopropyl-3-[1-(5-cyclopropyl-pyridin-3-yl)-1H-imidazol-4-yl]-4-methyl-benzamide (71)

N-Cyclopropyl-3-[1-(5-dimethylamino-pyridin-3-yl)-1H-imidazol-4-yl]-4-methyl-benzamide (72)

4-{5-[4-(5-Cyclopropylcarbamoyl-2-methyl-phenyl)-pyrazol-1-yl]-pyridin-3-ylamino}-piperidine-1-carboxylic acid tert-butyl ester (73)

N-Cyclopropyl-2-fluoro-5-(1-{5-[1-(2-methoxy-ethyl)-piperidin-4-ylamino]-pyridin-3-yl}-1H-pyrazol-4-yl)-4-methyl-benzamide (74)

N-Cyclopropyl-2-fluoro-4-methyl-5-{1-[5-(8-oxetan-3-yl-8-aza-bicyclo[3.2.1]oct-3-ylamino)-pyridin-3-yl]-1H-pyrazol-4-yl}-benzamide (75)

N-Cyclopropyl-4-methyl-3-{1-[5-(1-methyl-piperidin-4-ylamino)-pyridin-3-yl]-1H-pyrazol-4-yl}-benzamide (76)

N-Cyclopropyl-2-fluoro-4-methyl-5-{1-[5-(1-methyl-piperidin-4-ylamino)-pyridin-3-yl]-1H-pyrazol-4-yl}-benzamide (77)

N-Cyclopropyl-4-methyl-3-{1-[5-(tetrahydro-pyran-4-ylamino)-pyridin-3-yl]-1H-pyrazol-4-yl}-benzamide (78)

N-Cyclopropyl-4-methyl-3-{1-[5-(1-oxetan-3-yl-piperidin-4-ylamino)-pyridin-3-yl]-1H-imidazol-4-yl}-benzamide (79)

3-[1-(5-Benzyloxy-pyridin-3-yl)-1H-pyrazol-4-yl]-N-cyclopropyl-4-methyl-benzamide (80)

N-Cyclopropyl-3-[1-(5-isopropoxy-pyridin-3-yl)-1H-pyrazol-4-yl]-4-methyl-benzamide (81)

N-Cyclopropyl-4-methyl-3-{1-[5-(piperidin-4-ylamino)-pyridin-3-yl]-1H-pyrazol-4-yl}-benzamide hydrochloride (92)

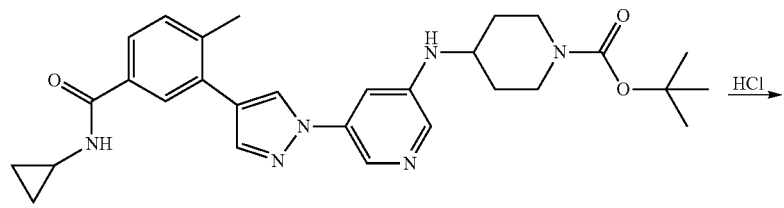

To a solution of carbamate 73 (0.30 g, 0.58 mmol) in dioxane is added HCl in dioxane (4M, 0.6 mL, 2.4 mmol) dropwise. After 4 h, the heterogeneous reaction solution is filtered and the collected solid is washed with DCM (2×) and dried to afford 0.23 g of the titled compound (92).

3-{1-[5-(1-Cyclobutyl-piperidin-4-ylamino)-pyridin-3-yl]-1H-pyrazol-4-yl}-N-cyclopropyl-4-methyl-benzamide (93)

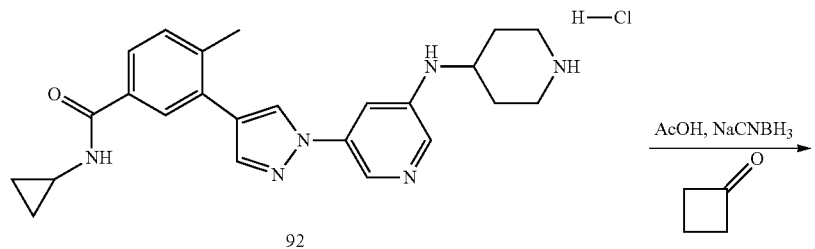

To a solution of 92 (0.045 g, 0.11 mmol) in MeOH (1 mL) is added glacial acetic acid (0.13 mL), followed by cyclobutanone (0.061 mL, 0.81 mmol) and sodium cyanoborohydride (0.051 g, 0.81 mmol). The solution is allowed to stir at room temperature for 5 h. The crude solution is concentrated under reduced pressure, re-dissolved in a minimal amount of MeOH, and purified via reversed phase HPLC (ACN, $H_2O$ with ammonium carbonate as base modifier) to afford, after lyophilization, 0.025 g of the titled compound (93).

The following compound is synthesized according to the Example 93 using commercially available ketone and/or intermediates described herein:

N-Cyclopropyl-4-methyl-3-{1-[5-(1-oxetan-3-yl-piperidin-4-ylamino)-pyridin-3-yl]-1H-pyrazol-4-yl}-benzamide (94)

N-Cyclopropyl-3-[1-(5-hydroxy-pyridin-3-yl)-1H-pyrazol-4-yl]-4-methyl-benzamide (95)

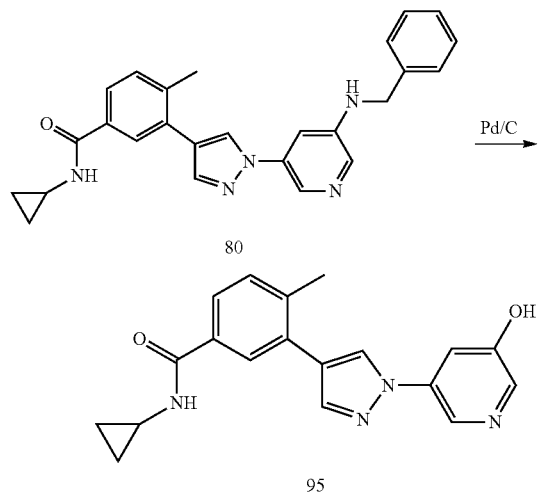

Pyrazole 80 (0.20 g, 0.47 mmol) is added to 10 mL of a 2:1 MeOH:EtOAc solution. The heterogeneous solution is warmed to dissolve the solid. The reaction is cooled to room temperature and flushed with Ar. 10% Pd/C (0.030 g) is then added and the reaction vessel is evacuated and flushed with H₂ (3×). After 2 h, the reaction is flushed with Ar. The solution is warmed to dissolve all of the white precipitate and more Pd/C (30 mg) is then added. The reaction vessel is evacuated and flushed with H₂ (3×). After another 22 h, the reaction is flushed with Ar. The solution is warmed, hot filtered and concentrated to yield 0.155 g of solid. The solid is re-dissolved in hot MeOH, cooled to room temperature, filtered (PTFE filter 0.45 □M) and concentrated to yield 0.147 g of the title compound (95).

N-Cyclopropyl-4-methyl-3-{1-[5-(tetrahydro-pyran-4-yloxy)-pyridin-3-yl]-1H-pyrazol-4-yl}-benzamide (96)

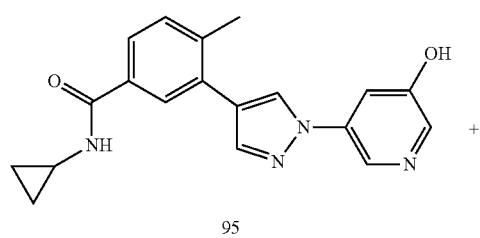

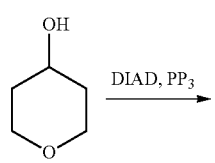

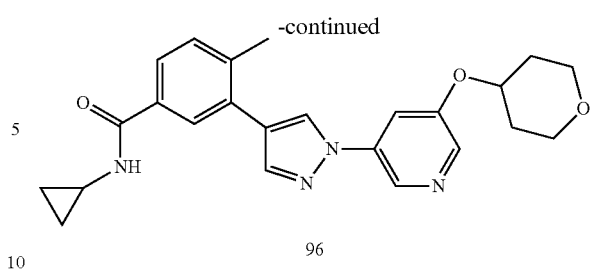

Phenol 95 (0.080 g, 0.24 mmol) is dissolved in DMF (1 mL) and tetrahydropyran-4-ol is added, followed by PPh₃ (0.14 g, 0.53 mmol) and di-isopropyl-azodicarboxylate (0.10 mL, 0.53 mmol). The solution is stirred at room temperature. After 18 h, more triphenylphosphine (0.31 g, 0.12 mmol) and di-isopropyl-azodicarboxylate (0.020 mL, 0.12 mmol) is added. After another 18 h, the reaction is diluted with 3 drops of water, filtered, concentrated in vacuo, and purified by reversed phase prepratory HPLC (ACN, H₂O with formic acid modifier) to afford 0.022 g of the tide compound (96).

3-[1-(5-Cyclohexylamino-pyridin-3-yl)-1H-pyrazol-4-yl]-N-cyclopropyl-4-methyl-benzamide (97)

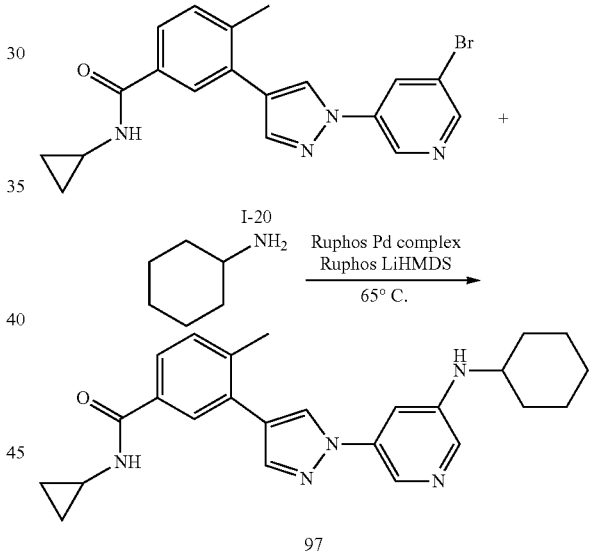

Bromide I-20 (0.050 g; 0.13 mmol), Ruphos Pd complex (0.010 g; 0.01 mmol), 2-dicyclohexylphosphino-2',6'-di-i-propoxy-1,1'-biphenyl (0.006 g; 0.01 mmol), and cyclohexylamine (0.03 ml; 0.25 mmol) are combined in THF (1.0 ml). To the reaction is added 1M LiHMDS in THF (0.30 ml; 0.30 mmol). The resultant mixture is stirred at 65° C. for 16 hours. The reaction is concentrated under reduced pressure and the residue is re-dissolved in a minimal amount of methanol. The mixture is purified by reversed phase MPLC (mobile phase: ACN, H₂O with TFA as acid modifier) to afford 0.012 g of the title compound (97).

The following compounds are synthesized according to the Example 97 using commercially available amines:

N-Cyclopropyl-4-methyl-3-[1-(5-morpholin-4-yl-pyridin-3-yl)-1H-pyrazol-4-yl]-benzamide (98)

N-Cyclopropyl-3-{1-[5-(cyclopropylmethyl-amino)-pyridin-3-yl]-1H-pyrazol-4-yl}-4-methyl-benzamide (99)

N-Cyclopropyl-4-methyl-3-{1-[5-(4-methyl-piperazin-1-yl)-pyridin-3-yl]-1H-pyrazol-4-yl}-benzamide (100)

3-{1-[5-(1-Carbamoyl-cyclopropyl)-pyridin-3-yl]-1H-pyrazol-4-yl}-N-cyclopropyl-4-methyl-benzamide (101)

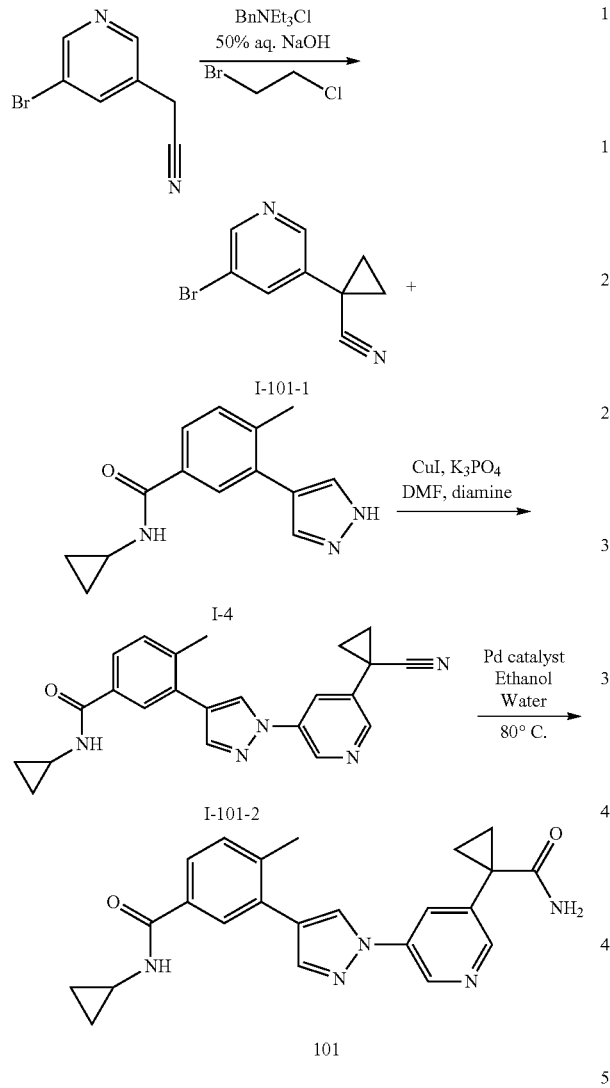

To a suspension of (5-bromo-pyridin-3-yl)-acetonitrile (1.0 g, 5.1 mmol) in 50% NaOH (20 ml) is added 1-bromo-2-chloro-ethane (764 mg, 5.33 mmol) and benzyltriethylammonium chloride (15 mg, 0.11 mmol). The resultant mixture is heated to 60° C. for 2 h. After cooling down to room temperature, EtOAc is added and extracted. The organic layer is combined and washed with brine, dried over Na₂SO₄, filtered and concentrated. The product is purified by column to afford 626 mg of 1-(5-bromo-pyridin-3-yl)-cyclopropanecarbonitrile (I-101-1)

Intermediate I-101-2 was prepared according to Example 101.

Nitrile I-101-2 (0.075 g, 0.20 mmol) and hydrido(dimethylphosphinous acid kP) [hydrogen bis(dimethylphosphinito-kP)] platinum (II) (0.010 g, 0.02 mmol) are combined in a mixture of water (0.5 ml, 1.25 mmol) and ethanol (1 ml, 1.25 mmol). The reaction mixture is stirred at 80° C. for 16 hours. The mixture is purified by reversed phase HPLC (mobile phase: ACN, H₂O with TFA as acid modifier) to afford 0.35 g of the title compound (101).

4-Chloro-N-cyclopropyl-5-[1-(5-cyclopropyl-pyridin-3-yl)-1H-pyrazol-4-yl]-2-fluoro-benzamide (104)

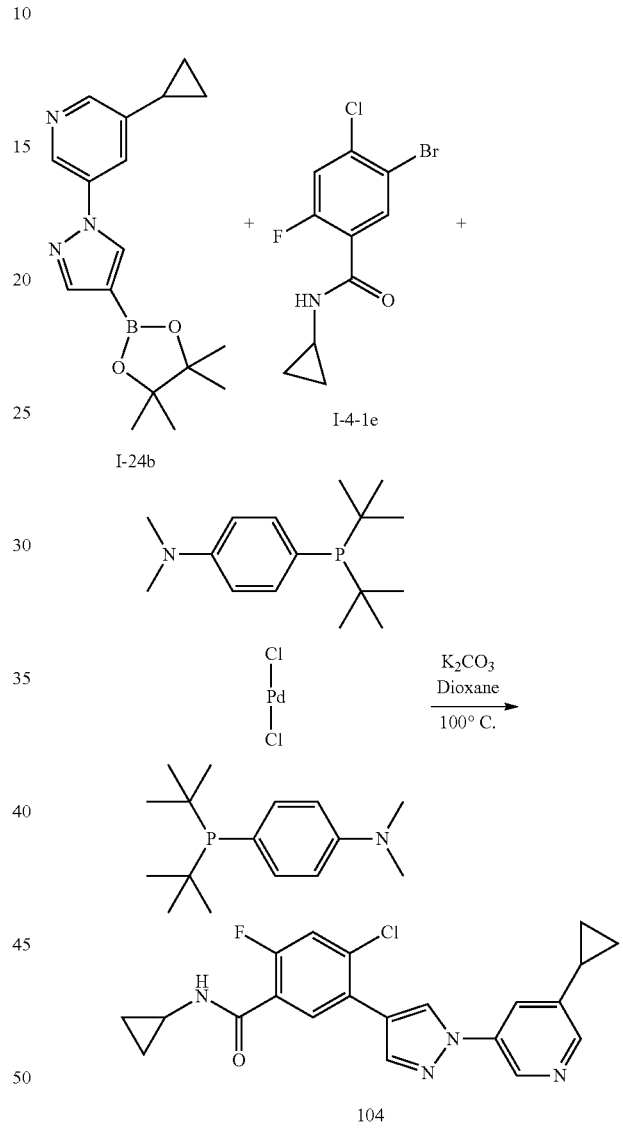

A pressure tube is charged with I-24b (0.100 g, 0.321 mmol), bromide I-4-1e (0.103 g; 0.353 mmol), bis(di-tert-butyl(4-dimethylaminophenyl)phosphine)dichloropalladium (II) (0.007 g, 0.01 mmol), and K₂CO₃ (0.089 g, 0.64 mmol). Dioxane (2 mL) and water (0.2 mL) are added and the mixture is sparged with Argon for 15 min. The tube is capped and the mixture is heated at 100° C. After 20 h, the mixture is cooled to room temperature, diluted with ethyl acetate (10 mL), and washed with brine (10 mL). Phases are separated, and the organic layer is dried over MgSO₄, filtered and concentrated. The residue is purified using reversed phase HPLC (mobile phase: ACN, H₂O with TFA as acid modifier). All the desired fractions are combined and lyophilized. The residue is dissolved in MeOH, passed through a PL-HCO₃ MP-resin, and concentrated under reduced pressure to afford 0.031 g of the title compound (104).

The following compound is synthesized according to the Example 104 using commercially available boronic ester and intermediates described herein:

N-Cyclopropyl-5-[1-(5-cyclopropyl-pyridin-3-yl)-1H-pyrazol-4-yl]-2-fluoro-4-methyl-benzamide (105)

3-[1-(5-Amino-pyridin-3-yl)-1H-pyrazol-4-yl]-N-cyclopropyl-4-methyl-benzamide (106)

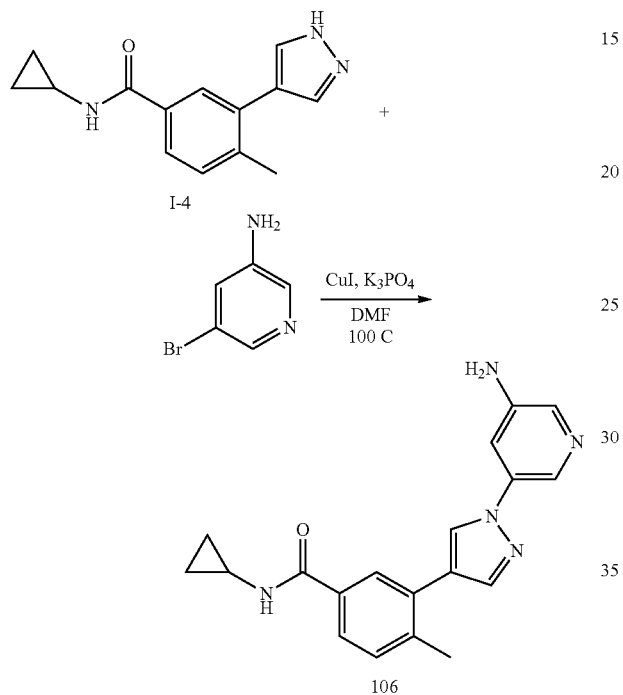

Pyrazole I-4 (1.1 g, 4.5 mmol), 5-bromo-pyridin-3-ylamine (1.0 g, 4.5 mmol), CuI (0.026 g, 0.14 mmol) and potassium phosphate (1.9 g, 9.1 mmol) are combined in degassed mixture of dioxane (20 mL) and DMSO (6 mL). Ethylene diamine (9.1 uL, 0.14 mmol) is added and the suspension is heated at 120° C. After heating for 16 hours, the reaction is partitioned between EtOAc and water. The layers are separated and the organic portion dried (MgSO₄), filtered and concentrated under reduced pressure. The residue is purified by flash silica gel chromatography to afford 0.357 g of the title compound (106).

N-Cyclopropyl-4-methyl-3-{1-[5-(3-methyl-ureido)-pyridin-3-yl]-1H-pyrazol-4-yl}-benzamide (107)

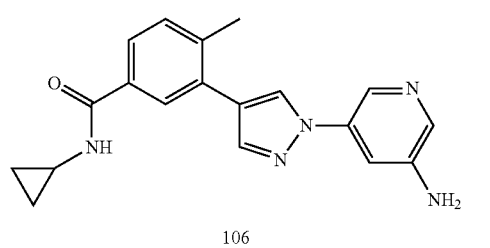

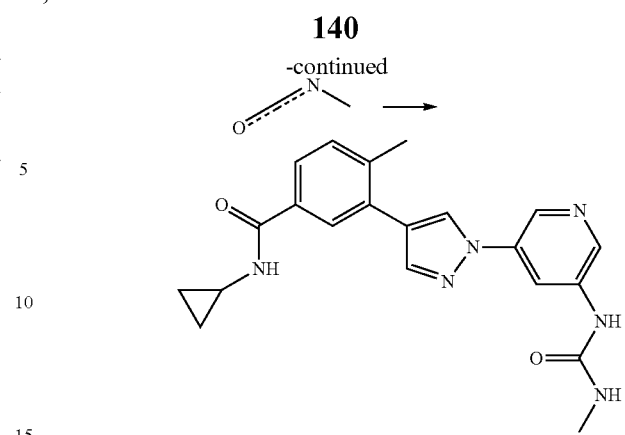

Aminopyridine 106 (0.050 g, 0.15 mmol) is dissolved in DMA (1 mL). To the solution is added methyl isocyanate (0.010 g, 0.18 mmol) and diisopropylethylamine (40.5 uL, 0.23 mmol). The reaction is shaken at 60° C. overnight.

The mixture is purified by reversed phase HPLC (mobile phase: ACN, H₂O with ammonium carbonate as base modifier) to afford 0.033 g of the title compound (107).

The following compounds are synthesized according to the Example 107 using commercially available isocyanate and/or intermediates described herein:

N-Cyclopropyl-3-{1-[5-(3-cyclopropyl-ureido)-pyridin-3-yl]-1H-pyrazol-4-yl}-4-methyl-benzamide (108)

3-{1-[5-(3-Cyclobutyl-ureido)-pyridin-3-yl]-1H-pyrazol-4-yl}-N-cyclopropyl-4-methyl-benzamide (109)

N-Cyclopropyl-3-{1-[5-(3-isopropyl-ureido)-pyridin-3-yl]-1H-pyrazol-4-yl}-4-methyl-benzamide (110)

Synthesis of 3-[1-(5-Acetylamino-pyridin-3-yl)-1H-pyrazol-4-yl]-N-cyclopropyl-4-methyl-benzamide (111)

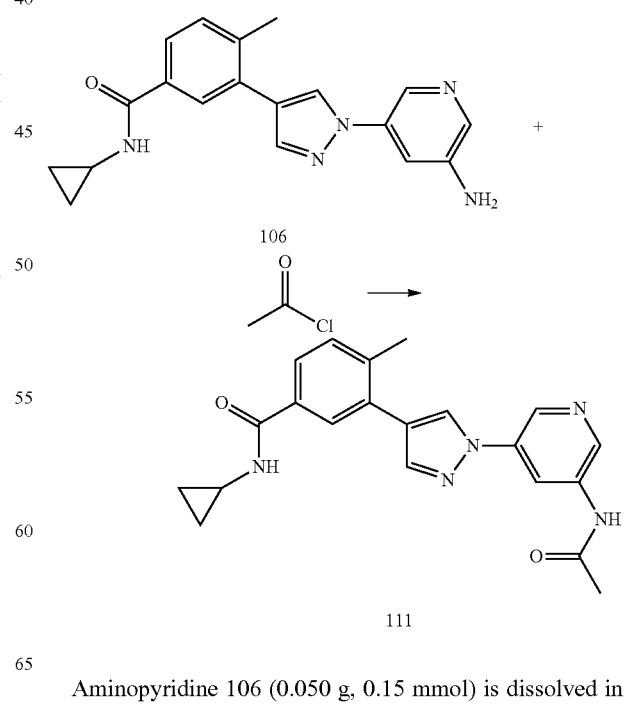

Aminopyridine 106 (0.050 g, 0.15 mmol) is dissolved in DMA (1 mL). To the solution is added acetyl chloride (0.014 mg, 0.18 mmol) and diisopropylethylamine (40.5 uL, 0.23 mmol). The reaction is shaken at room temperature overnight, then purified by reversed phase HPLC (mobile phase: ACN, H₂O with ammonium carbonate as base modifier) to afford 0.046 g of the title compound (111).

The following compounds are synthesized according to the Example 111 using commercially available acid chlorides and/or intermediates described herein:

N-Cyclopropyl-3-{1-[5-(2-methoxy-acetylamino)-pyridin-3-yl]-1H-pyrazol-4-yl}-4-methyl-benzamide (112)

N-Cyclopropyl-3-[1-(5-isobutyrylamino-pyridin-3-yl)-1H-pyrazol-4-yl]-4-methyl-benzamide (113)

N-Cyclopropyl-4-methyl-3-{1-[5-(3-methyl-butyrylamino)-pyridin-3-yl]-1H-pyrazol-4-yl}-benzamide (114)

3-{1-[5-(Cyclobutanecarbonyl-amino)-pyridin-3-yl]-1H-pyrazol-4-yl}-N-cyclopropyl-4-methyl-benzamide (115)

N-Cyclopropyl-3-{1-[5-(2-fluoro-acetylamino)-pyridin-3-yl]-1H-pyrazol-4-yl}-4-methyl-benzamide (116)

N-Cyclopropyl-4-methyl-3-[1-(5-propionylamino-pyridin-3-yl)-1H-pyrazol-4-yl]-benzamide (117)

N-Cyclopropyl-3-[1-(6-dimethylamino-pyrazin-2-yl)-1H-pyrazol-4-yl]-4-methyl-benzamide (118)

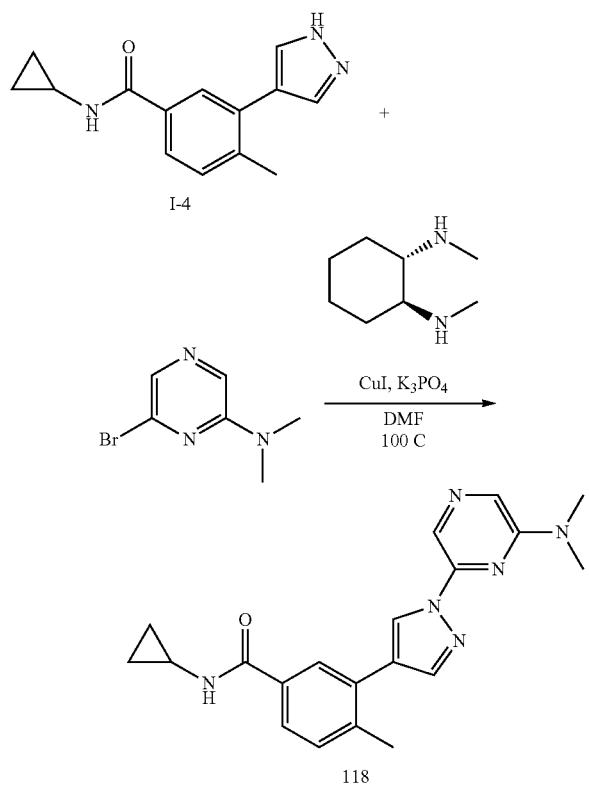

Pyrazole I-4 (0.075 g, 0.31 mmol), (6-bromo-pyrazin-2-yl)-dimethylamine (0.094 g, 0.47 mmol), copper iodide (0.024 g, 0.12 mmol) and potassium phosphate (0.013 g, 0.62 mmol) are combined in degassed DMF (1.5 mL). trans-1,2-Bis(methylamino)cyclohexane (0.039 mL, 0.25 mmol) is added and the suspension is heated at 100° C. After 18 h, water (0.15 mL) is added followed by 3 mL of a mixture of 10% water in DMF. The reaction is filtered and concentrated in vacuo. The resulting residue is purified by reversed phase HPLC (mobile phase: ACN, H₂O with ammonium carbonate as base modifier) which after evaporation of the eluent affords 0.038 g of the title compound (118).

The following compounds are synthesized according to the Example 118 using arylbromides from commercial sources or synthesized as described in US20140323468/WO2014179186A1:

N-Cyclopropyl-4-methyl-3-[1-(5-methyl-pyridin-3-yl)-1H-pyrazol-4-yl]-benzamide (119)

N-Cyclopropyl-3-{1-[5-(2,2-dimethyl-propionylamino)-pyridin-3-yl]-1H-pyrazol-4-yl}-4-methyl-benzamide (121)

N-Cyclopropyl-3-[1-(5-methanesulfonylamino-pyridin-3-yl)-1H-pyrazol-4-yl]-4-methyl-benzamide (122)

4-Chloro-N-cyclopropyl-5-[1-(6-dimethylamino-pyrazin-2-yl)-1H-pyrazol-4-yl]-2-fluoro-benzamide (123)

3-{1-[5-(1-Acetyl-azetidin-3-yloxy)-pyridin-3-yl]-1H-pyrazol-4-yl}-N-cyclopropyl-4-methyl-benzamide (124)

N-Cyclopropyl-4-methyl-3-{1-[5-((R)-1-methyl-5-oxo-pyrrolidin-2-yl)-pyridin-3-yl]-1H-pyrazol-4-yl}-benzamide (125)

3-{1-[5-((R)-1-Acetyl-pyrrolidin-3-yloxy)-pyridin-3-yl]-1H-pyrazol-4-yl}-N-cyclopropyl-4-methyl-benzamide (126)

N-Cyclopropyl-3-[1-(6-methoxy-pyrazin-2-yl)-1H-pyrazol-4-yl]-4-methyl-benzamide (127)

N-Cyclopropyl-4-methyl-3-{1-[6-(tetrahydro-pyran-4-yl)-pyrazin-2-yl]-1H-pyrazol-4-yl}-benzamide (128)

3-{1-[5-((S)-1-Acetyl-pyrrolidin-3-yloxy)-pyridin-3-yl]-1H-pyrazol-4-yl}-N-cyclopropyl-4-methyl-benzamide (129)

3-{1-[5-(1-Cyano-cyclopropyl)-pyridin-3-yl]-1H-pyrazol-4-yl}-N-cyclopropyl-4-methyl-benzamide (131)

N-Cyclopropyl-4-methyl-3-{1-[5-(3-oxo-morpholin-4-ylmethyl)-pyridin-3-yl]-1H-pyrazol-4-yl}-benzamide (135)

N-Cyclopropyl-3-(1-{5-[1-(1,1-dioxo-1lambda6-[1,2]thiazinan-2-yl)-ethyl]-pyridin-3-yl}-1H-pyrazol-4-yl)-4-methyl-benzamide (136)

N-Cyclopropyl-3-{1-[5-(4-hydroxy-tetrahydro-pyran-4-yl)-pyridin-3-yl]-1H-pyrazol-4-yl}-4-methyl-benzamide (137)

N-Cyclopropyl-3-{1-[5-(3-hydroxy-tetrahydro-furan-3-yl)-pyridin-3-yl]-1H-pyrazol-4-yl}-4-methyl-benzamide (138)

N-Cyclopropyl-4-methyl-3-(1-{5-[1-(2-oxo-pyrrolidin-1-yl)-ethyl]-pyridin-3-yl}-1H-pyrazol-4-yl)-benzamide (140)

N-Cyclopropyl-4-methyl-3-[1-(5-methylamino-pyridin-3-yl)-1H-pyrazol-4-yl]-benzamide (141)

N-Cyclopropyl-4-methyl-3-(1-{5-[3-(tetrahydro-furan-3-yl)-ureido]-pyridin-3-yl}-1H-pyrazol-4-yl)-benzamide (142)

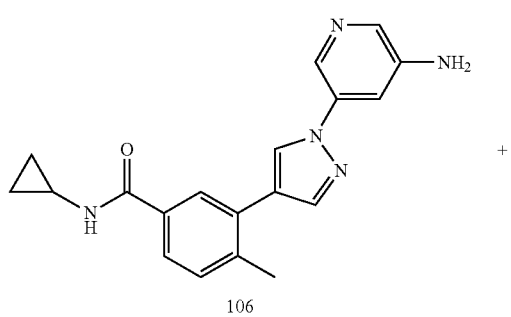

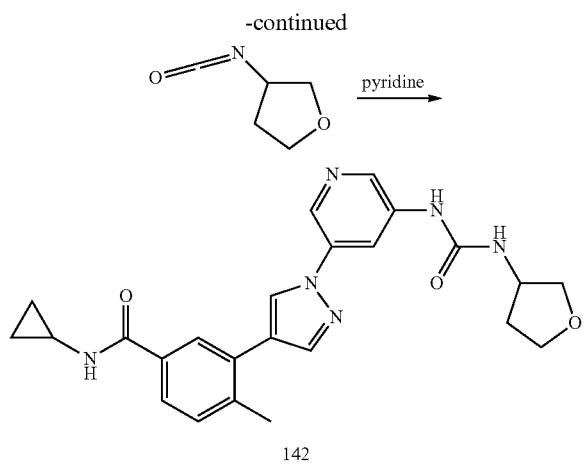

142

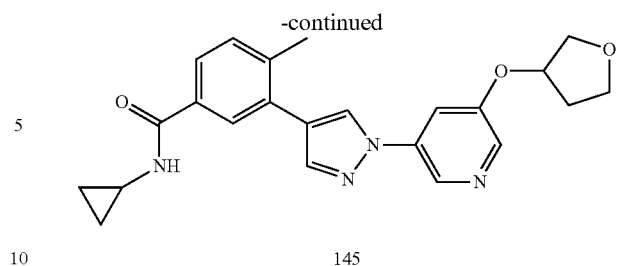

145

To aminopyridine 106 (0.050 g, 0.15 mmol) is added dichloromethane (1 mL), pyridine (18 □L, 0.23 mmol) and then 3-isocyanato-tetrahydro-furan (0.020 g, 0.18 mmol) and the reaction is shaken at room temp for 96 h. An additional portion of pyridine (18 uL, 0.23 mmol) and 3-isocyanato-tetrahydro-furan (0.020 g, 0.18 mmol) are added and shaking is continued for 16 hours. Water (0.2 mL) is added and the reaction is concentrated under reduced pressure. The residue is dissolved in 2 mL of a mixture of 10% water in DMSO and purified by reversed phase HPLC (mobile phase: ACN, $H_2O$ with ammonium carbonate as base modifier) which after evaporation of the eluent affords 0.013 g of the title compound (142).

The following compounds are synthesized according to the Example 142 using commercial acid chlorides:

N-Cyclopropyl-3-{1-[5-(3-methoxy-propionylamino)-pyridin-3-yl]-1H-pyrazol-4-yl}-4-methyl-benzamide (143)

3-{1-[5-(Cyclopropanecarbonyl-amino)-pyridin-3-yl]-1H-pyrazol-4-yl}-N-cyclopropyl-4-methyl-benzamide (144)

Example 30

N-Cyclopropyl-4-methyl-3-{1-[5-(tetrahydro-furan-3-yloxy)-pyridin-3-yl]-1H-pyrazol-4-yl}-benzamide (145)

To tetrahydro-furan-3-ol (18 uL, 0.22 mmol) is added a solution of phenol 95 (0.050 g, 0.15 mmol) in DMF (0.4 mL), followed by a solution of diphenyl-2-pyridylphosphine (0.094 g, 0.36 mmol) in DMF (0.4 mL) and a solution of di-tert-butyl azodicarboxylate (0.083 g, 0.36 mmol) in DMF (0.4 mL). The mixture is shaken at room temperature for 16 h, then an additional portion of tetrahydro-furan-3-ol (18 uL, 0.22 mmol) is added followed by additional diphenyl-2-pyridylphosphine (0.094 g, 0.36 mmol) and di-tert-butyl azodicarboxylate (0.083 g, 0.36 mmol). The reaction is shaken for 16 hours then filtered through a SiTHIOL cartridge (3 mL cartridge containing 500 mg sorbent). The cartridge is eluted with dioxane (2×2 mL) and the combined eluents are concentrated under reduced pressure. The residue is dissolved in MeOH (5 mL) and purified by reversed phase HPLC (mobile phase: ACN, $H_2O$ with ammonium carbonate as base modifier) which after evaporation of the eluent affords 0.021 g of the title compound (145).

The following compounds are synthesized according to the Example 145 using commercial alcohols:

N-Cyclopropyl-3-[1-(5-cyclopropylmethoxy-pyridin-3-yl)-1H-pyrazol-4-yl]-4-methyl-benzamide (146)

N-Cyclopropyl-4-methyl-3-{1-[5-(tetrahydro-pyran-4-yl-methoxy)-pyridin-3-yl]-1H-pyrazol-4-yl}-benzamide (147)

3-[1-(5-Cyclopentyloxy-pyridin-3-yl)-1H-pyrazol-4-yl]-N-cyclopropyl-4-methyl-benzamide (148)

3-{1-[5-(1-Acetyl-piperidin-4-yloxy)-pyridin-3-yl]-1H-pyrazol-4-yl}-N-cyclopropyl-4-methyl-benzamide (149)

N-Cyclopropyl-4-methyl-3-(1-{5-[(R)-1-(tetrahydro-furan-2-yl)methoxy]-pyridin-3-yl}-1H-pyrazol-4-yl)-benzamide (150)

3-{1-[5-(3-Cyano-cyclopentyloxy)-pyridin-3-yl]-1H-pyrazol-4-yl}-N-cyclopropyl-4-methyl-benzamide (151)

3-{1-[5-(3,3-Bis-hydroxymethyl-cyclobutoxy)-pyridin-3-yl]-1H-pyrazol-4-yl}-N-cyclopropyl-4-methyl-benzamide (152)

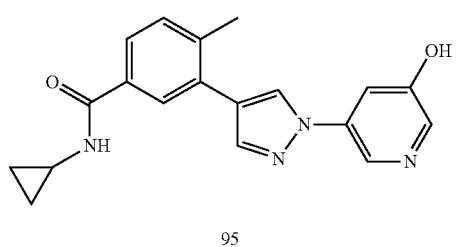

95

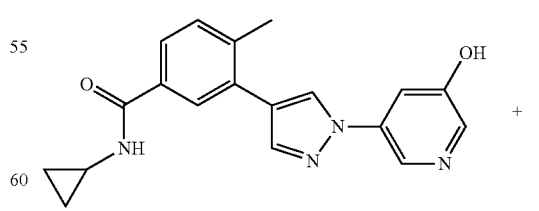

95

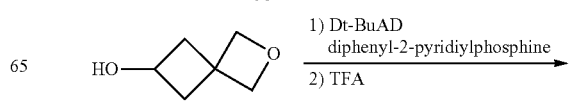

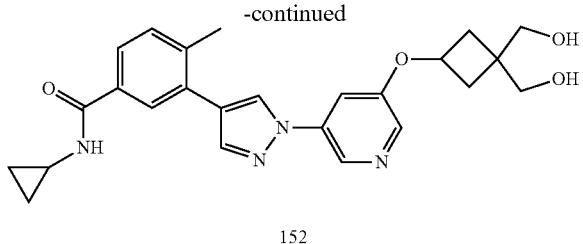

152

To 2-oxa-spiro[3.3]heptan-6-ol (0.034 g, 0.3 mmol) is added a solution of phenol 95 (0.050 g, 0.15 mmol) in DMF (0.4 mL), followed by a solution of diphenyl-2-pyridylphosphine (0.094 g, 0.36 mmol) in DMF (0.4 mL) and a solution of di-tert-butyl azodicarboxylate (Dt-BuAD) (0.083 g, 0.36 mmol) in DMF (0.4 mL). The yellow solution is shaken at room temp for 16 hours, then an additional portion of 2-oxa-spiro[3.3]heptan-6-ol (0.034 g, 0.3 mmol) is added followed by solid Dt-BuAD (0.094 g, 0.36 mmol) and solid di-tert-butyl azodicarboxylate (0.083 g, 0.36 mmol). The reaction is shaken at room temp for 60 hours then trifluoroacetic acid (0.25 mL) is added and the reaction is concentrated under reduced pressure. The residue is dissolved in mixture of 9:1 DMSO/water (1.5 mL) and purified by reversed phase HPLC (mobile phase: ACN, H$_2$O with ammonium carbonate as base modifier) which after evaporation of the eluent affords 0.006 g of the title compound (152).

N-Cyclopropyl-3-(1-{5-[1-(3-hydroxy-1-methyl-propyl)-piperidin-4-ylamino]-pyridin-3-yl}-1H-pyrazol-4-yl)-4-methyl-benzamide (153)

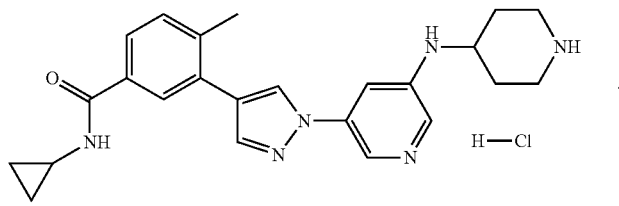 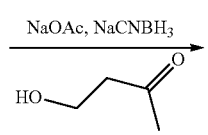

To 4-hydroxy-butan-2-one (0.048 g, 0.55 mmol) is added sodium acetate (0.034 g, 0.44 mmol), followed by a solution of 92 (0.050 g, 0.11 mmol) in MeOH (1 mL). The suspension is shaken at room temperature for 60 minutes then a solution of sodium cyanoborohydride (0.032 g, 0.55 mmol) in MeOH (0.5 mL) is added. The solution is shaken at room temperature for 16 hours. The reaction is quenched by addition of 0.2 mL water and concentrated under reduced pressure. The residue is dissolved in 2 mL of a 9:1 mixture of DMSO/water and purified by reversed phase HPLC (ACN, H2O with ammonium carbonate as base modifier) to yield after evaporation of the eluent 0.020 g of the title compound (153).

The following compounds are synthesized according to Example 153 using commercially available ketones or aldehydes:

N-Cyclopropyl-4-methyl-3-(1-{5-[1-(tetrahydro-furan-3-ylmethyl)-piperidin-4-ylamino]-pyridin-3-yl}-1H-pyrazol-4-yl)-benzamide (154)

N-Cyclopropyl-4-methyl-3-(1-{5-[1-(tetrahydro-pyran-4-ylmethyl)-piperidin-4-ylamino]-pyridin-3-yl}-1H-pyrazol-4-yl)-benzamide (155)

N-Cyclopropyl-3-(1-{5-[1-(2-methoxy-1-methyl-ethyl)-piperidin-4-ylamino]-pyridin-3-yl}-1H-pyrazol-4-yl)-4-methyl-benzamide (156)

N-Cyclopropyl-3-(1-{5-[1-(2-hydroxy-1-methyl-ethyl)-piperidin-4-ylamino]-pyridin-3-yl}-1H-pyrazol-4-yl)-4-methyl-benzamide (157)

3-{1-[5-(1'-Acetyl-[1,4']bipiperidinyl-4-ylamino)-pyridin-3-yl]-1H-pyrazol-4-yl}-N-cyclopropyl-4-methyl-benzamide (158)

N-Cyclopropyl-4-methyl-3-(1-{5-[1-(2-methyl-tetrahydro-furan-3-yl)-piperidin-4-ylamino]-pyridin-3-yl}-1H-pyrazol-4-yl)-benzamide (159)

N-Cyclopropyl-3-(1-{5-[1-(4-methoxy-cyclohexyl)-piperidin-4-ylamino]-pyridin-3-yl}-1H-pyrazol-4-yl)-4-methyl-benzamide (160)

N-Cyclopropyl-4-methyl-3-(1-{5-[1-(tetrahydro-pyran-3-yl)-piperidin-4-ylamino]-pyridin-3-yl}-1H-pyrazol-4-yl)-benzamide (161)

N-Cyclopropyl-4-methyl-3-(1-{5-[1-(tetrahydro-pyran-4-yl)-piperidin-4-ylamino]-pyridin-3-yl}-1H-pyrazol-4-yl)-benzamide (162)

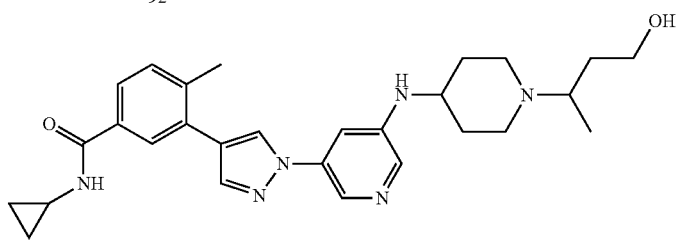

153

N-Cyclopropyl-3-(1-{5-[1-(3-methoxy-tetrahydro-pyran-4-yl)-piperidin-4-ylamino]-pyridin-3-yl}-1H-pyrazol-4-yl)-4-methyl-benzamide (163)

N-Cyclopropyl-4-methyl-3-(1-{5-[1-(3-methyl-tetrahydro-pyran-4-yl)-piperidin-4-ylamino]-pyridin-3-yl}-1H-pyrazol-4-yl)-benzamide (164)

N-Cyclopropyl-4-methyl-3-(1-{5-[1-(2-methyl-tetrahydro-pyran-4-yl)-piperidin-4-ylamino]-pyridin-3-yl}-1H-pyrazol-4-yl)-benzamide (165)

N-Cyclopropyl-4-methyl-3-(1-{5-[1-(tetrahydro-furan-3-yl)-piperidin-4-ylamino]-pyridin-3-yl}-1H-pyrazol-4-yl)-benzamide (166)

N-Cyclopropyl-4-methyl-3-(1-{5-[1-(3-oxa-bicyclo[3.1.0]hex-6-ylmethyl)-piperidin-4-ylamino]-pyridin-3-yl}-1H-pyrazol-4-yl)-benzamide (167)

N-Cyclopropyl-3-{1-[5-(1-[1,4]dioxan-2-ylmethyl-piperidin-4-ylamino)-pyridin-3-yl]-1H-pyrazol-4-yl}-4-methyl-benzamide (168).

N-Cyclopropyl-2-fluoro-5-[1(5-{(3R,4S)-3-fluoro-1-methylpiperidin-4-yl]amino}pyridine-3-yl)-1H-pyrazol-4-yl]-4-methylbenzamide (169)

Tert-Butyl (3R,4S)-4-[(5-{4-[5-(cyclopropylcarbamoyl)-4-fuoro-2-methylphenyl]-1H-pyrazol-1-yl}pyridine-3-yl)amino]-3-fluoropiperidine-1-carboxylate (0.32 g, 0.59 mmol) was dissolved in DCM (10 mL) and to this was added 4.0M HCl in dioxane (1.0 mL, 4.0 mmol) and the reaction was allowed to stir at RT for 4 h. The mixture was concentrated to give crude N-cyclopropyl-2-fluoro-5-[1(5-{(3R,4S)-3-fluoropiperidin-4-yl]amino}pyridine-3-yl)-1H-pyrazol-4-yl]-4-methylbenzamide dihyrdrochloride (0.34 g, 0.64 mmol) which was used without further purification.

N-cyclopropyl-2-fluoro-5-[1(5-{(3R,4S)-3-fluoropiperidin-4-yl]amino}pyridine-3-yl)-1H-pyrazol-4-yl]-4-methylbenzamide dihyrdrochloride (0.34 g, 0.64 mmol) was dis-

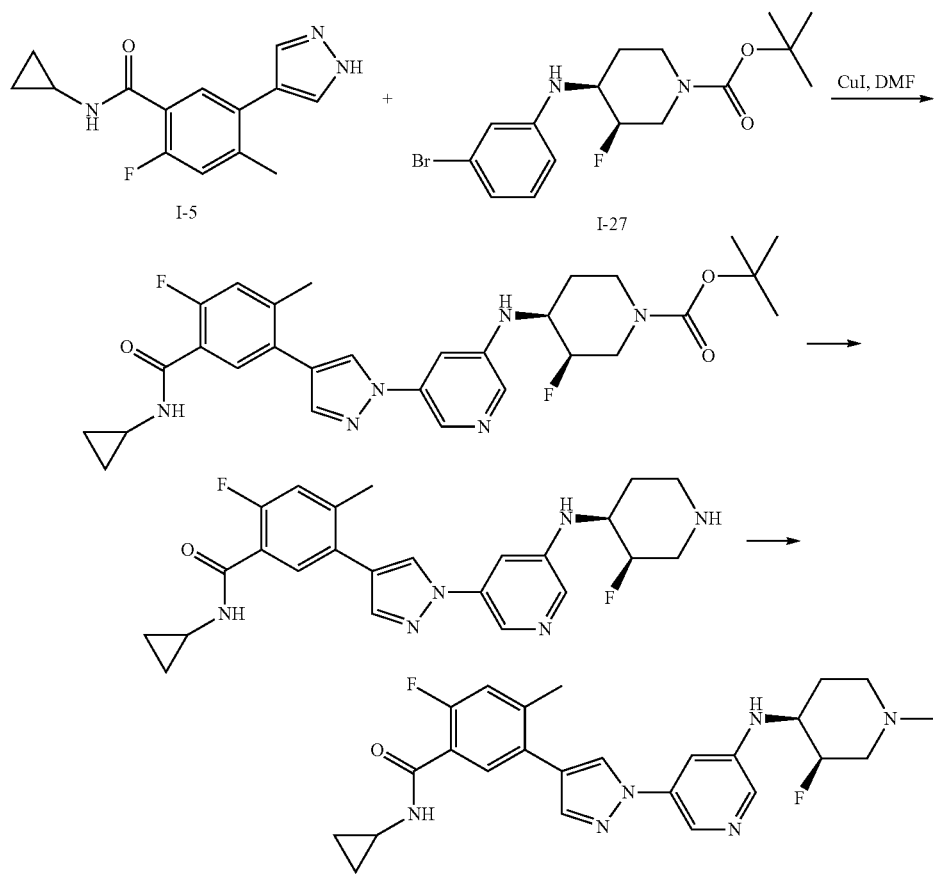

Potassium phosphate tribasic (0.38 g, 1.8 mmol) was dissolved in DMF (5.0 mL) and to this was added I-27 (0.33 g, 0.89 mmol), I-5 (0.25 g, 0.99 mmol) and CuI (0.068 g, 0.36 mmol). The reaction was mixture was purged with $N_2$ and then trans-dimethylcyclohexyldiamine (112 µL, 0.72 mmol) was added and Ar bubbled over the mixture for 10 min. The reaction vessel was capped and heated at 100° C. for 14 h. The mixture was cooled to RT and filtered through a plug of celite with EtOAc washing. The mixture was concentrated and purified by silica gel chromatography (0-100% EtOAc in heptanes). The resulting material was purified by HPLC to give tert-butyl (3R,4S)-4-[(5-{4-[5-(cyclopropylcarbamoyl)-4-fuoro-2-methylphenyl]-1H-pyrazol-1-yl}pyridine-3-yl)amino]-3-fluoropiperidine-1-carboxylate (0.33 g, 0.60 mmol).

solved in MeOH (6.0 mL) and to this was added formaldehyde (37% wt in water, 0.21 mL, 2.9 mmol) and anhydrous sodium acetate (0.16 g, 1.9 mmol) with bubbling observed. The reaction was allowed to stir for 90 min at RT. Sodium cyanoborohydride (0.18 g, 2.6 mmol) was then added with bubbling observed and the reaction mixture stirred for 1 h. The mixture was concentrated and purified by prep-HPLC ($NH_4HCO_3$ buffer, 5-90% MeCN/water as gradient). The combined fractions were concentrated and purified again by silica gel chromatography (0-100% EtOAc in heptanes then 0-10% MeOH in DCM) give 169 as a white solid (0.078 g, 0.17 mmol).

The following compound synthesized according to Example 169 using I-28 as opposed to I-27:

149

N-Cyclopropyl-2-fluoro-5-[1(5-{(3S,4R)-3-fluoro-1-methylpiperidin-4-yl]amino}pyridine-3-yl)-1H-pyrazol-4-yl]-4-methylbenzamide (170)

N-Cyclopropyl-5-[1-(4-dimethylamino-3,4,5,6-tetrahydro-2H-[1,3"]bipyridinyl-5"-yl)-1H-pyrazol-4-yl]-2-fluoro-4-methyl-benzamide (171)

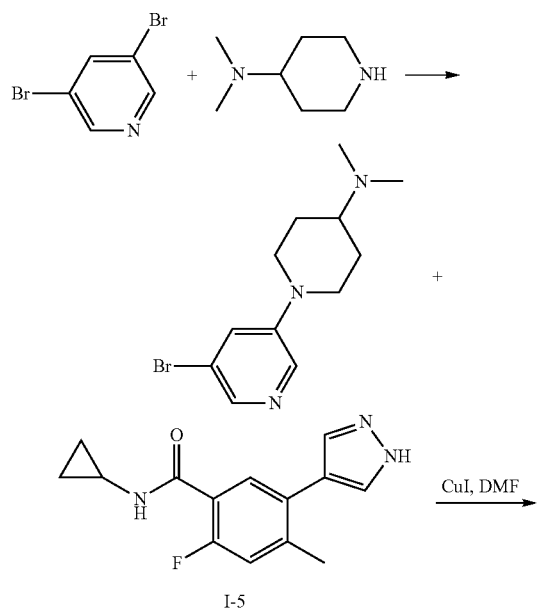

150 cooled to RT, filtered and purified directly by prep-HPLC to give 171 (0.026 g, 0.056 mmol).

N-Cyclopropyl-2-fluoro-4-methyl-5-{1-[5-((S)-1-methyl-pyrrolidin-3-ylmethoxy)-pyridin-3-yl]-1H-pyrazol-4-yl}-benzamide (172)

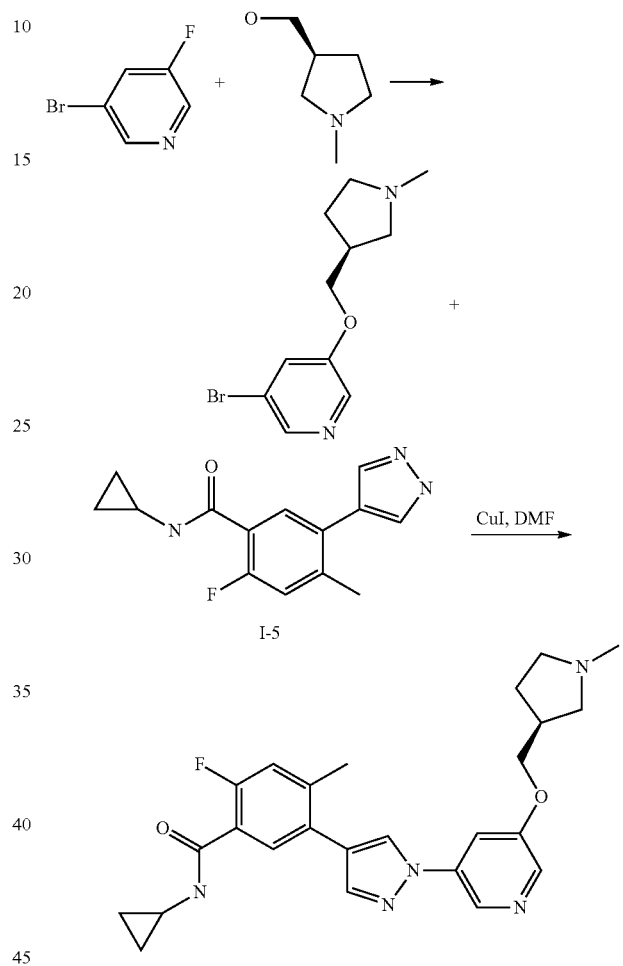

Dimethyl-piperidin-4-yl-amine (2.0 g, 16.0 mmol) is dissolved in toluene (20 mL) and to this is added 2,5-dibromopyridine (4.6 g, 19.5 mmol) sodium tert-butoxide (3.0 g, 31.2 mmol) Pd$_2$(dba)$_3$ (0.57 g, 0.62 mmol) and BINAP (1.2 g, 1.9 mmol) and the mixture purged with Argon. The reaction is heated at 100° C. for 16 h. The mixture is cooled to RT, filtered through celite and washed with MeOH. The filtrated is concentrated and redissolved in DCM (100 mL). To this is added 1N HCl (2×100 mL) and the organic layer separated. The Aq layer is collected and neutralized with base. The aq layer is extracted with DCM (3×100 mL) and the mixture concentrated to give (5'-Bromo-3,4,5,6-tetrahydro-2H-[1,3']bipyridinyl-4-yl)-dimethyl-amine (1.4 g, 5.0 mmol) which is used without further purification.

(5'-Bromo-3,4,5,6-tetrahydro-2H-[1,3']bipyridinyl-4-yl)-dimethyl-amine (0.22 g, 0.75 mmol), I-5 (0.20 g, 0.75 mmol), CuI (0.059 g, 0.31 mmol), potassium phosphate tribasic (0.33 g, 1.5 mmol) trans-1,2-bis(methylamino)cyclohexane (0.097 mL, 0.62 mmol) are dissolved in DMF (3.0 mL) and heated at 80° C. overnight. The mixture is cooled to RT, filtered and purified directly by prep-HPLC to give 171 (0.026 g, 0.056 mmol).

NaH (0.2 g, 5.0 mmol) is suspended in DMF (3 mL) and cooled in an ice bath. To this is slowly added (S)-3-(Hydroxymethyl)-1-methylpyrrolidine (0.48 g, 4.2 mmol) and the mixture stirred for 15 min. 3-bromo-5-fluoropyridine (0.92 g, 5.2 mmol) is then added and the mixture allowed to stir at RT overnight. The mixture is quenched with water, diluted with EtOAc, washed with satd NaHCO$_3$. The water layer is back extracted with EtOAc (2×20 mL) and the combined organics are dried with sodium sulfate, filtered and concentrated to give the crude product which is purified by silica gel chromatography (0-10% MeOH in DCM) give 5-Bromo-5((S)-1-methyl-pyrrolidin-3-ylmethoxy)-pyridine (0.78 g, 2.9 mmol).

5-Bromo-5((S)-1-methyl-pyrrolidin-3-ylmethoxy)-pyridine (0.16 g, 0.58 mmol), I-5 (0.10 g, 0.38 mmol), CuI (0.029 g, 0.15 mmol), potassium phosphate tribasic (0.25 g, 1.1 mmol) trans-1,2-bis(methylamino)cyclohexane (0.049 mL, 0.31 mmol) are dissolved in DMF (2.0 mL) and heated at 90° C. overnight. The mixture is cooled to RT, filtered and purified directly by prep-HPLC to give 172 (0.11 g, 0.25 mmol).

4-Chloro-N-cyclopropyl-2-fluoro-5-{1-[5-((3R,4S)-3-methoxy-1-methyl-piperidin-4-ylamino)-pyridin-3-yl]-1H-pyrazol-4-yl}-benzamide (173)

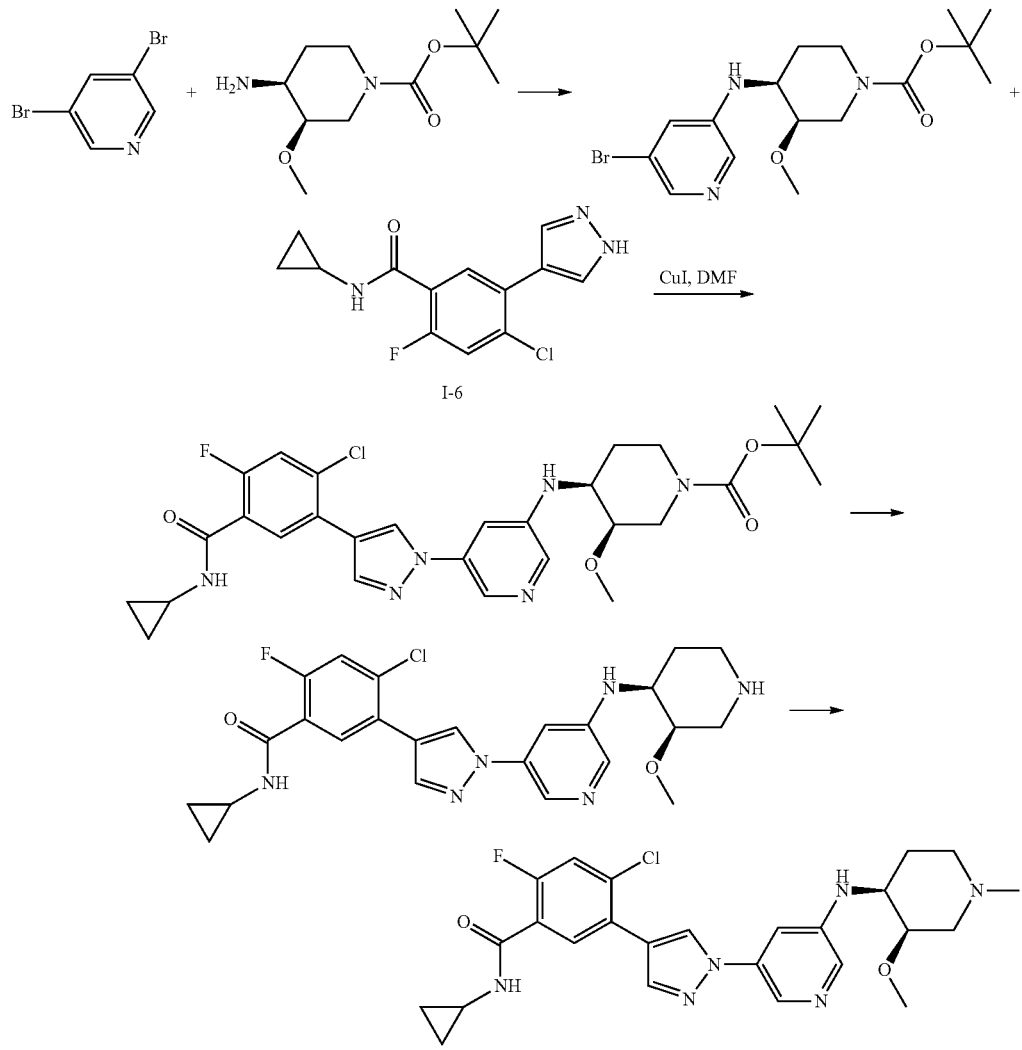

To (3R,4S)-4-amino-1-Boc-3-methoxypiperidine (5.0 g, 21.7 mmol) in a pressure flask is added 3,5-dibromopyridine (9.2 g, 39.0 mmol), sodium tert-butoxide (3.1 g, 33 mol), Pd$_2$(dpa)$_3$ (0.80 g, 0.87 mmol), rac-BINAP (1.6 g, 2.6 mmol) and toluene (60 mL) and degassed with argon. The mixture is heated at 120° C. for 3 h. The mixture is cooled to RT, filtered through celite and the filtrate concentrated to give the crude product which is purified by silica-gel chromatography (0-65% EtOAc in heptanes) to give (3R,4S)-4-(5-Bromo-pyridin-3-ylamino)-3-methoxy-piperidine-1-carboxylic acid tert-butyl ester (5.3 g, 13.7 mmol).

(3R,4S)-4-(5-Bromo-pyridin-3-ylamino)-3-methoxy-piperidine-1-carboxylic acid tert-butyl ester (2.1 g, 15.4 mmol)), I-6 (1.6 g, 6.0 mmol), CuI (0.41 g, 0.22 mmol), potassium phosphate tribasic (3.4 g, 16.3 mmol) trans-1,2-bis(methylamino)cyclohexane (0.67 mL, 0.4.3 mmol) are dissolved in DMF (20.0 mL) and heated at 100° C. overnight. The mixture is cooled to RT, filtered through celite with EtOAc washing. The filtrated is washed with water, brine and the organic layer concentrated. The crude product is purified by silica-gel chromatography (0-5% MeOH in DCM) to give (3R,4S)-4-{5-[4-(2-Chloro-5-cyclopropylcarbamoyl-4-fluoro-phenyl)-pyrazol-1-yl]-pyridin-3-ylamino}-3-methoxy-piperidine-1-carboxylic acid tert-butyl ester (2.0 g, 3.4 mmol).

(3R,4S)-4-{5-[4-(2-Chloro-5-cyclopropylcarbamoyl-4-fluoro-phenyl)-pyrazol-1-yl]-pyridin-3-ylamino}-3-methoxy-piperidine-1-carboxylic acid tert-butyl ester (2.0 g, 3.4 mmol) is dissolved in DCM (20 mL) and MeOH (10 mL). To this is added 4N HCL in dioxane (15 mL) and the mixture stirred at RT overnight. The mixture is concentrated to give 4-Chloro-N-cyclopropyl-2-fluoro-5-{1-[5-(3R,4S)-3-methoxy-piperidin-4-ylamino)-pyridin-3-yl]-1H-pyrazol-4-yl}-benzamide hydrochloride (1.5 g, 2.9 mmol).

4-Chloro-N-cyclopropyl-2-fluoro-5-{1-[5-(3R,4S)-3-methoxy-piperidin-4-ylamino)-pyridin-3-yl]-1H-pyrazol-4- yl}-benzamide hydrochloride (0.21 g, 0.40 mmol) is dissolved in DCE (4 mL) and MeOH (1 mL) and to this is added sodium acetate (0.16 g, 2.0 mmol) and formaldehyde (37% wt in water, 0.15 mL, 2.0 mmol) and the mixture stirred for 10 min. To this is added sodium bis(acetyloxy) boranuidyl acetate (0.43 g, 2.0 mmol) and the mixture stirred for 20 min. The mixture is concentrated and the residue partitioned between EtOAc and satd NaHCO₃. The organic layer was separated, dried, filtered and concentrated to give the crude product which was purified by silica-gel chromatography (0-15% MeOH in DCM) to give 173.

N-Cyclopropyl-2-fluoro-5-(1-{5-[1-(2-fluoro-ethyl)-piperidin-4-ylamino]-pyridin-3-yl}-1H-pyrazol-4-yl)-4-methyl-benzamide (174)

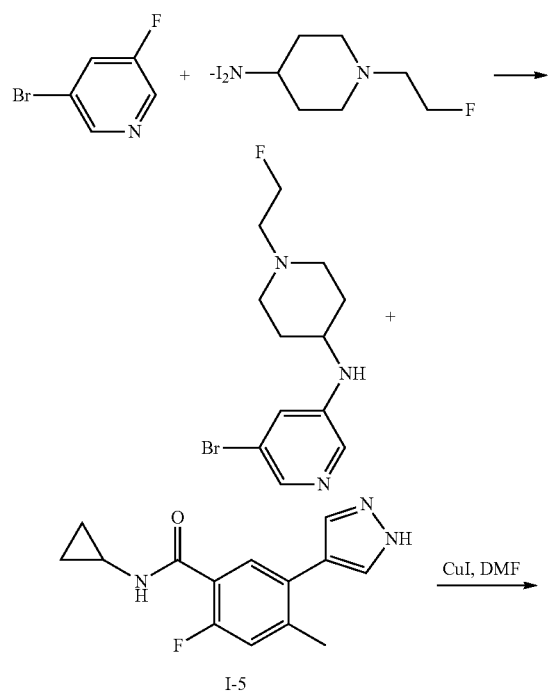

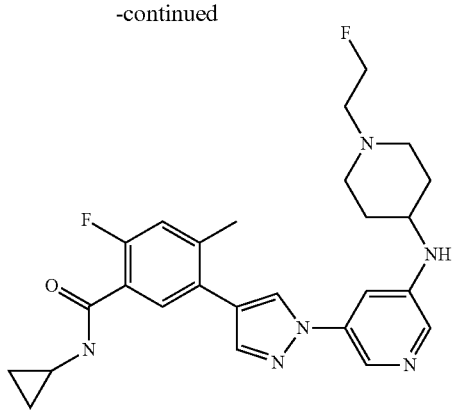

3-Bromo-5-fluoropyridine (0.5 g, 2.8 mmol) is dissolved in DMA (0.5 mL) and to this is added 1-(2-fluoro-ehtyl)-piperidin-4yl-amine dihyrdochloride (0.93 g, 4.3 mmol) and potassium carbonate (1.2 g, 8.5 mmol) and heated at 130° C. for 65 h. The mixture is cooled to RT and purified by prep-HPLC to give (5-Bromo-pyridin-3-yl)-[1-(2-fluoro-ethyl)-piperidin-4-yl]-amine (0.074 g, 0.25 mmol).

(5-Bromo-pyridin-3-yl)-[1-(2-fluoro-ethyl)-piperidin-4-yl]-amine (0.074 g, 0.25 mmol), I-5 (0.13 g, 0.43 mmol), CuI (0.022 g, 0.12 mmol), potassium phosphate tribasic (0.13 g, 0.6 mmol) trans-1,2-bis(methylamino)cyclohexane (0.037 mL, 0.24 mmol) are dissolved in DMF (1.0 mL) and heated at 90° C. overnight. The mixture is cooled to RT, filtered and purified directly by prep-HPLC to give 174 (0.024 g, 0.050 mmol).

N-Cyclopropyl-5-{1-[5-((S)-3,3-difluoro-1-methyl-piperidin-4-ylamino)-pyridin-3-yl]-1H-pyrazol-4-yl}-2-fluoro-4-methyl-benzamide (175) and N-Cyclopropyl-5-{1-[5-((R)-3,3-difluoro-1-methyl-piperidin-4-ylamino)-pyridin-3-yl]-1H-pyrazol-4-yl}-2-fluoro-4-methyl-benzamide (176)

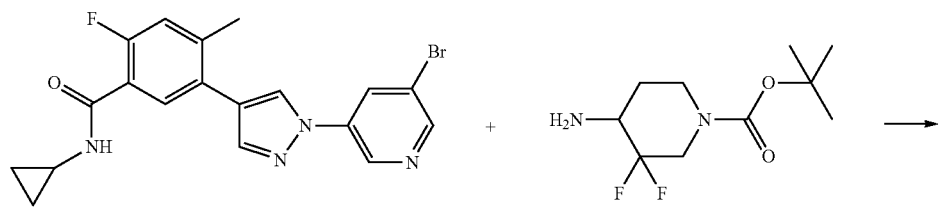

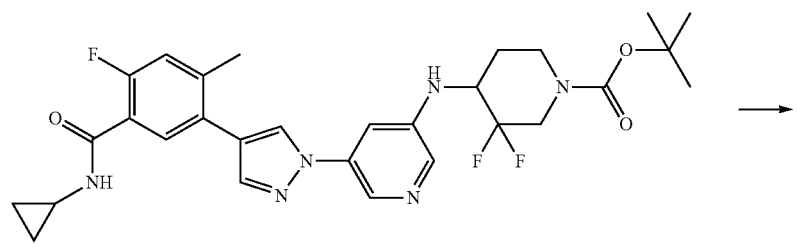

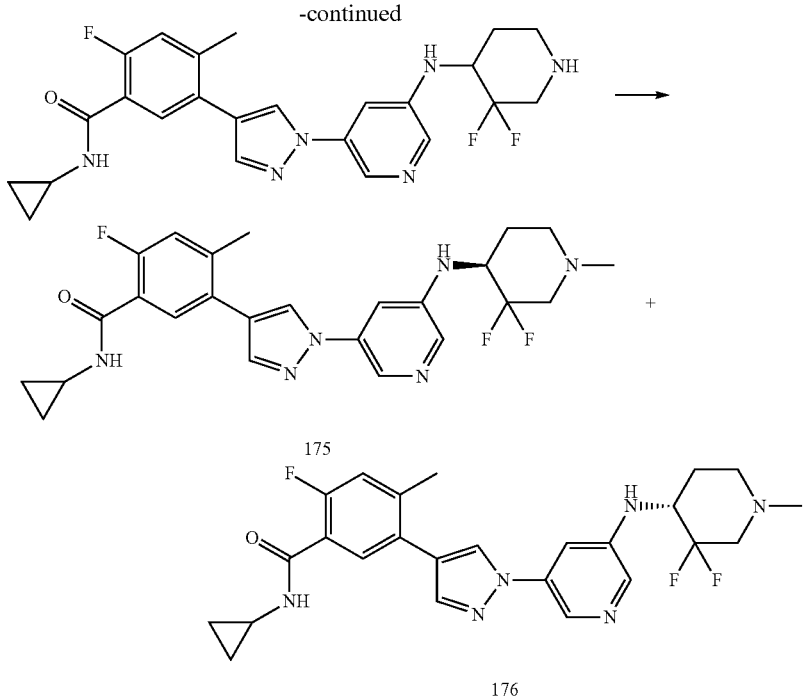

175

176

I-20b (0.30 g, 0.72 mmol) is dissolved in dioxane (2.0 mL) and to this is added 4-amino-3,3-difluoro-piperidine-1-carboxyic acid tert-butyl ester (0.19 g, 0.80 mmol), sodium phenoxide (0.18 g, 1.6 mmol) 5-[Di(1-adamantyl)phosphine]-1',3',5'-triphenyl-1'H-[1,4']bipyrazole (0.019 g, 0.029 mmol) and allyl palladium chloride dimer (0.005 g, 0.014 mmol) and the mixture heated at 110° C. for 2 h. The mixture is cooled to RT and filtered through celite with EtOAc washing. The filtrate is concentrated and purified by silica-gel chromatography (0-8% MeOH in DCM) to give 4-{5-[4-(5-Cyclopropylcarbamoyl-4-fluoro-2-methyl-phenyl)-pyrazol-1-yl]-pyridin-3-ylamino}-3,3-difluoro-piperidine-1-carboxylic acid tert-butyl ester (0.33 g, 0.58 mmol).

4-{5-[4-(5-Cyclopropylcarbamoyl-4-fluoro-2-methyl-phenyl)-pyrazol-1-yl]-pyridin-3-ylamino}-3,3-difluoro-piperidine-1-carboxylic acid tert-butyl ester (0.50 g, 0.88 mmol) is dissolved in DCM (8 mL) and to this is added 4N HCl in dioxane (2.1 mL, 8.76 mmol) and the mixture stirred at RT overnight. The solvent is evaporated to give N-Cyclopropyl-5-{1-[5-(3,3-difluoro-piperidin-4-ylamino)-pyridin-3-yl]-1H-pyrazol-4-yl}-2-fluoro-4-methyl-benzamide hydrochloride (0.49 g, 0.87 mmol) which is used without further purification.

N-Cyclopropyl-5-{1-[5-(3,3-difluoro-piperidin-4-ylamino)-pyridin-3-yl]-1H-pyrazol-4-yl}-2-fluoro-4-methyl-benzamide hydrochloride (0.20 g, 0.36 mmol) is dissolved in MeOH (3.5 mL) and to this is added formaldehyde (37% wt in water, 0.2 mL, 2.7 mmol) and sodium acetate (0.15 g, 1.8 mmol) and the mixture stirred for 90 min. To this is added sodium cyanoborohydride (0.17 g, 2.7 mmol) and the reaction allowed to stir for 3 h. The mixture is diluted with DMF and water and purified by prep-HPLC. The racemic product is then purified by chiral-prep HPLC to give 175 and 176 where the stereochemistry has been arbitrarily assigned.

HPLC and MS Data for compounds in Table 1 are shown in Table 3, which are measured using the methods set forth in the following Table 2.

TABLE 2

HPLC Method

| Method | Mobile Phase A | Mobile Phase B | Gradient | | | Flow (mL/min.) | Column |
| | | | Time (min) | % A | % B | | |
|---|---|---|---|---|---|---|---|
| A | 0.1% Formic Acid in Water | 0.1% Formic Acid in ACN | 0 | 95.0 | 5.0 | 0.8 | BEH 2.5 × 50 mm C18, 1.7 μm particle diameter |
| | | | 1.0 | 5.0 | 95.0 | | |
| | | | 1.3 | 5.0 | 95.0 | | |
| | | | 1.4 | 95.0 | 5.0 | | |
| | | | 1.7 | 95.0 | 5.0 | | |

Assessment of Biological Properties

RIPK2 inhibition for compounds in Table 1 are shown in Table 3 and measured using the following method:

Materials: White, 384-well optiplates (cat.no. 6007290) were purchased from PerkinElmer. The V9103X ADP-Glo Kinase Assay Custom (including ultra-pure ATP) was purchased from Promega. 8His-RIPK2 FL was prepared in-house. All other materials were of highest grade commercially available.

Method: In a 384-well plate, test compound diluted in assay buffer (1% DMSO final) is mixed with 8His-RIPK2 FL enzyme (final concentration of 8 nM). After 15 minutes of pre-incubation at RT, ATP dissolved in assay buffer is added (final concentration 5 μM). The mixture is incubated for 60 minutes at 37° C. in a humidified incubator. Then, ADP Glo Reagent is added, followed by a 40 minute incubation at rt. Finally, Kinase Detection Reagent is added and the entire mixture is incubated for 40 min at RT. The luminescence signal is measured with an Envision reader to determine the amount of ADP produced. Assay buffer: 25 mM HEPES (4-(2-hydroxyethyl)-1-piperazinethanesulfonic acid), 0.1% BSA (bovine serum albumin), 10 mM MgCl2, 5 mM MnCl2, 50 mM KCl, 0.01% CHAPS (3-[(3-cholamidopropyl)dimethylammonio]-1-propanesulfonate), 10 μM Na3VO4, 1 mM DTT (dithiothreitol), pH 7.5 All plates contain wells with vehicle controls instead of compound (1% DMSO) as reference for the high signal (100% CTL (100% of control), high signal), and wells without enzyme as reference for low signal (0% CTL, low signal). The luminescent signal generated is proportional to the ADP produced and is correlated with enzyme activity. The analysis of the data is performed by the calculation of the percentage of ADP production in the presence of the test compound and RIPK2 as compared to the ADP production in the presence of RIPK2 plus 50 μM Gefitinib. (RLU (relative luminescence units) (sample)−RLU(low control))*100/(RLU(high value)−RLU(low control)) [RLU=relative luminescence units].

TABLE 3

| Example | RIPK2 IC$_{50}$ (nM) | m/z | rt (min) |
|---|---|---|---|
| 25 | 3.7 | 366.1 | 0.77 |
| 26 | 8.9 | 386.1 | 0.81 |
| 27 | 22 | 368.1 | 0.77 |
| 28 | 15 | 348.2 | 0.74 |
| 31 | 94 | 339.2 | 0.72 |
| 32 | 14 | 357.2 | 0.75 |
| 33 | 7.4 | 386.6 | 0.73 |
| 34 | 38 | 318.1 | 0.65 |
| 35 | 39 | 318.1 | 0.51 |
| 36 | 8.8 | 362.2 | 0.80 |
| 39 | 180 | 361.8 | 0.50 |
| 43 | 24 | 348.2 | 0.60 |
| 44 | 6.4 | 361.2 | 0.62 |
| 45 | 3.6 | 358.2 | 0.78 |
| 46 | 190 | 396.1 | 0.71 |
| 47 | 57 | 386.1 | 0.89 |
| 48 | 33 | 362.1 | 0.66 |
| 49 | 390 | 389.2 | 0.65 |
| 50 | 570 | 417.2 | 0.63 |
| 51 | 240 | 376.2 | 0.62 |
| 52 | 56 | 357.2 | 0.70 |
| 53 | 7.6 | 348.2 | 0.60 |
| 54 | 41 | 368.7 | 0.69 |
| 55 | 9.7 | 433.2 | 0.85 |
| 56 | 10 | 448.3 | 0.67 |
| 57 | 4.5 | 434.3 | 0.60 |
| 58 | 3.8 | 447.3 | 0.62 |
| 59 | 9.1 | 417.2 | 0.63 |
| 60 | 8.4 | 392.3 | 0.61 |
| 63 | 1.9 | 459.3 | 0.58 |
| 65 | 2.3 | 431.2 | 0.66 |
| 66 | 3.9 | 429.2 | 0.64 |
| 67 | 1.6 | 431.2 | 0.64 |
| 68 | 1.1 | 491.2 | 0.53 |
| 71 | 2.7 | 358.2 | 0.69 |
| 72 | 3.9 | 361.2 | 0.57 |
| 73 | 15 | 517.4 | 0.92 |
| 74 | 1 | 493.3 | 0.54 |
| 75 | 0.9 | 517.4 | 0.54 |
| 76 | 0.61 | 430.2 | 0.49 |
| 77 | 1.1 | 448.8 | 0.57 |
| 78 | 1.3 | 417.2 | 0.62 |
| 79 | 1.4 | 473.4 | 0.53 |
| 80 | 26 | 424.2 | 0.90 |
| 81 | 5.4 | 377.3 | 0.84 |
| 92 | 1.5 | 417.3 | 0.54 |
| 93 | 1.5 | 470.3 | 0.58 |
| 94 | 0.81 | 472.3 | 0.54 |
| 95 | 6.1 | 334.1 | 0.61 |
| 96 | 5.4 | 419.3 | 0.76 |
| 97 | 3.3 | 415.2 | 0.83 |
| 98 | 10 | 403.2 | 0.73 |
| 99 | 2.6 | 387.2 | 0.75 |
| 100 | 29 | 416.2 | 0.57 |
| 101 | 370 | 401.2 | 0.63 |
| 104 | 1.9 | 396.1 | 0.86 |
| 105 | 1 | 376.2 | 0.82 |
| 106 | 7 | 333.2 | 0.59 |
| 107 | 3.3 | 391.3 | 0.63 |
| 108 | 4.4 | 417.3 | 0.68 |
| 109 | 3.6 | 430.2 | 0.73 |
| 110 | 3.4 | 418.2 | 0.71 |
| 111 | 5.3 | 376.3 | 0.66 |
| 112 | 7.8 | 406.3 | 0.69 |
| 113 | 3.5 | 403.2 | 0.75 |
| 114 | 2.7 | 417.2 | 0.79 |
| 115 | 2.7 | 415.2 | 0.77 |
| 116 | 7.2 | 393.2 | 0.68 |
| 117 | 3.4 | 389.2 | 0.70 |
| 118 | 110 | 362.2 | 0.88 |
| 119 | 24 | 332.2 | 0.78 |
| 121 | 13 | 417.2 | 0.79 |
| 122 | 9.5 | 411.1 | 0.67 |
| 123 | 43 | 400.1 | 0.94 |
| 124 | 13 | 431.2 | 0.64 |
| 125 | 130 | 415.2 | 0.63 |
| 126 | 20 | 445.2 | 0.65 |
| 127 | 86 | 349.2 | 0.82 |
| 128 | 94 | 403.2 | 0.80 |
| 129 | 44 | 445.2 | 0.65 |
| 131 | 11 | 383.2 | 0.76 |
| 135 | 120 | 431.2 | 0.62 |
| 136 | 43 | 479.2 | 0.74 |
| 137 | 120 | 418.2 | 0.62 |
| 138 | 25 | 404.2 | 0.61 |
| 140 | 38 | 429.2 | 0.67 |
| 141 | 2.6 | 348.5 | 0.61 |
| 142 | 3.2 | 446.2 | 0.63 |
| 143 | 6.1 | 419.2 | 0.66 |
| 144 | 2.9 | 401.2 | 0.71 |
| 145 | 4.7 | 404.2 | 0.76 |
| 146 | 6.1 | 389.3 | 0.97 |
| 147 | 8.1 | 433.4 | 0.91 |
| 148 | 12 | 403.3 | 0.93 |
| 149 | 8.9 | 460.3 | 0.69 |
| 150 | 7 | 419.3 | 0.77 |
| 151 | 6.4 | 428.3 | 0.80 |
| 152 | 4.2 | 449.3 | 0.74 |
| 153 | 1.6 | 489.3 | 0.49 |
| 154 | 1.8 | 501.4 | 0.50 |
| 155 | 1.7 | 515.5 | 0.51 |
| 156 | 1.6 | 489.3 | 0.52 |
| 157 | 1.9 | 474.3 | 0.50 |
| 158 | 1.2 | 542.5 | 0.50 |
| 159 | 1.8 | 501.3 | 0.52 |
| 160 | 1.1 | 529.5 | 0.55 |
| 161 | 1.5 | 501.3 | 0.52 |
| 162 | 2.3 | 501.3 | 0.51 |
| 163 | 1.1 | 530.3 | 0.51 |
| 164 | 2.1 | 515.5 | 0.52 |
| 165 | 1.2 | 514.3 | 0.53 |
| 166 | 0.94 | 487.3 | 0.50 |
| 167 | 1 | 513.3 | 0.52 |
| 168 | 0.95 | 517.4 | 0.51 |
| 169 | 1.3 | 467.4 | 0.51 |
| 170 | 1.8 | 467.3 | 0.52 |
| 171 | 1.4 | 463.5 | 0.54 |
| 172 | 1.8 | 450.3 | 0.56 |
| 173 | 1.8 | 499.2 | 0.53 |
| 174 | 1.5 | 481.4 | 0.50 |
| 175 | 1.7 | 485.3 | 0.54 |
| 176 | 1.5 | 485.3 | 0.54 |

Additional assays such as human whole blood TNF inhibition, human hepatocyte stability and CACO-2 permeability were carried out to obtain cellular potency, stability and cell permeability respectively.

Method of Use

The compounds of the invention are effective inhibitors of RIPK2. Therefore, in one embodiment of the invention, there is provided methods of treating RIPK2 mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, pharmacological inhibition of RIPK2 will attenuate pro-inflammatory signaling through the bacterial sensing pathways initiated by NOD1 and NOD2 stimulation. This reduction in inflammatory signaling will provide therapeutic benefit in a variety of autoinflammatory diseases.

These Include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease (Crohn's Disease and Ulcerative Colitis), Blau syndrome, systemic lupus erythematosus, transplant rejection, multiple sclerosis, inflammatory pain, inflammatory and allergic ocular diseases;

Autoimmune disease or allergic disorder is selected from rheumatoid arthritis, psoriasis, systemic lupus erythromatosis, lupus nephritis, scleroderma, asthma, Chronic Obstructive Pulmonary Disease (COPD), allergic rhinitis, allergic eczema, multiple sclerosis, juvenile rheumatoid arthritis, juvenile idiopathic arthritis, type I diabetes, inflammatory bowel disease (Crohn's Disease and Ulcerative Colitis), graft versus host disease, psoriatic arthritis, reactive arthritis, ankylosing spondylitis, Crohn's disease, ulcerative colitis, uveitis and non-radiographic spondyloarthropathy.

Cancer including solid tumors, leukemias and lymphomas; and

Renal diseases such as glomerulonephritis or diabetic nephropathy or diabetic kidney disease.

Liver disease such as Non-alcoholic fatty liver disease or non-alcoholic steato-hepatitis (NASH) or cirrhosis of the liver.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

The invention claimed is:

1. A compound of Formula (I),

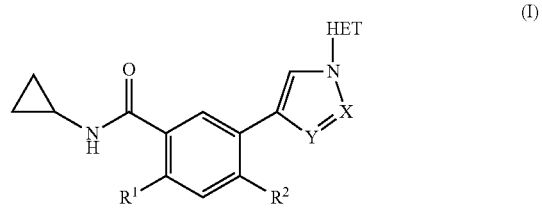

or pharmaceutically acceptable salts thereof, wherein:
HET is selected from:

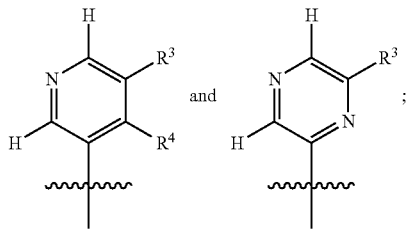

X is N and Y is CH; or
X is CH and Y is N;
$R^1$ is hydrogen or F;
$R^2$ is $C_{1-3}$ alkyl, Cl or F;
$R^3$ and $R^4$ are each independently selected from:
(a) —H,
(b) —$OR^5$,
(c) —O—$C_{1-6}$alkyl-O—$C_{1-3}$ alkyl
(d) —O—$C_{3-6}$ cycloalkyl,
(e) —$C(O)R^5$,
(f) $C_{1-6}$alkyl optionally substituted with one to three —OH, fluoro, heterocyclyl optionally substituted with oxo, $C_{3-6}$ cycloalkyl, —$CO_2R^5$, —O—$C_{1-6}$alkyl, aryl, —$N(R^5)(R^6)$, CN or —$C(O)N(R^5)(R^6)$,
(g) $C_{3-6}$ cycloalkyl optionally substituted with one to three —OH, one to three fluoro, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, $N(R^5)(R^6)$, or —$C(O)N(R^5)(R^6)$,
(h) —$CO_2R^5$,
(i) —$C(O)N(R^5)(R^6)$,
(j) —$S(O)_2N(R^5)(R^6)$,
(k) —$S(O)_n$—$R^5$
(l) 4-10 membered monocyclic, bicyclic or spirocyclic heterocyclyl group containing nitrogen, sulfur or oxygen optionally substituted with 1-3 groups selected from —$N(R^5)(R^6)$, halogen, —$C_{1-6}$ alkyl, —O—$C_{1-6}$ alkyl and —$C_{1-6}$ alkyl-halogen,
(m) aryl,
(n) —$N(R^5)(R^6)$, and
(o) halogen;
$R^5$ and $R^6$ are each independently selected from —H, —($C_1$-$C_6$)alkyl-heterocyclyl, 4-6 membered heterocyclyl wherein the heterocyclic ring is optionally substituted with 1-3 substituents selected from —($C_1$-$C_6$)alkyl, —O—$C_{1-6}$ alkyl, —$C_{1-6}$ alkyl-halogen, —($C_1$-$C_6$)cycloalkyl, halogen, acyl, heterocyclyl, heterocyclyl-($C_1$-$C_6$)alkyl, heterocyclyl-O—($C_1$-$C_6$)alkyl, heterocyclyl-OH, heterocyclyl-C(O)—$CH_3$, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$) alkyl, $C_{3-6}$ cycloalkyl-O—($C_1$-$C_6$)alkyl, and $C_{3-6}$ cycloalkyl-O—($C_1$-$C_6$)alkyl-OH;
acyl, $C_{3-6}$ cycloalkyl-C(O)—$C_{1-3}$ alkyl, —C(O)—$C_{1-3}$ alkyl-O—$CH_3$, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally monosubstituted or disubstituted with —($C_1$-$C_3$)—OH, —C(O)—NH—$C_3$-$C_6$ heterocyclyl, —C(O)-aryl, —C(O)-heteroaryl —S(O)n-$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or
$R^5$ and $R^6$ together with the nitrogen atom to which they are attached form a 5-6 membered heterocyclic ring optionally substituted with methyl; and
n is 0, 1 or 2.

2. The compound of claim 1, or a pharmaceutically acceptable salt thereof, wherein:
HET is:

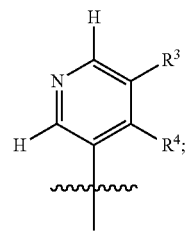

X is N and Y is CH;
$R^1$ is hydrogen or F;
$R^2$ is $C_{1-3}$ alkyl, Cl or F;
$R^3$ and $R^4$ are each independently selected from:
(a) —H,
(b) —$OR^5$,
(c) —O—$C_{1-6}$alkyl-O—$C_{1-3}$ alkyl
(d) —O—$C_{3-6}$ cycloalkyl,
(e) —$C(O)R^5$,
(f) $C_{1-6}$alkyl optionally substituted with one to three —OH, fluoro, heterocyclyl optionally substituted with oxo, $C_{3-6}$ cycloalkyl, —$CO_2R^5$, —O—$C_{1-6}$alkyl, aryl, —$N(R^5)(R^6)$, CN or —$C(O)N(R^5)(R^6)$,
(g) $C_{3-6}$ cycloalkyl optionally substituted with one to three —OH, one to three fluoro, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, $N(R^5)(R^6)$, or —$C(O)N(R^5)(R^6)$,
(h) —$CO_2R^5$,
(i) —$C(O)N(R^5)(R^6)$,
(j) —$S(O)_2N(R^5)(R^6)$,
(k) —$S(O)_n$—$R^5$
(l) 4-10 membered monocyclic, bicyclic or spirocyclic heterocyclyl group containing nitrogen, sulfur or oxygen,
(m) aryl,
(n) —$N(R^5)(R^6)$, and
(o) halogen;
$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl-O—($C_1$-$C_6$)alkyl, heterocyclyl-OH, heterocyclyl-C(O)—$CH_3$, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$) alkyl-O—($C_1$-$C_6$)alkyl-, $C_{3-6}$ cycloalkyl, —($C_1$-$C_6$)

alkyl-cycloalkyl, $C_{3-6}$ cycloalkyl-$(C_1$-$C_6)$alkyl, $C_{3-6}$ cycloalkyl-O—$(C_1$-$C_6)$alkyl, and $C_{3-6}$ cycloalkyl-O—$(C_1$-$C_6)$alkyl-OH;

acyl, $C_{3-6}$ cycloalkyl-C(O)—$C_{1-3}$ alkyl, alkyl-O—$CH_3$, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally monosubstituted or disubstituted with —$(C_1$-$C_3)$—OH, —C(O)—NH—$C_3$-$C_6$ heterocyclyl, —C(O)-aryl, —C(O)-heteroaryl —S(O)n-$C_1$-$C_3$-alkyl and —$(C_1$-$C_6)$alkyl optionally substituted with —OH, O—$(C_1$-$C_3)$-alkyl, $C_{3-6}$ cycloalkyl, heterocyclyl, aryl, —NH—$C_{1-3}$ alkyl or —N—$(C_{1-3}$-alkyl$)_2$; or $R^5$ and $R^6$ together with the nitrogen atom to which they are attached form a 5-6 membered heterocyclic ring optionally substituted with methyl; and n is 1 or 2.

3. The compound of claim 1, or a pharmaceutically acceptable salt thereof, wherein:

HET is:

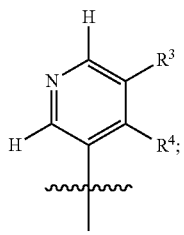

X is N and Y is CH;
$R^2$ is selected from methyl and Cl;
$R^3$ is selected from:
  (a) —H,
  (b) —$OR^5$,
  (c) —O—$C_{1-6}$alkyl-O—$C_{1-3}$ alkyl
  (d) —O—$C_{3-6}$ cycloalkyl,
  (e) —C(O)$R^5$,
  (f) $C_{1-6}$alkyl optionally substituted with one to three —OH, fluoro, heterocyclyl optionally substituted with oxo, $C_{3-6}$ cycloalkyl, —$CO_2R^5$, —O—$C_{1-6}$alkyl, aryl, —N($R^5$)($R^6$), CN, or —C(O)N($R^5$)($R^6$),
  (g) $C_{3-6}$ cycloalkyl optionally substituted with one to three —OH, one to three fluoro, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, N($R^5$)($R^6$), or —C(O)N($R^5$)($R^6$),
  (h) —$CO_2R^5$,
  (i) —C(O)N($R^5$)($R^6$),
  (j) —S(O)$_2$N($R^5$)($R^6$),
  (k) —S(O)$_n$—$R^5$
  (l) 4-10 membered monocyclic, bicyclic or spirocyclic heterocyclyl group containing nitrogen, sulfur or oxygen,
  (m) aryl,
  (n) —N($R^5$)($R^6$), and
  (o) halogen;
$R^4$ is H;
$R^5$ and $R^6$ are each independently selected from —H, 4-6 membered heterocyclyl wherein the heterocyclic ring is optionally substituted with 1-3 substituents selected from —$(C_1$-$C_6)$alkyl, —$(C_1$-$C_6)$cycloalkyl, halogen, acyl, heterocyclyl, heterocyclyl-$(C_1$-$C_6)$alkyl, heterocyclyl-O—$(C_1$-$C_6)$alkyl, heterocyclyl-OH, heterocyclyl-C(O)—$CH_3$, heterocyclyl-C(O)—O$(C_1$-$C_3)$ alkyl, —$(C_1$-$C_6)$alkyl-heterocyclyl, —$(C_1$-$C_6)$alkyl-heterocyclyl-$(C_1$-$C_6)$alkyl, —$(C_1$-$C_6)$alkyl-O—H, —$(C_1$-$C_6)$alkyl-O—$(C_1$-$C_6)$alkyl-, $C_{3-6}$ cycloalkyl, —$(C_1$-$C_6)$alkyl-cycloalkyl, $C_{3-6}$ cycloalkyl-$(C_1$-$C_6)$alkyl, $C_{3-6}$ cycloalkyl-O—$(C_1$-$C_6)$alkyl, and $C_{3-6}$ cycloalkyl-O—$(C_1$-$C_6)$alkyl-OH;

acyl, $C_{3-6}$ cycloalkyl-C(O)—$C_{1-3}$ alkyl, —C(O)—$C_{1-3}$ alkyl-O—$CH_3$, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally monosubstituted or disubstituted with —$(C_1$-$C_3)$—OH, —C(O)—NH—$C_3$-$C_6$ heterocyclyl, —C(O)-aryl, —C(O)-heteroaryl —S(O)n-$C_1$-$C_3$-alkyl and —$(C_1$-$C_6)$alkyl optionally substituted with —OH, O—$(C_1$-$C_3)$-alkyl, $C_{3-6}$ cycloalkyl, heterocyclyl, aryl, —NH—$C_{1-3}$ alkyl or —N—$(C_{1-3}$-alkyl$)_2$; or $R^5$ and $R^6$ together with the nitrogen atom to which they are attached form a 5-6 membered heterocyclic ring optionally substituted with methyl; and n is 2.

4. The compound of claim 1, or a pharmaceutically acceptable salt thereof, wherein:

HET is:

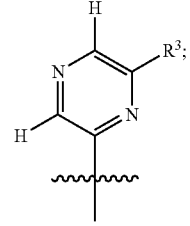

X is N and Y is CH;
$R^2$ is $CH_3$ or Cl;
$R^3$ is selected from:
  (a) —H,
  (b) —$OR^5$,
  (c) —O—$C_{1-6}$alkyl-O—$C_{1-3}$ alkyl
  (d) —O—$C_{3-6}$ cycloalkyl,
  (e) —C(O)$R^5$,
  (f) $C_{1-6}$alkyl optionally substituted with one to three —OH, fluoro, heterocyclyl optionally substituted with oxo, $C_{3-6}$ cycloalkyl, —$CO_2R^5$, —O—$C_{1-6}$alkyl, aryl, —N($R^5$)($R^6$), CN, or —C(O)N($R^5$)($R^6$),
  (g) $C_{3-6}$ cycloalkyl optionally substituted with one to three —OH, one to three fluoro, $C_{1-6}$alkyl, —$OC_{1-6}$alkyl, $C_{1-6}$alkyl-$OC_{1-6}$alkyl, $C_{1-6}$alkyl-OH, $CF_3$, CN, —$OC_{3-6}$cycloalkyl, —$CO_2H$, —$CO_2R^5$, $C_{3-6}$cycloalkyl, 5-6 membered heteroaryl, $C_{3-6}$ heterocyclyl, N($R^5$)($R^6$), or —C(O)N($R^5$)($R^6$),
  (h) —$CO_2R^5$,
  (i) —C(O)N($R^5$)($R^6$),
  (j) —S(O)$_2$N($R^5$)($R^6$),
  (k) —S(O)$_n$—$R^5$
  (l) 4-10 membered monocyclic, bicyclic or spirocyclic heterocyclyl group containing nitrogen, sulfur or oxygen, (m) aryl,
(n) —N(R$^5$)(R$^6$), and
(o) halogen;

R$^5$ and R$^6$ are each independently selected from —H, 4-6 membered heterocyclyl wherein the heterocyclic ring is optionally substituted with 1-3 substituents selected from —(C$_1$-C$_6$)alkyl, —(C$_1$-C$_6$)cycloalkyl, halogen, acyl, heterocyclyl, heterocyclyl-(C$_1$-C$_6$)alkyl, heterocyclyl-O—(C$_1$-C$_6$)alkyl, heterocyclyl-OH, heterocyclyl-C(O)—CH$_3$, heterocyclyl-C(O)—O(C$_1$-C$_3$) alkyl, —(C$_1$-C$_6$)alkyl-heterocyclyl, —(C$_1$-C$_6$)alkyl-heterocyclyl-(C$_1$-C$_6$)alkyl, —(C$_1$-C$_6$)alkyl-O—H, —(C$_1$-C$_6$)alkyl-O—(C$_1$-C$_6$)alkyl-, C$_{3-6}$ cycloalkyl, —(C$_1$-C$_6$)alkyl-cycloalkyl, C$_{3-6}$ cycloalkyl-(C$_1$-C$_6$)alkyl, C$_{3-6}$ cycloalkyl-O—(C$_1$-C$_6$)alkyl, and C$_{3-6}$ cycloalkyl-O—(C$_1$-C$_6$)alkyl-OH;

acyl, C$_{3-6}$ cycloalkyl-C(O)—C$_{1-3}$ alkyl, —C(O)—C$_{1-3}$ alkyl-O—CH$_3$, —C(O)—C$_{1-3}$ alkyl, —C(O)—C$_{3-6}$ cycloalkyl; —C(O)—NH—C$_{1-3}$ alkyl, —C(O)—NH—C$_{1-3}$ alkyl, —C(O)—NH—C$_{3-6}$ cycloalkyl optionally monosubstituted or disubstituted with —(C$_1$-C$_3$)—OH, —C(O)—NH—C$_{3-6}$ heterocyclyl, —C(O)-aryl, —C(O)-heteroaryl —S(O)n-C$_1$-C$_3$-alkyl and —(C$_1$-C$_6$)alkyl optionally substituted with —OH, O—(C$_1$-C$_3$)-alkyl, C$_{3-6}$ cycloalkyl, heterocyclyl, aryl, —NH—C$_{1-3}$ alkyl or —N—(C$_{1-3}$-alkyl)$_2$; or R$^5$ and R$^6$ together with the nitrogen atom to which they are attached form a 5-6 membered heterocyclic ring optionally substituted with methyl; and n is 2.

5. The compound of claim 4, or a pharmaceutically acceptable salt thereof, wherein:

HET is:

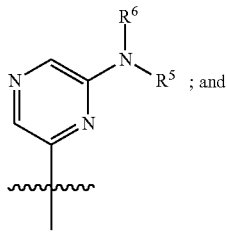

; and

R$^5$ and R$^6$ are each independently selected from —H, 4-6 membered heterocyclyl wherein the heterocyclic ring is optionally substituted with 1-3 substituents selected from —(C$_1$-C$_6$)alkyl, —(C$_1$-C$_6$)cycloalkyl, halogen, acyl, heterocyclyl, heterocyclyl-(C$_1$-C$_6$)alkyl, heterocyclyl-O—(C$_1$-C$_6$)alkyl, heterocyclyl-OH, heterocyclyl-C(O)—CH$_3$, heterocyclyl-C(O)—O(C$_1$-C$_3$) alkyl, —(C$_1$-C$_6$)alkyl-heterocyclyl, —(C$_1$-C$_6$)alkyl-heterocyclyl-(C$_1$-C$_6$)alkyl, —(C$_1$-C$_6$)alkyl-O—H, —(C$_1$-C$_6$)alkyl-O—(C$_1$-C$_6$)alkyl-, C$_{3-6}$ cycloalkyl, —(C$_1$-C$_6$)alkyl-cycloalkyl, C$_{3-6}$ cycloalkyl-(C$_1$-C$_6$)alkyl, C$_{3-6}$ cycloalkyl-O—(C$_1$-C$_6$)alkyl, and C$_{3-6}$ cycloalkyl-O—(C$_1$-C$_6$)alkyl-OH;

acyl, C$_{3-6}$ cycloalkyl-C(O)—C$_{1-3}$ alkyl, —C(O)—C$_{1-3}$ alkyl-O—CH$_3$, —C(O)—C$_{1-3}$ alkyl, —C(O)—C$_{3-6}$ cycloalkyl; —C(O)—NH—C$_{1-3}$ alkyl, —C(O)—NH—C$_{1-3}$ alkyl, —C(O)—NH—C$_{3-6}$ cycloalkyl optionally monosubstituted or disubstituted with —(C$_1$-C$_3$)—OH, —C(O)—NH—C$_{3-6}$ heterocyclyl, —C(O)-aryl, —C(O)-heteroaryl —S(O)$_2$—C$_1$-C$_3$-alkyl and —(C$_1$-C$_6$)alkyl optionally substituted with —OH, O—(C$_1$-C$_3$)-alkyl, C$_{3-6}$ cycloalkyl, heterocyclyl, aryl, —NH—C$_{1-3}$ alkyl or —N—(C$_{1-3}$-alkyl)$_2$; or R$^5$ and R$^6$ together with the nitrogen atom to which they are attached form a 5-6 membered heterocyclic ring optionally substituted with methyl.

6. The compound of claim 1, or a pharmaceutically acceptable salt thereof, wherein:

HET is:

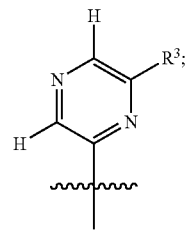

X is CH and Y is N;
R$^1$ is H or F;
R$^2$ is CH$_3$ or Cl;
R$^3$ is selected from:
(a) —H,
(b) —OR$^5$,
(c) —O—C$_{1-6}$alkyl-O—C$_{1-3}$ alkyl
(d) —O—C$_{3-6}$ cycloalkyl,
(e) —C(O)R$^5$,
(f) C$_{1-6}$alkyl optionally substituted with one to three —OH, fluoro, heterocyclyl optionally substituted with oxo, C$_{3-6}$ cycloalkyl, —CO$_2$R$^5$, —O—C$_{1-6}$alkyl, aryl, —N(R$^5$)(R$^6$), CN, or —C(O)N(R$^5$)(R$^6$),
(g) C$_{3-6}$ cycloalkyl optionally substituted with one to three —OH, one to three fluoro, C$_{1-6}$alkyl, —OC$_{1-6}$alkyl, C$_{1-6}$alkyl-OC$_{1-6}$alkyl, C$_{1-6}$alkyl-OH, CF$_3$, CN, —OC$_{3-6}$cycloalkyl, —CO$_2$H, —CO$_2$R$^5$, C$_{3-6}$cycloalkyl, 5-6 membered heteroaryl, C$_{3-6}$ heterocyclyl, N(R$^5$)(R$^6$), or —C(O)N(R$^5$)(R$^6$),
(h) —CO$_2$R$^5$,
(i) —C(O)N(R$^5$)(R$^6$),
(j) —S(O)$_2$N(R$^5$)(R$^6$),
(k) —S(O)$_n$—R$^5$
(l) 4-10 membered monocyclic, bicyclic or spirocyclic heterocyclyl group containing nitrogen, sulfur or oxygen,
(m) aryl,
(n) —N(R$^5$)(R$^6$), and
(o) halogen;

R$^5$ and R$^6$ are each independently selected from —H, 4-6 membered heterocyclyl wherein the heterocyclic ring is optionally substituted with 1-3 substituents selected from —(C$_1$-C$_6$)alkyl, —(C$_1$-C$_6$)cycloalkyl, halogen, acyl, heterocyclyl, heterocyclyl-(C$_1$-C$_6$)alkyl, heterocyclyl-O—(C$_1$-C$_6$)alkyl, heterocyclyl-OH, heterocyclyl-C(O)—CH$_3$, heterocyclyl-C(O)—O(C$_1$-C$_3$) alkyl, —(C$_1$-C$_6$)alkyl-heterocyclyl, —(C$_1$-C$_6$)alkyl-heterocyclyl-(C$_1$-C$_6$)alkyl, —(C$_1$-C$_6$)alkyl-O—H, —(C$_1$-C$_6$)alkyl-O—(C$_1$-C$_6$)alkyl-, C$_{3-6}$ cycloalkyl, —(C$_1$-C$_6$)alkyl-cycloalkyl, C$_{3-6}$ cycloalkyl-(C$_1$-C$_6$)alkyl, C$_{3-6}$ cycloalkyl-O—(C$_1$-C$_6$)alkyl, and C$_{3-6}$ cycloalkyl-O—(C$_1$-C$_6$)alkyl-OH;

acyl, C$_{3-6}$ cycloalkyl-C(O)—C$_{1-3}$ alkyl, —C(O)—C$_{1-3}$ alkyl-O—CH$_3$, —C(O)—C$_{1-3}$ alkyl, —C(O)—C$_{3-6}$ cycloalkyl; —C(O)—NH—C$_{1-3}$ alkyl, —C(O)—

NH—C₁-C₃ alkyl, —C(O)—NH—C₃-C₆ cycloalkyl optionally monosubstituted or disubstituted with —(C₁-C₃)—OH, —C(O)—NH—C₃-C₆ heterocyclyl, —C(O)-aryl, —C(O)-heteroaryl —S(O)n-C₁-C₃-alkyl and —(C₁-C₆)alkyl optionally substituted with —OH, O—(C₁-C₃)-alkyl, C₃₋₆ cycloalkyl, heterocyclyl, aryl, —NH—C₁₋₃ alkyl or —N—(C₁₋₃-alkyl)₂; or R⁵ and R⁶ together with the nitrogen atom to which they are attached form a 5-6 membered heterocyclic ring optionally substituted with methyl; and n is 2.

7. The compound of claim 6, or a pharmaceutically acceptable salt thereof, wherein:

HET is:

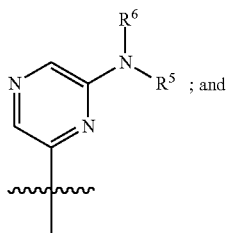 ; and

R⁵ and R⁶ are each independently selected from —H, 4-6 membered heterocyclyl wherein the heterocyclic ring is optionally substituted with 1-3 substituents selected from —(C₁-C₆)alkyl, —(C₁-C₆)cycloalkyl, halogen, acyl, heterocyclyl, heterocyclyl-(C₁-C₆)alkyl, heterocyclyl-O—(C₁-C₆)alkyl, heterocyclyl-OH, heterocyclyl-C(O)—CH₃, heterocyclyl-C(O)—O(C₁-C₃) alkyl, —(C₁-C₆)alkyl-heterocyclyl, —(C₁-C₆)alkyl-heterocyclyl-(C₁-C₆)alkyl, —(C₁-C₆)alkyl-O—H, —(C₁-C₆) alkyl-O—(C₁-C₆)alkyl-, C₃₋₆ cycloalkyl, —(C₁-C₆) alkyl-cycloalkyl, C₃₋₆ cycloalkyl-(C₁-C₆)alkyl, C₃₋₆ cycloalkyl-O—(C₁-C₆)alkyl, and C₃₋₆ cycloalkyl-O—(C₁-C₆)alkyl-OH;

acyl, C₃₋₆ cycloalkyl-C(O)—C₁₋₃ alkyl, —C(O)—C₁₋₃ alkyl-O—CH₃, —C(O)—C₁₋₃ alkyl, —C(O)—C₃₋₆ cycloalkyl; —C(O)—NH—C₁-C₃ alkyl, —C(O)—NH—C₁-C₃ alkyl, —C(O)—NH—C₃-C₆ cycloalkyl optionally monosubstituted or disubstituted with —(C₁-C₃)—OH, —C(O)—NH—C₃-C₆ heterocyclyl, —C(O)-aryl, —C(O)-heteroaryl —S(O)₂—C₁-C₃-alkyl and —(C₁-C₆)alkyl optionally substituted with —OH, O—(C₁-C₃)-alkyl, C₃₋₆ cycloalkyl, heterocyclyl, aryl, —NH—C₁₋₃ alkyl or —N—(C₁₋₃-alkyl)₂; or R⁵ and R⁶ together with the nitrogen atom to which they are attached form a 5-6 membered heterocyclic ring optionally substituted with methyl.

8. The compound of claim 1, or a pharmaceutically acceptable salt thereof, wherein:

HET is:

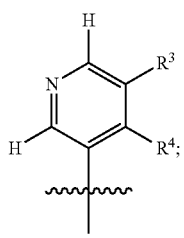

X is CH and Y is N;

R² is CH₃ or Cl;

R³ is selected from:

(a) —H, (b) —OR⁵, (c) —O—C₁₋₆alkyl-O—C₁₋₃ alkyl (d) —O—C₃₋₆ cycloalkyl, (e) —C(O)R⁵, (f) C₁₋₆alkyl optionally substituted with one to three —OH, fluoro, heterocyclyl optionally substituted with oxo, C₃₋₆ cycloalkyl, —CO₂R⁵, —O—C₁₋₆alkyl, aryl, —N(R⁵)(R⁶), CN, or —C(O)N(R⁵)(R⁶), (g) C₃₋₆ cycloalkyl optionally substituted with one to three —OH, one to three fluoro, C₁₋₆alkyl, —OC₁₋₆alkyl, C₁₋₆alkyl-OC₁₋₆alkyl, C₁₋₆alkyl-OH, CF₃, CN, —OC₃₋₆cycloalkyl, —CO₂H, —CO₂R⁵, C₃₋₆cycloalkyl, 5-6 membered heteroaryl, C₃₋₆ heterocyclyl, N(R⁵)(R⁶), or —C(O)N(R⁵)(R⁶), (h) —CO₂R⁵, (i) —C(O)N(R⁵)(R⁶), (j) —S(O)₂N(R⁵)(R⁶), (k) —S(O)ₙ—R⁵

(l) 4-10 membered monocyclic, bicyclic or spirocyclic heterocyclyl group containing nitrogen, sulfur or oxygen, (m) aryl, (n) —N(R⁵)(R⁶), and (o) halogen;

R⁴ is H;

R⁵ and R⁶ are each independently selected from —H, 4-6 membered heterocyclyl wherein the heterocyclic ring is optionally substituted with 1-3 substituents selected from —(C₁-C₆)alkyl, —(C₁-C₆)cycloalkyl, halogen, acyl, heterocyclyl, heterocyclyl-(C₁-C₆)alkyl, heterocyclyl-O—(C₁-C₆)alkyl, heterocyclyl-OH, heterocyclyl-C(O)—CH₃, heterocyclyl-C(O)—O(C₁-C₃) alkyl, —(C₁-C₆)alkyl-heterocyclyl, —(C₁-C₆)alkyl-heterocyclyl-(C₁-C₆)alkyl, —(C₁-C₆)alkyl-O—H, —(C₁-C₆) alkyl-O—(C₁-C₆)alkyl-, C₃₋₆ cycloalkyl, —(C₁-C₆) alkyl-cycloalkyl, C₃₋₆ cycloalkyl-(C₁-C₆)alkyl, C₃₋₆ cycloalkyl-O—(C₁-C₆)alkyl, and C₃₋₆ cycloalkyl-O—(C₁-C₆)alkyl-OH;

acyl, C₃₋₆ cycloalkyl-C(O)—C₁₋₃ alkyl, —C(O)—C₁₋₃ alkyl-O—CH₃, —C(O)—C₁₋₃ alkyl, —C(O)—C₃₋₆ cycloalkyl; —C(O)—NH—C₁-C₃ alkyl, —C(O)—NH—C₁-C₃ alkyl, —C(O)—NH—C₃-C₆ cycloalkyl optionally monosubstituted or disubstituted with —(C₁-C₃)—OH, —C(O)—NH—C₃-C₆ heterocyclyl, —C(O)-aryl, —C(O)-heteroaryl —S(O)n-C₁-C₃-alkyl and —(C₁-C₆)alkyl optionally substituted with —OH, O—(C₁-C₃)-alkyl, C₃₋₆ cycloalkyl, heterocyclyl, aryl, —NH—C₁₋₃ alkyl or —N—(C₁₋₃-alkyl)₂; or R⁵ and R⁶ together with the nitrogen atom to which they are attached form a 5-6 membered heterocyclic ring optionally substituted with methyl; and n is 2.

9. The compound of claim 8, or a pharmaceutically acceptable salt thereof, wherein:

HET is:

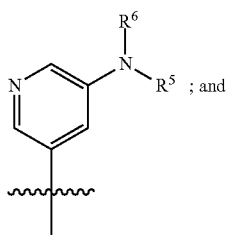

R⁵ and R⁶ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl-O—($C_1$-$C_6$)alkyl, heterocyclyl-OH, heterocyclyl-C(O)—$CH_3$, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$)alkyl-O—($C_1$-$C_6$)alkyl-, $C_{3-6}$ cycloalkyl, —($C_1$-$C_6$)alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH;

acyl, $C_{3-6}$ cycloalkyl-C(O)—$C_{1-3}$ alkyl, —C(O)—$C_{1-3}$ alkyl-O—$CH_3$, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally monosubstituted or disubstituted with —($C_1$-$C_3$)—OH, —C(O)—NH—$C_3$-$C_6$ heterocyclyl, —C(O)-aryl, —C(O)-heteroaryl —S(O)$_2$—$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or R⁵ and R⁶ together with the nitrogen atom to which they are attached form a 5-6 membered heterocyclic ring optionally substituted with methyl.

10. The compound of claim 1, or a pharmaceutically acceptable salt thereof, wherein:

HET is selected from the group consisting of:

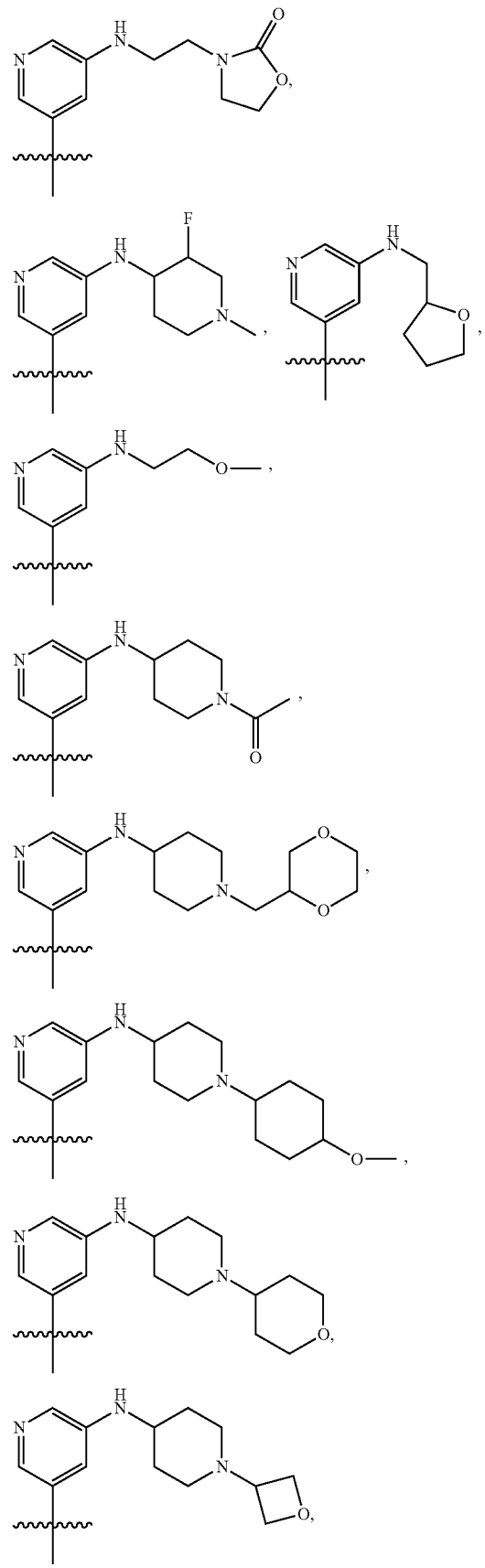

-continued

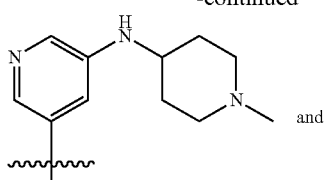 and

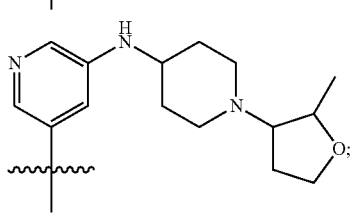;

X is N and Y is CH;
R¹ is F; and
R² is methyl.

11. The compound of claim 1, or a pharmaceutically acceptable salt thereof, wherein:
HET is selected from the group consisting of:

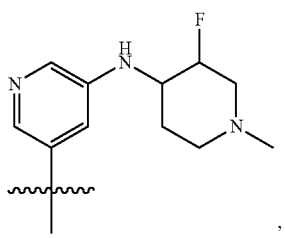,

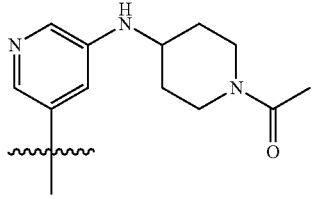,

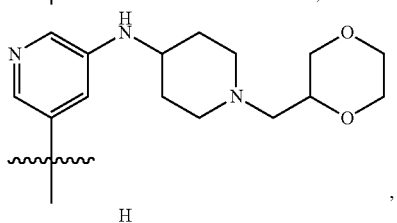,

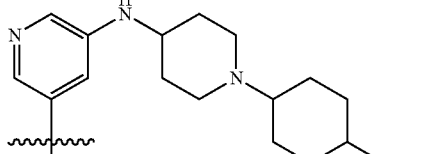,

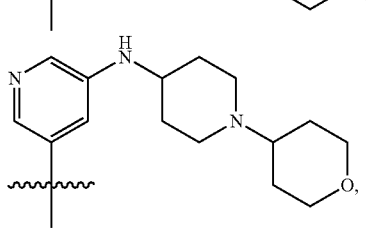,

-continued

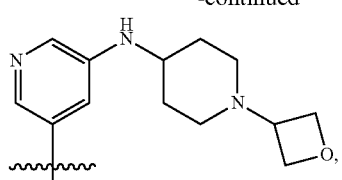,

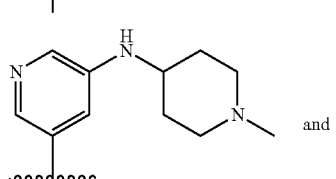 and

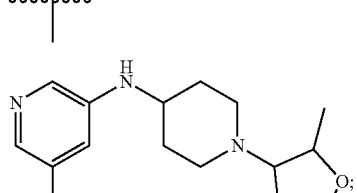;

X is N and Y is CH;
R¹ is F; and
R² is CH₃.

12. The compound of claim 11, or a pharmaceutically acceptable salt thereof, wherein:
HET is selected from the group consisting of:

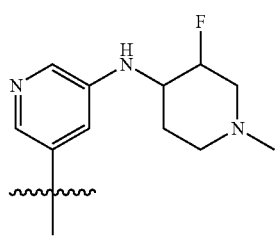,

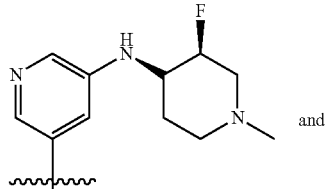 and

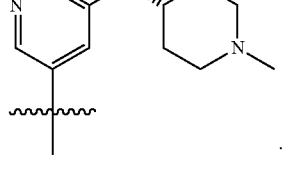.

13. The compound of claim 3, or a pharmaceutically acceptable salt thereof, wherein:

HET is:

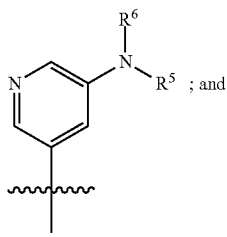

$R^5$ and $R^6$ are each independently selected from —H, 4-6 membered heterocyclyl wherein the heterocyclic ring is optionally substituted with 1-3 substituents selected from —($C_1$-$C_6$)alkyl, —($C_1$-$C_6$)cycloalkyl, halogen, acyl, heterocyclyl, heterocyclyl-($C_1$-$C_6$)alkyl, heterocyclyl-O—($C_1$-$C_6$)alkyl, heterocyclyl-OH, heterocyclyl-C(O)—$CH_3$, heterocyclyl-C(O)—O($C_1$-$C_3$) alkyl, —($C_1$-$C_6$)alkyl-heterocyclyl, —($C_1$-$C_6$)alkyl-heterocyclyl-($C_1$-$C_6$)alkyl, —($C_1$-$C_6$)alkyl-O—H, —($C_1$-$C_6$) alkyl-O—($C_1$-$C_6$)alkyl-, $C_{3-6}$ cycloalkyl, —($C_1$-$C_6$) alkyl-cycloalkyl, $C_{3-6}$ cycloalkyl-($C_1$-$C_6$)alkyl, $C_{3-6}$ cycloalkyl-O—($C_1$-$C_6$)alkyl, and $C_{3-6}$ cycloalkyl-O—($C_1$-$C_6$)alkyl-OH;

acyl, $C_{3-6}$ cycloalkyl-C(O)—$C_{1-3}$ alkyl, —C(O)—$C_{1-3}$ alkyl-O—$CH_3$, —C(O)—$C_{1-3}$ alkyl, —C(O)—$C_{3-6}$ cycloalkyl; —C(O)—NH—$C_1$-$C_3$ alkyl, —C(O)—NH—$C_1$-$C_3$ alkyl, —C(O)—NH—$C_3$-$C_6$ cycloalkyl optionally monosubstituted or disubstituted with —($C_1$-$C_3$)—OH, —C(O)—NH—$C_3$-$C_6$ heterocyclyl, —C(O)-aryl, —C(O)-heteroaryl —S(O)$_2$—$C_1$-$C_3$-alkyl and —($C_1$-$C_6$)alkyl optionally substituted with —OH, O—($C_1$-$C_3$)-alkyl, $C_{3-6}$ cycloalkyl, heterocyclyl, aryl, —NH—$C_{1-3}$ alkyl or —N—($C_{1-3}$-alkyl)$_2$; or $R^5$ and $R^6$ together with the nitrogen atom to which they are attached form a 5-6 membered heterocyclic ring optionally substituted with methyl.

14. The compound of claim 1, or a pharmaceutically acceptable salt thereof, wherein:

HET is:

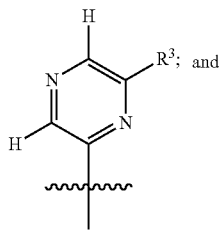

X is N and Y is CH.

15. The compound of claim 1, or a pharmaceutically acceptable salt thereof, wherein:

HET is:

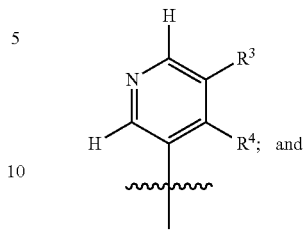

X is CH and Y is N.

16. The compound of claim 1, or a pharmaceutically acceptable salt thereof, wherein:

HET is:

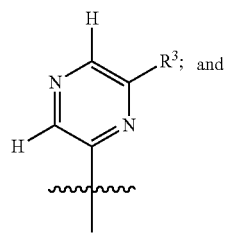

X is CH and Y is N.

17. The compound of claim 3, or a pharmaceutically acceptable salt thereof, wherein:

HET is selected from the group consisting of:

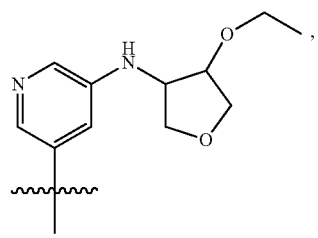

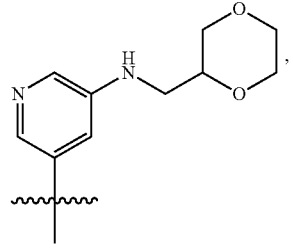

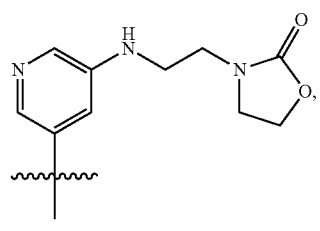

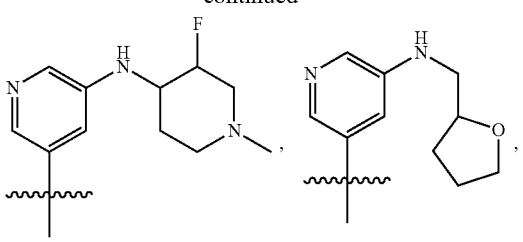
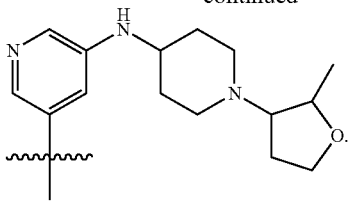
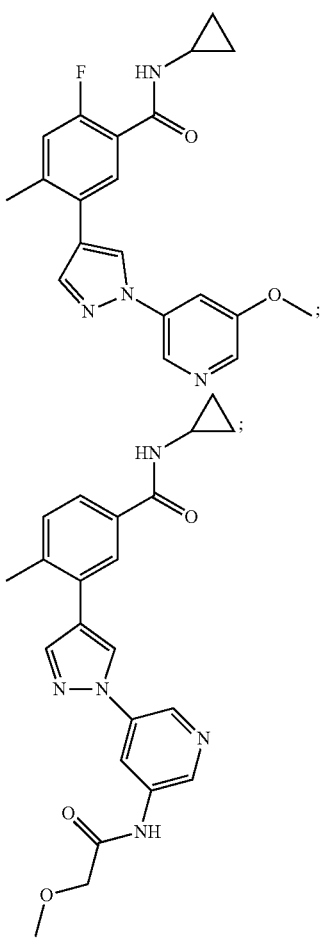

18. A pharmaceutical composition comprising a compound of claim 1, or a pharmaceutically acceptable salt thereof, and at least one pharmaceutically acceptable carrier.

19. A method for modulating receptor interacting serine/threonine-protein kinase 2 activity in a patient, comprising administering to said patient a therapeutically effective amount of a compound of claim 1, or a pharmaceutically acceptable salt thereof.

20. The method of claim 19, wherein the patient has an autoimmune disease or allergic disorder.

21. The method of claim 20, wherein the autoimmune disease or allergic disorder is selected from the group consisting or rheumatoid arthritis, psoriasis, systemic lupus erythromatosis, lupus nephritis, scleroderma, asthma, chronic obstructive pulmonary disease, allergic rhinitis, allergic eczema, multiple sclerosis, juvenile rheumatoid arthritis, juvenile idiopathic arthritis, type I diabetes, inflammatory bowel disease, graft versus host disease, psoriatic arthritis, reactive arthritis, ankylosing spondylitis, Crohn's disease, ulcerative colitis, uveitis and non-radiographicspondyloarthropathy.

22. A compound selected from the group consisting of:

177
-continued
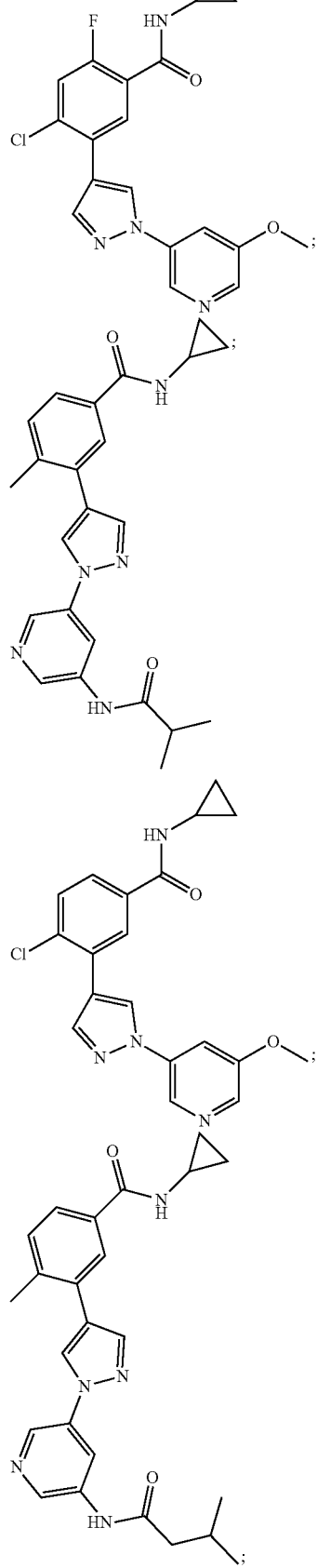
178
-continued
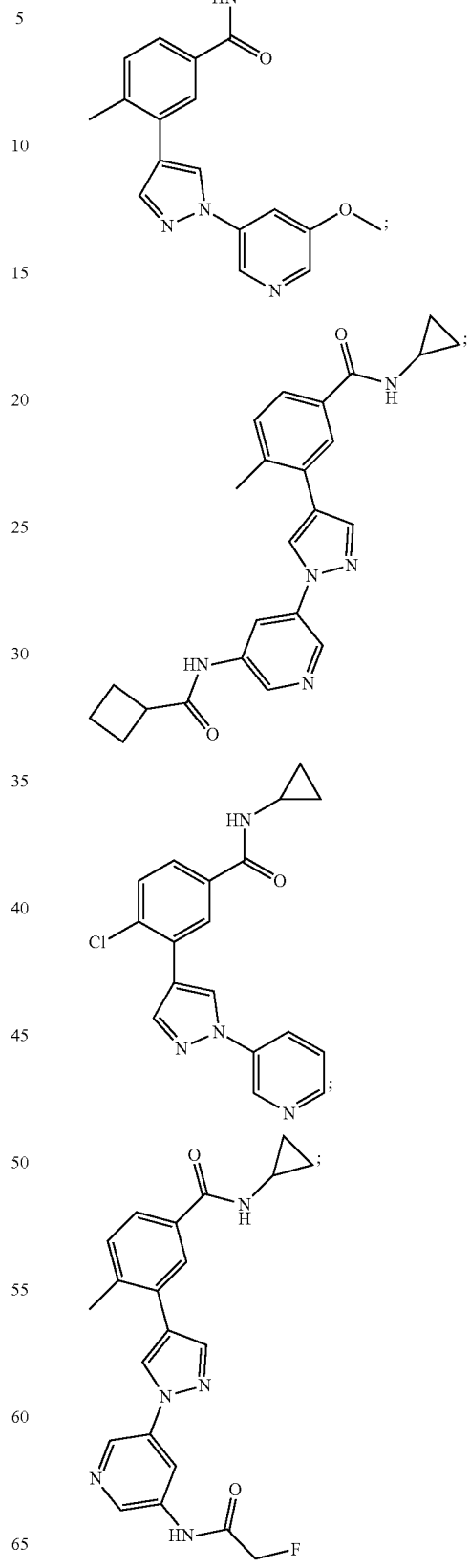

179
-continued
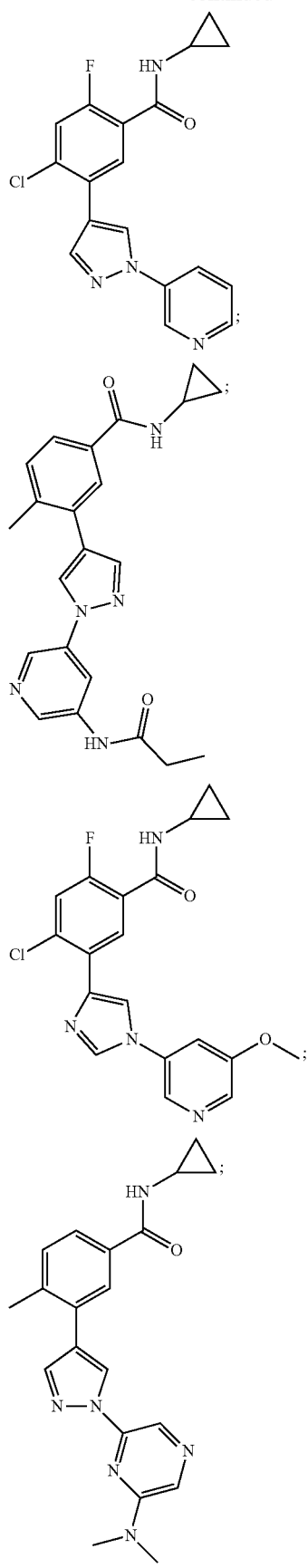
180
-continued
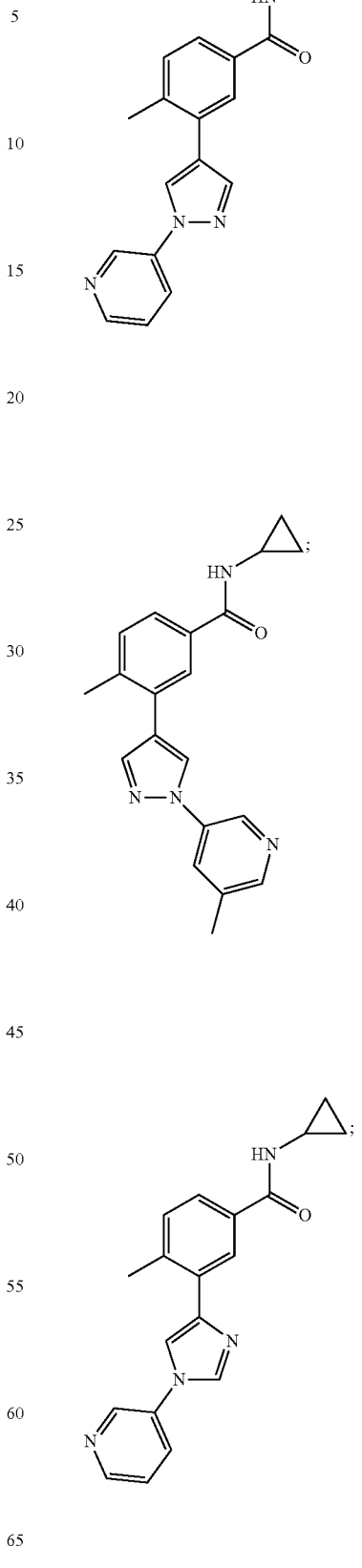

181
-continued
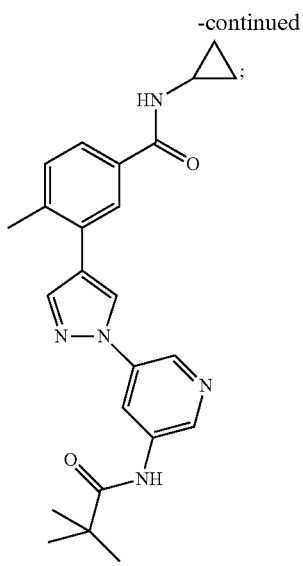
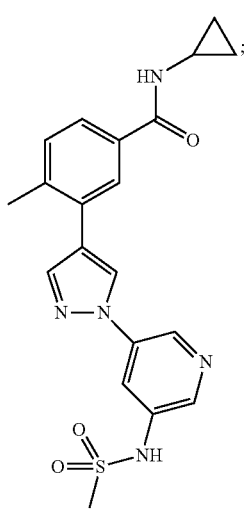
182
-continued
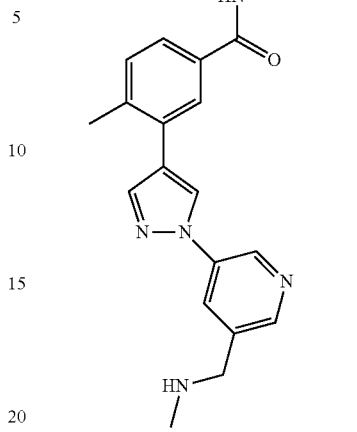
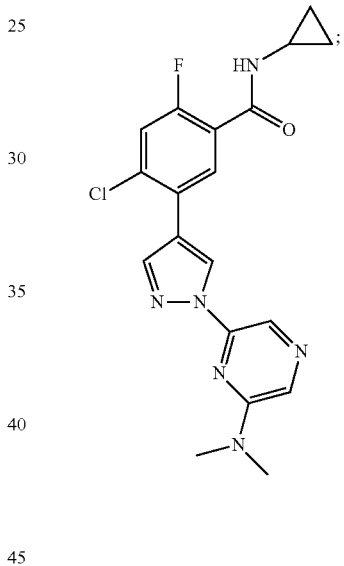
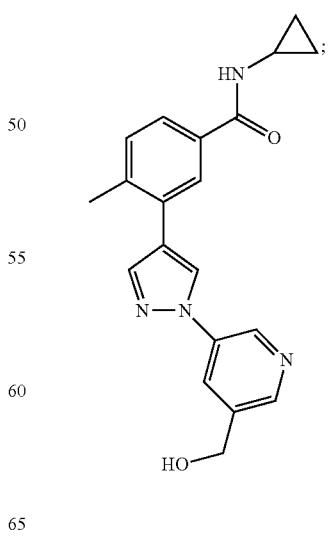

183
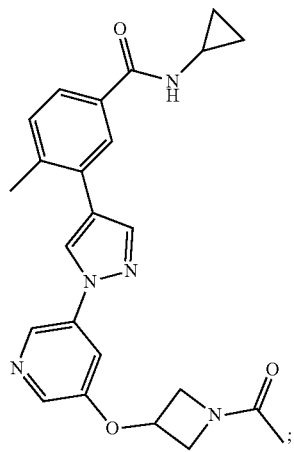
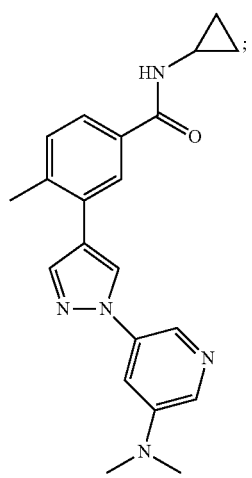
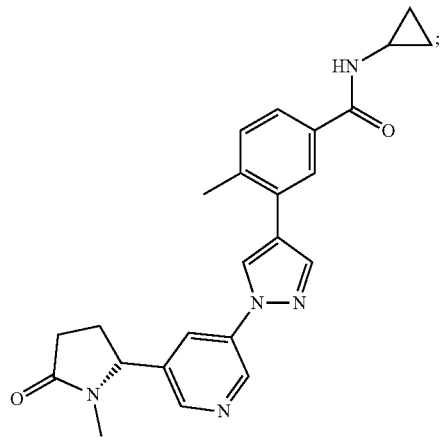
184
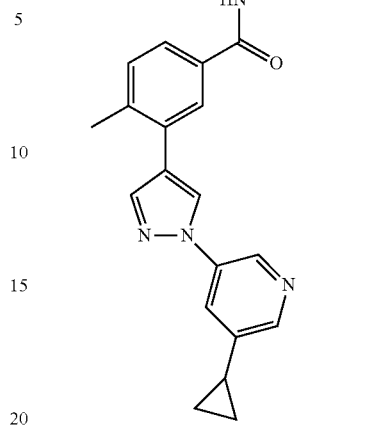
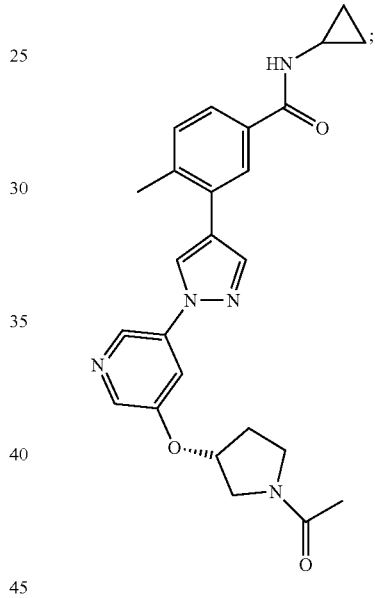
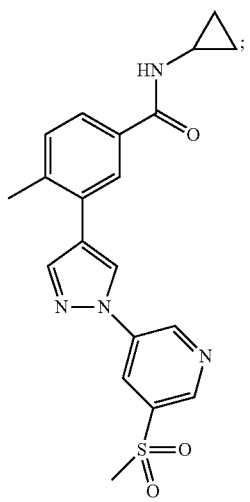

-continued
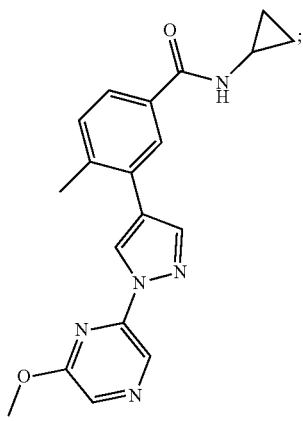
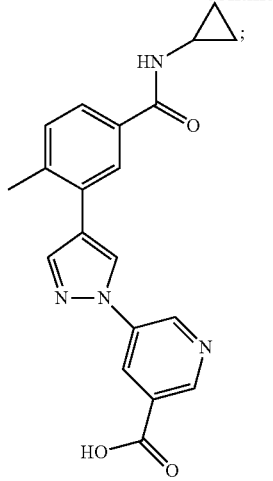
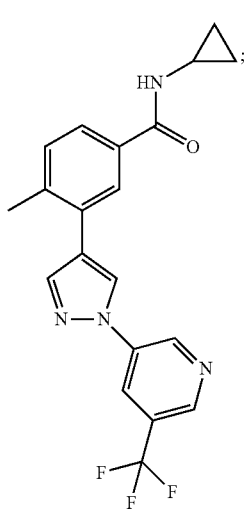
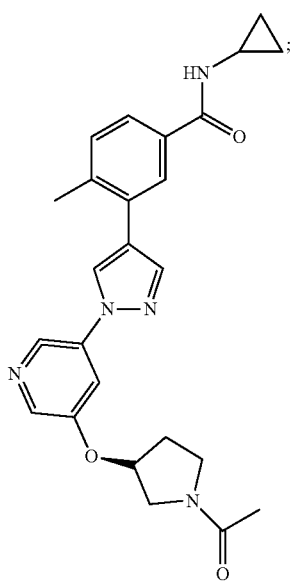
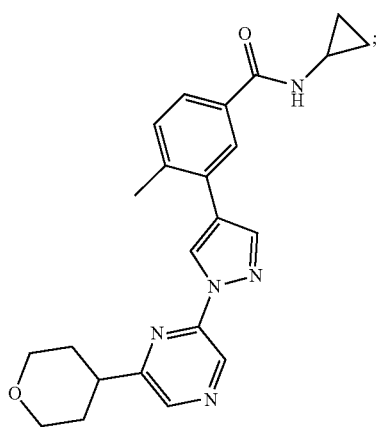
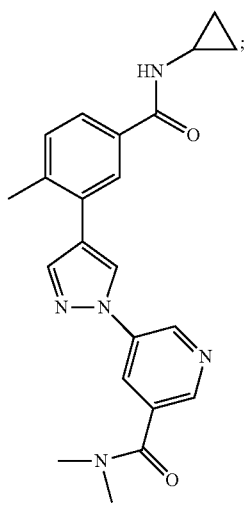

187
-continued
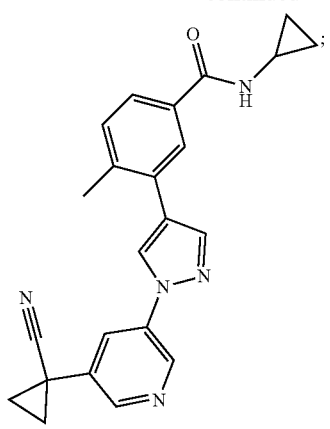
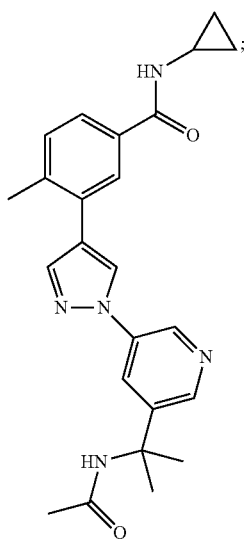
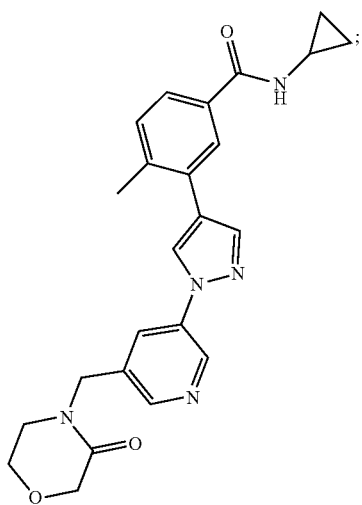
188
-continued
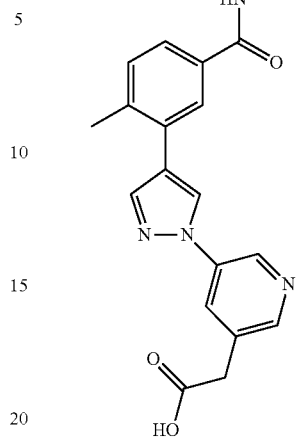
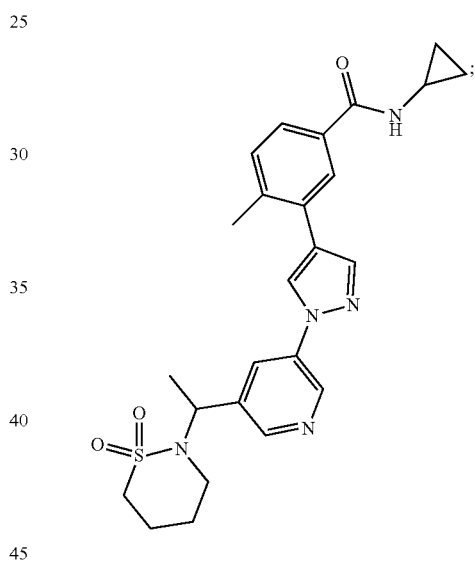
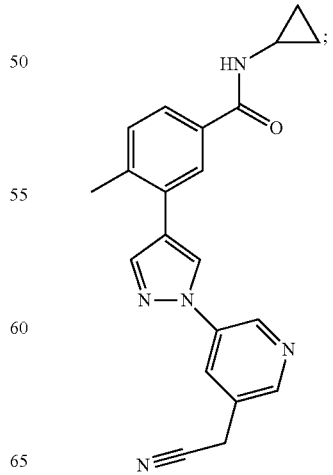

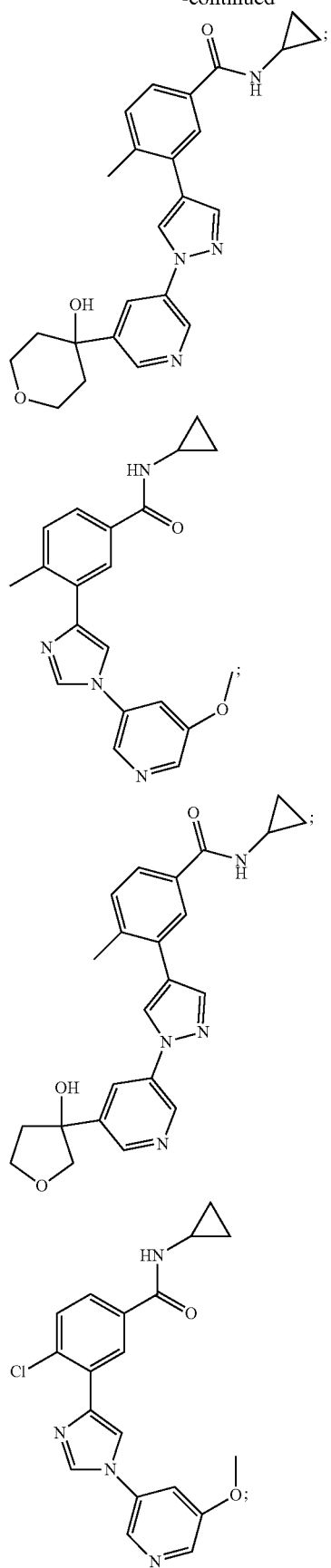
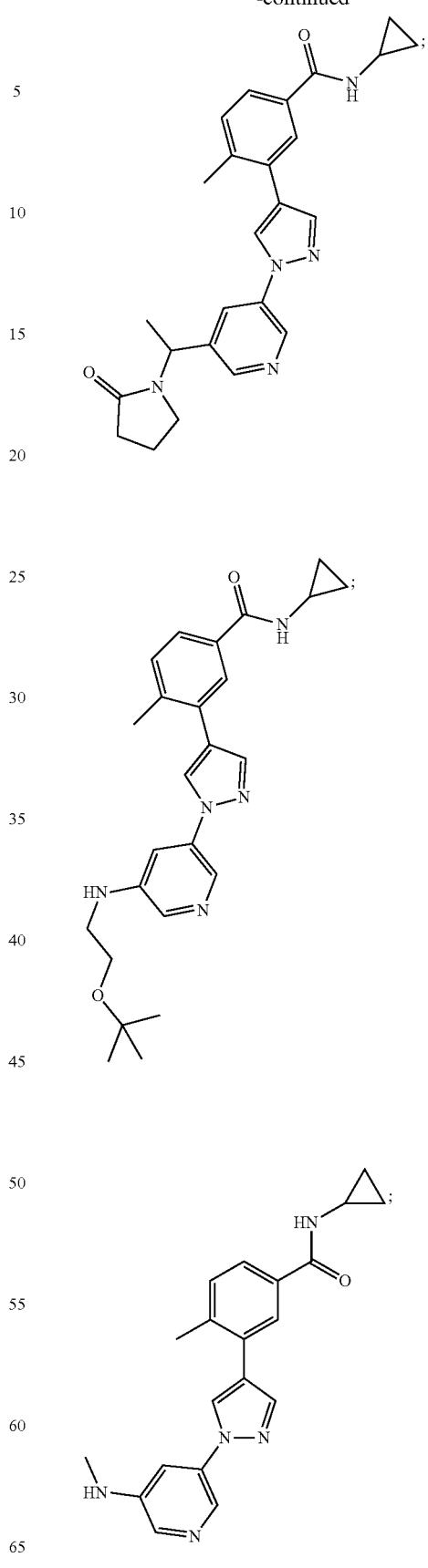

191
-continued
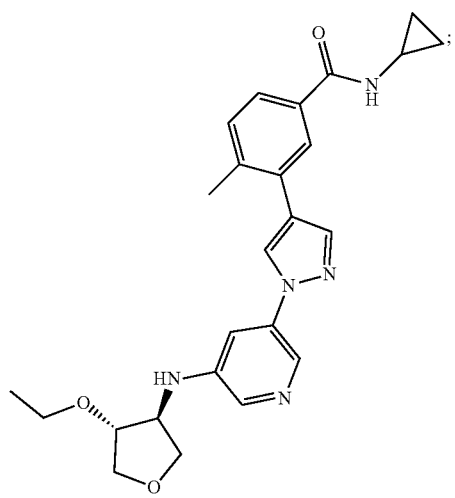
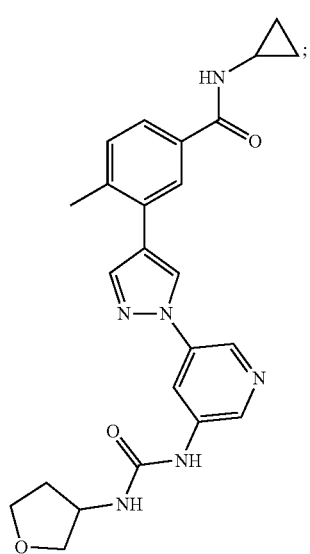
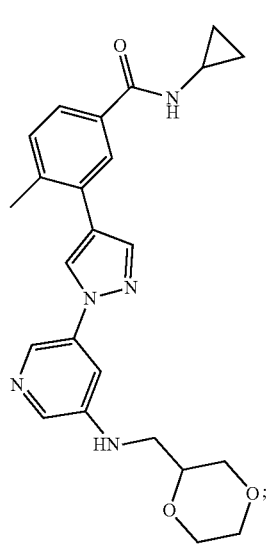
192
-continued
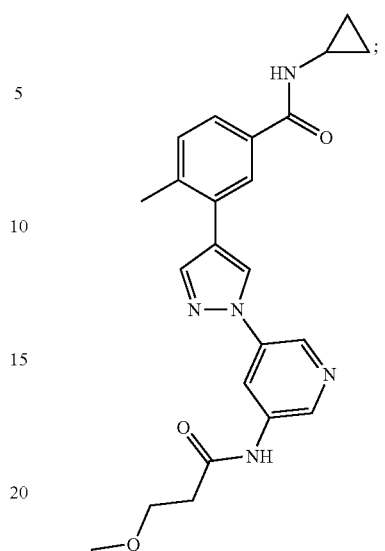
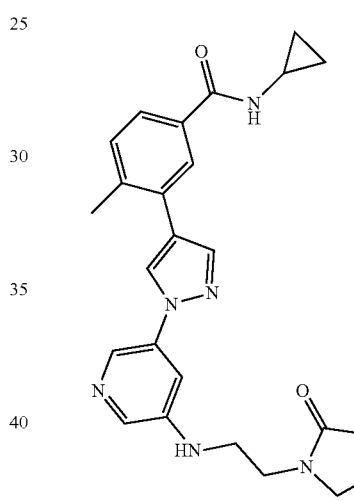
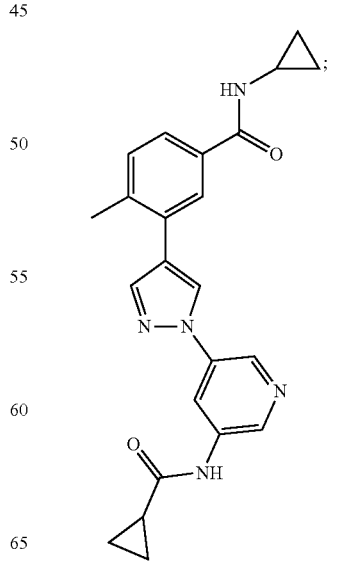

193
-continued
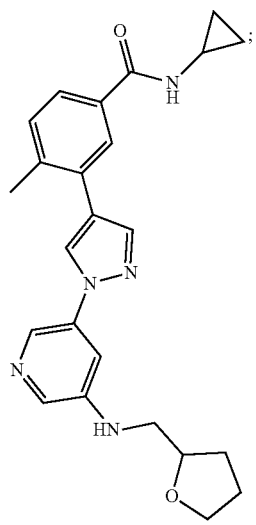
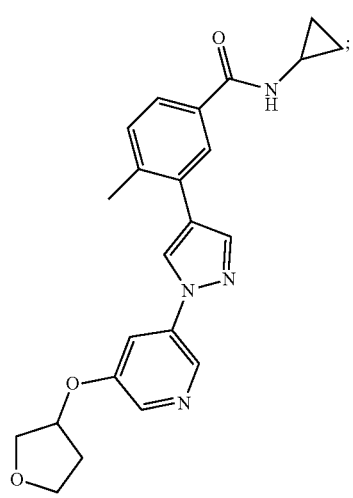
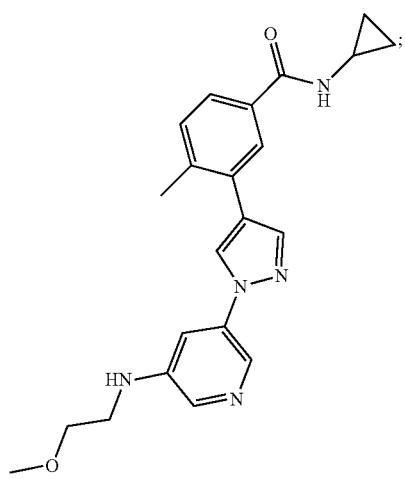
194
-continued
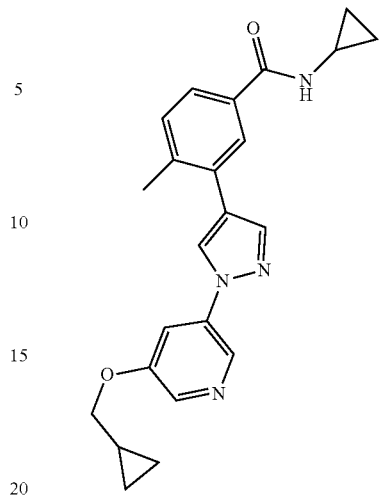
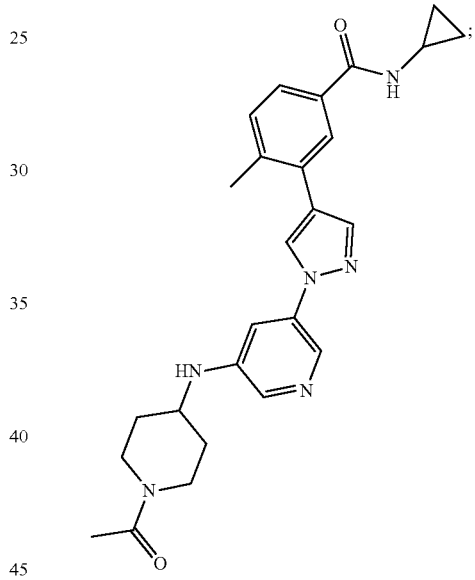
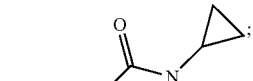

195
-continued
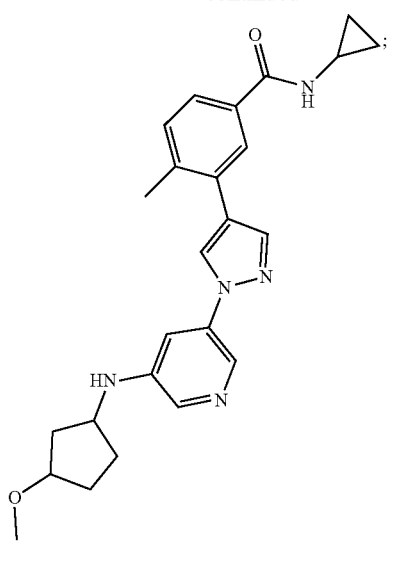
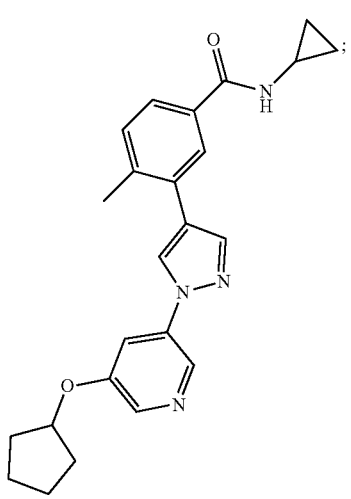
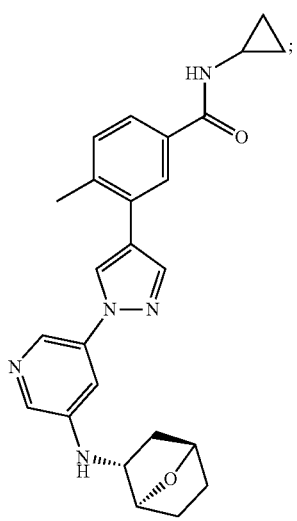
196
-continued
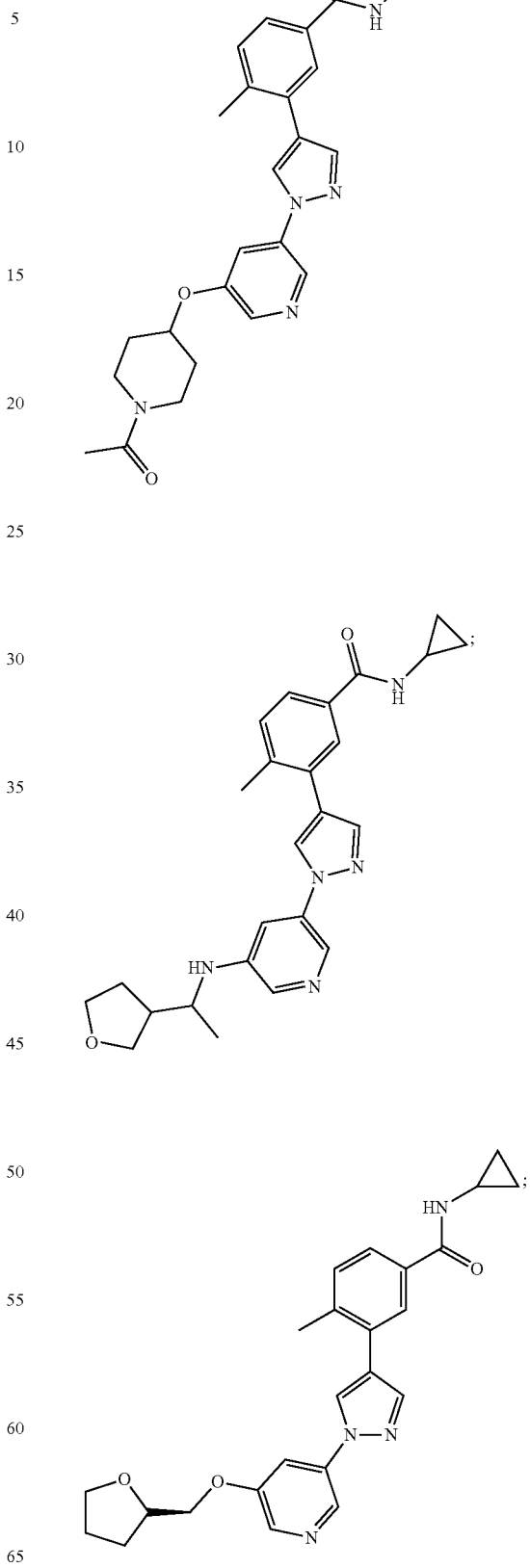

197
-continued
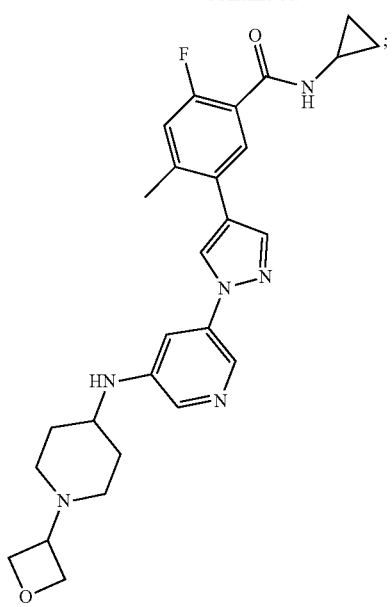
198
-continued
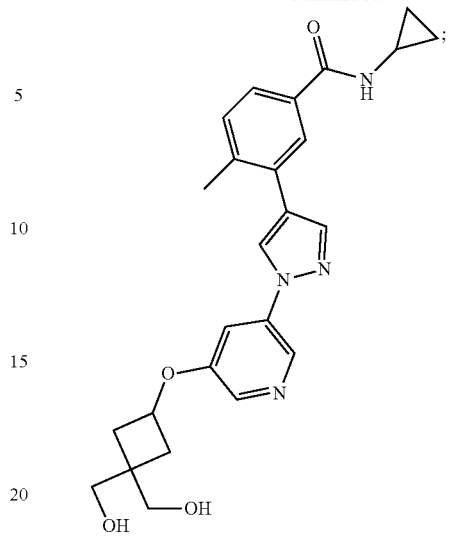
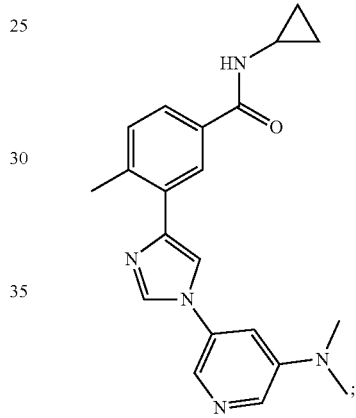
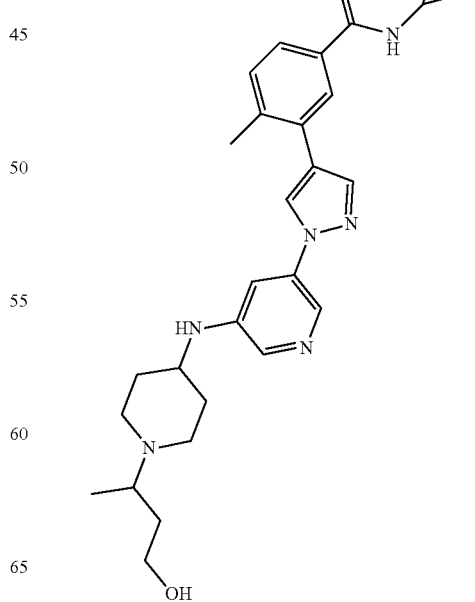

199
-continued
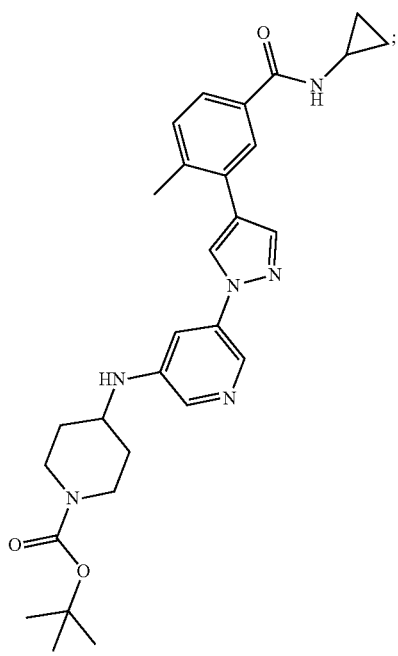
200
-continued
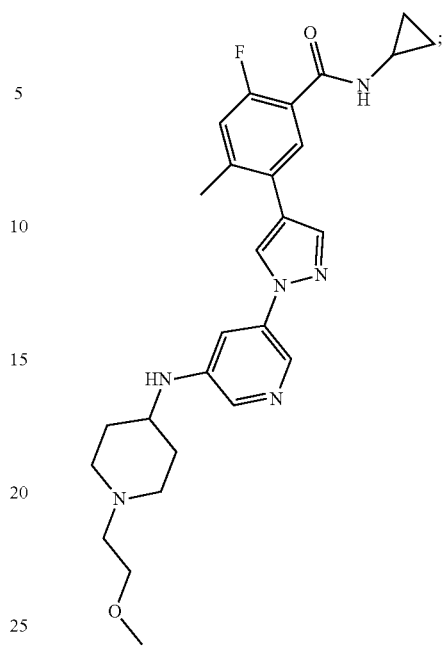
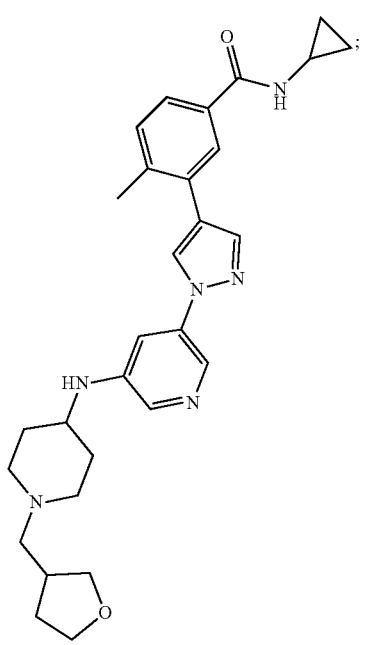
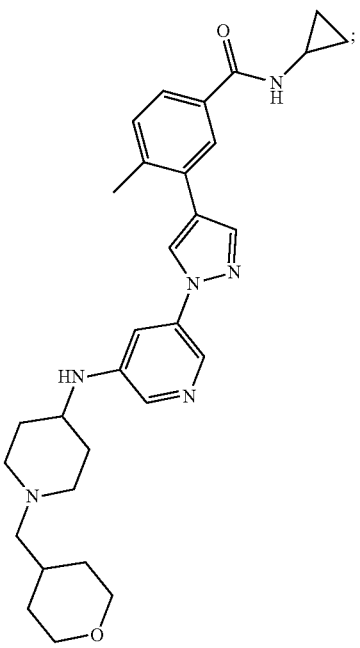

201
-continued
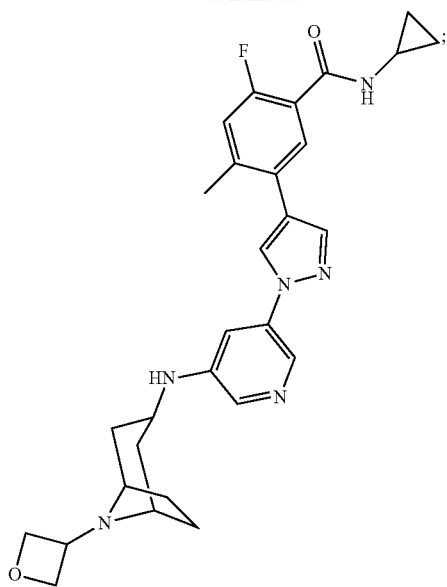
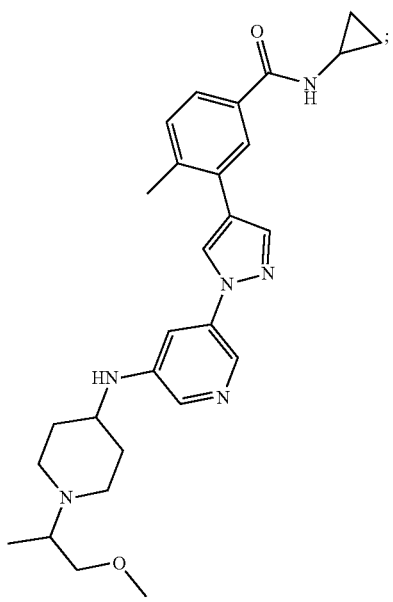
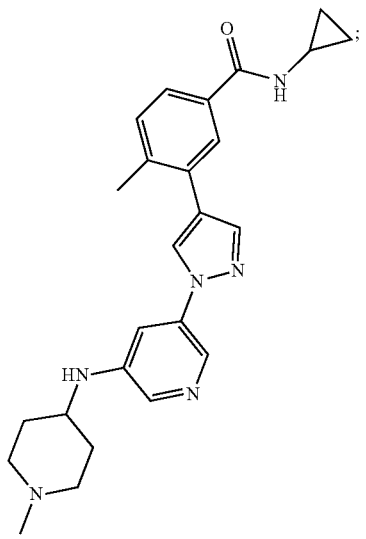
202
-continued
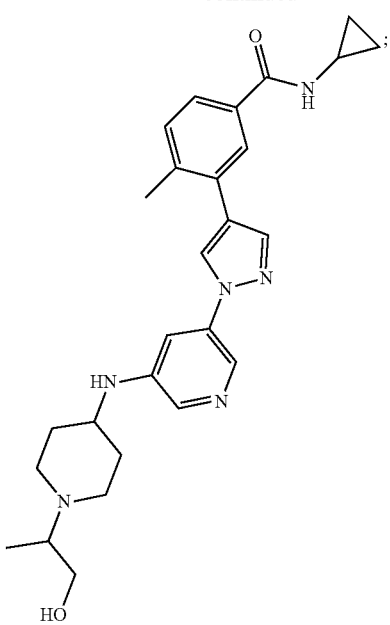
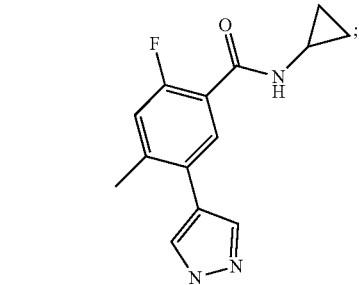
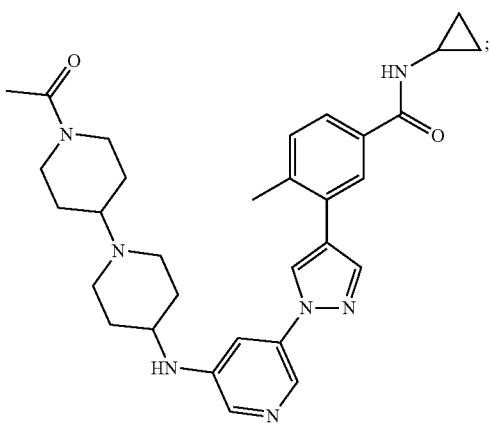

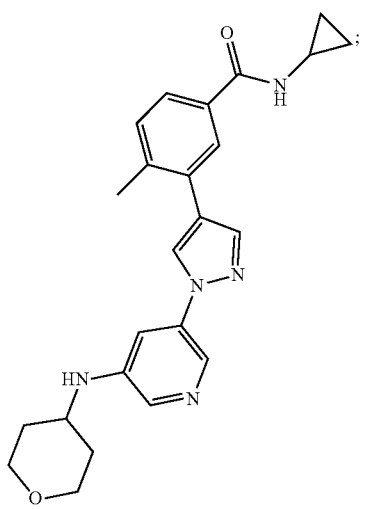
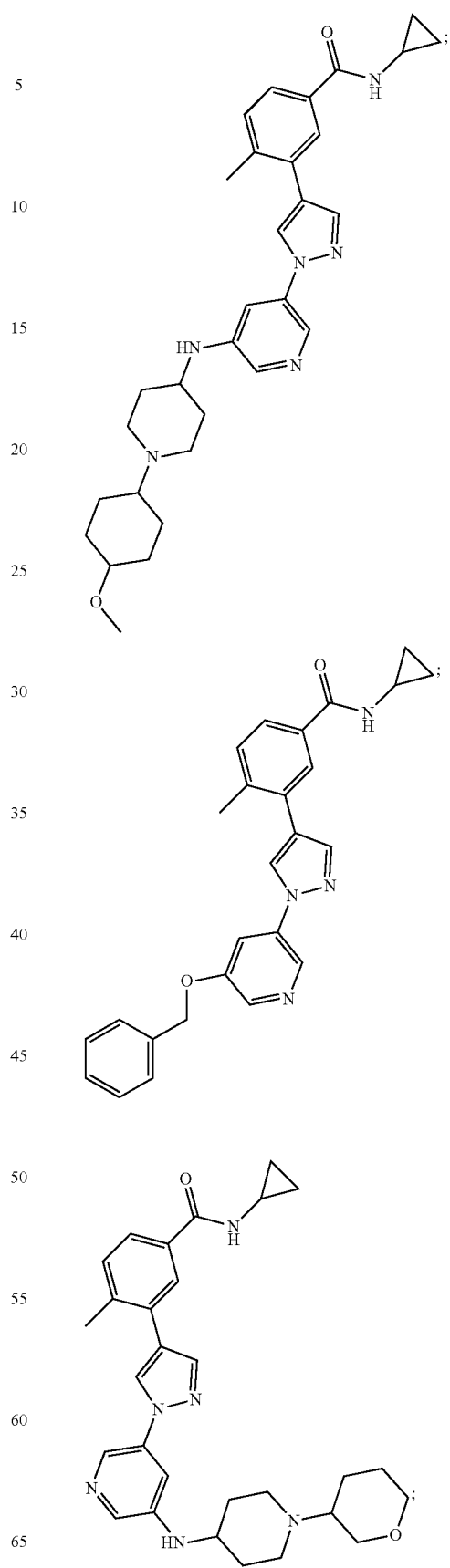

205
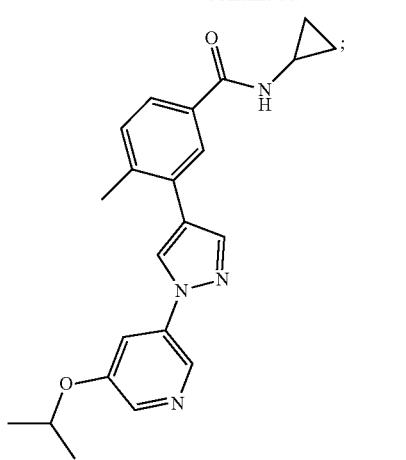
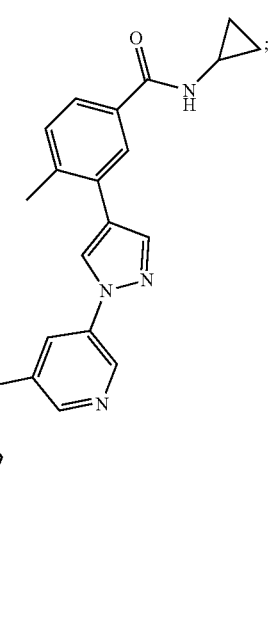
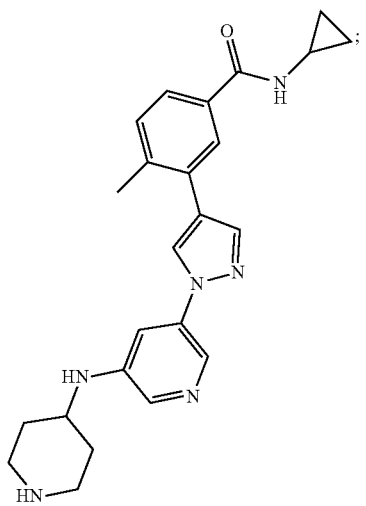
206
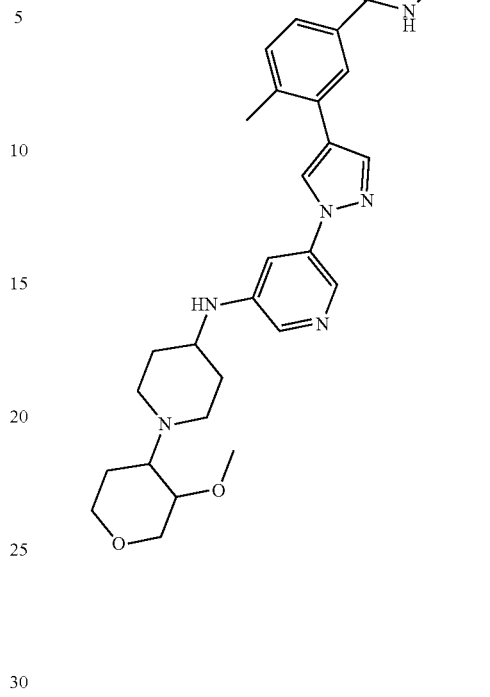
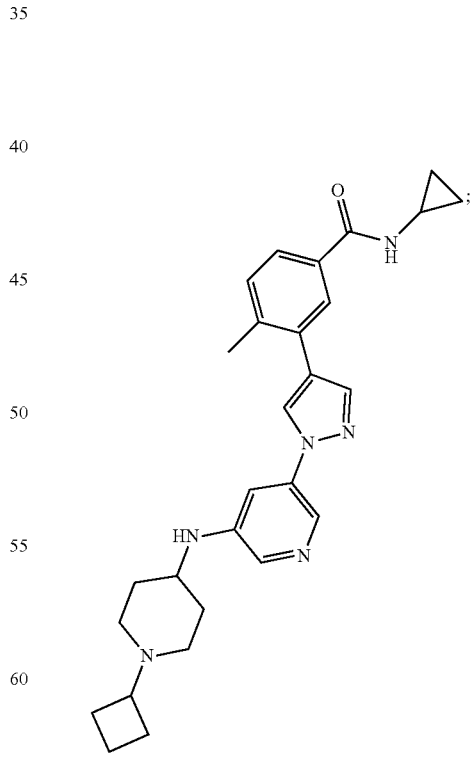

207
-continued
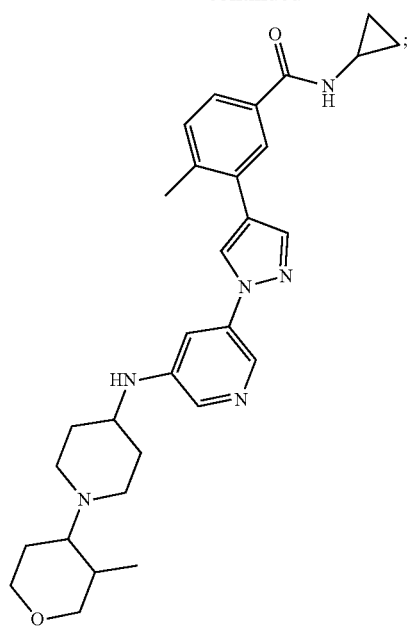
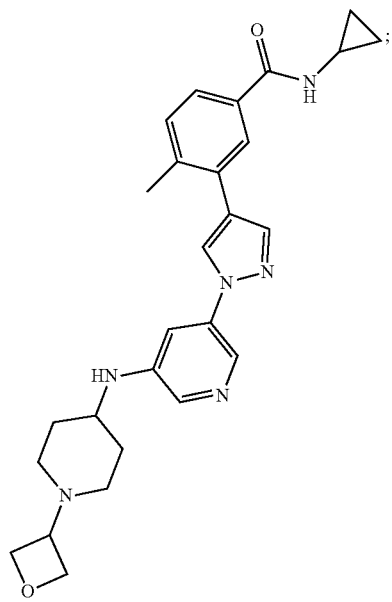
208
-continued
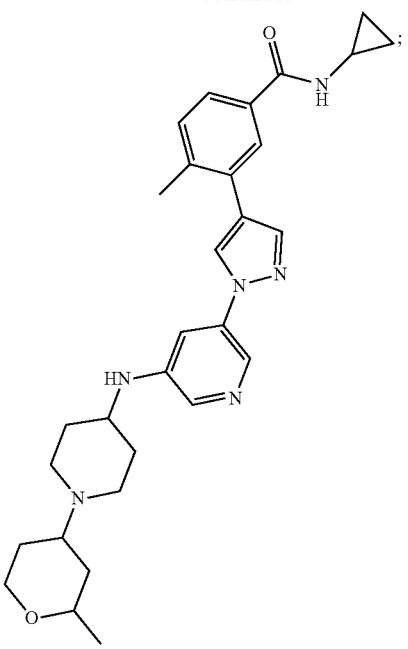
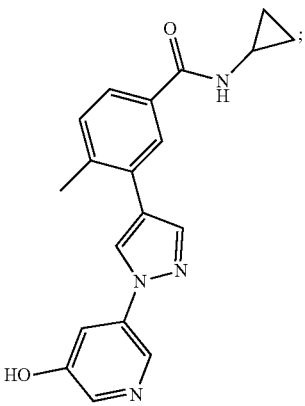
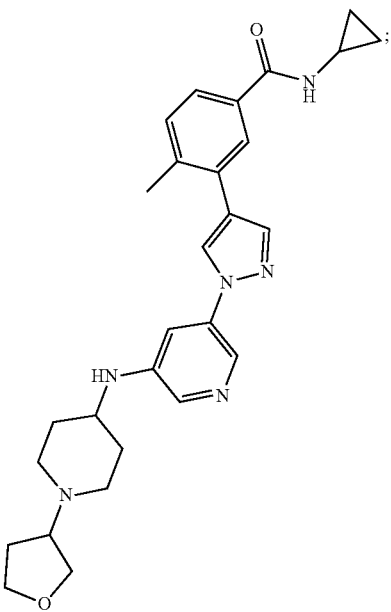

209
-continued
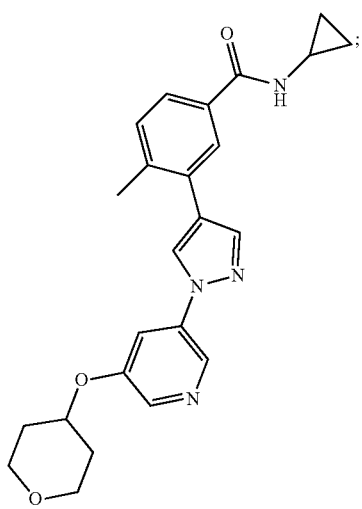
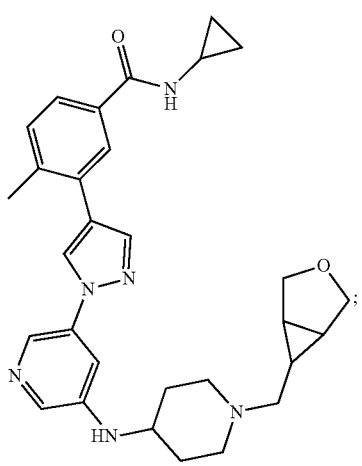
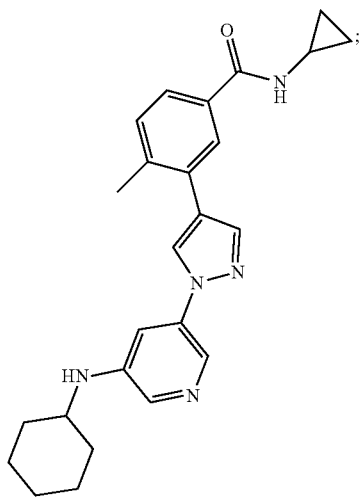
210
-continued
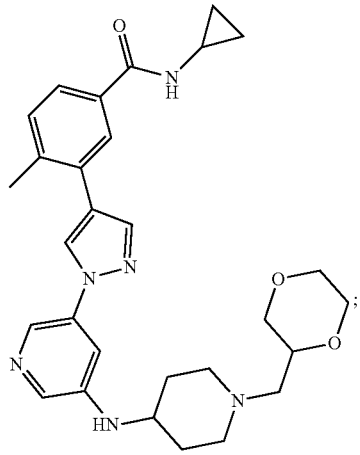
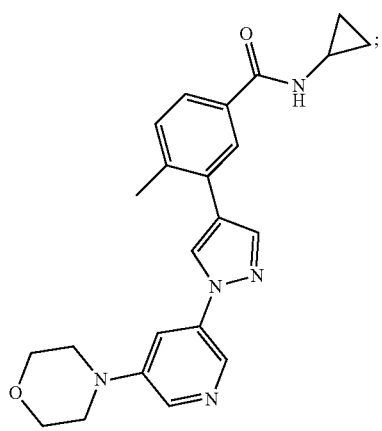

211
-continued
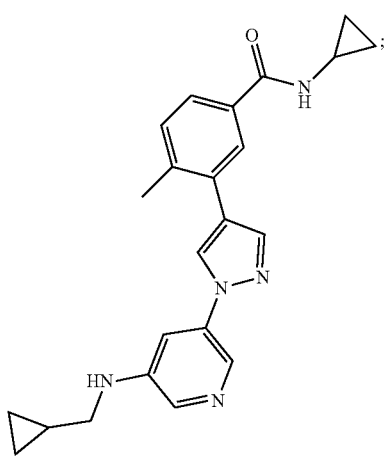
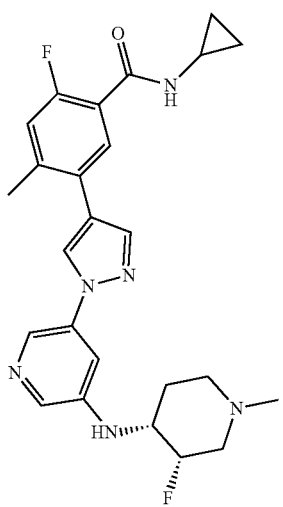
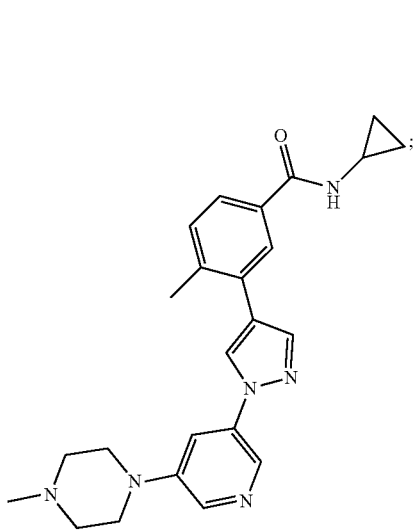
212
-continued
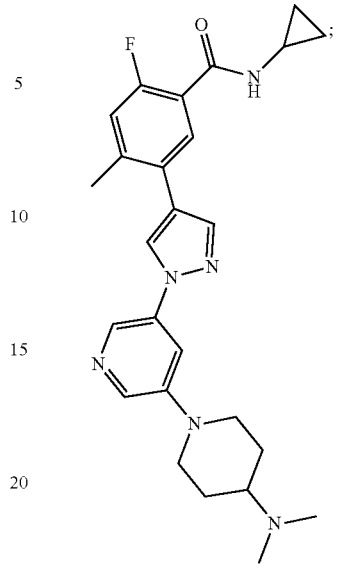
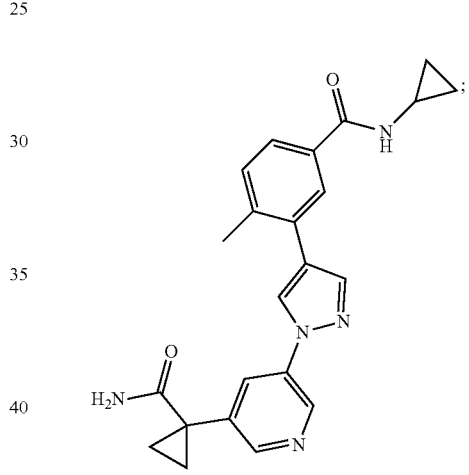
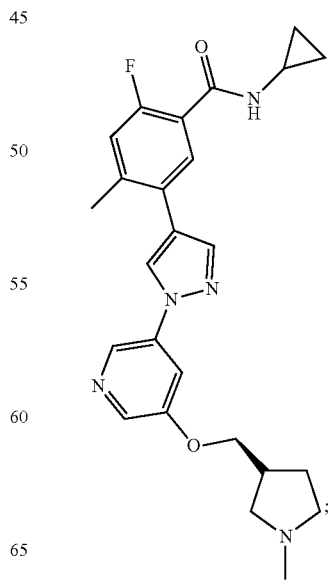

-continued
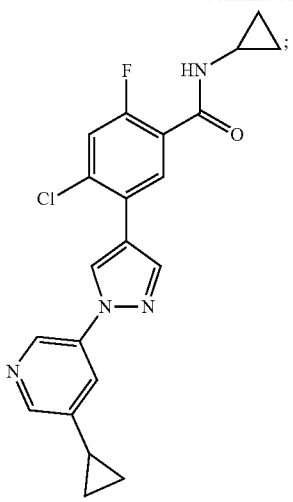
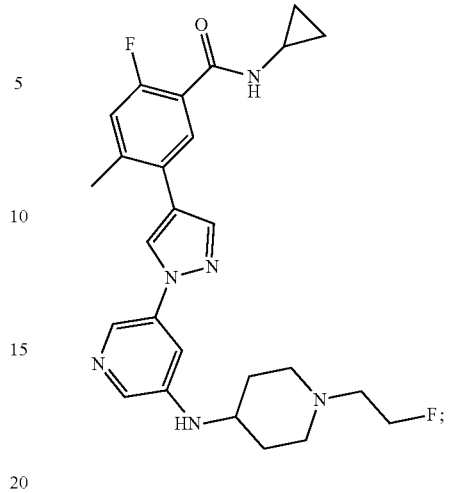
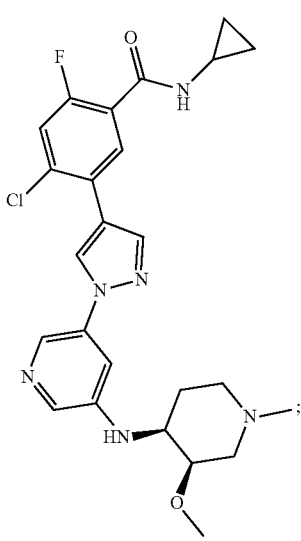
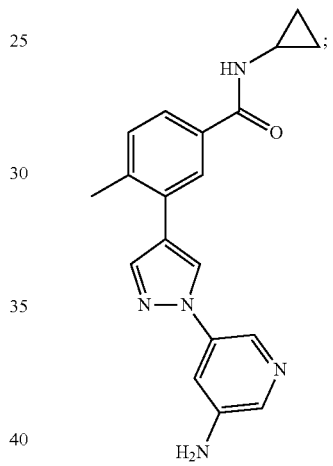
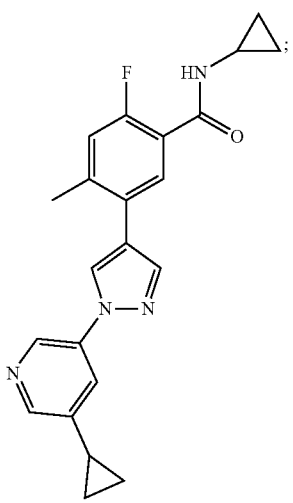

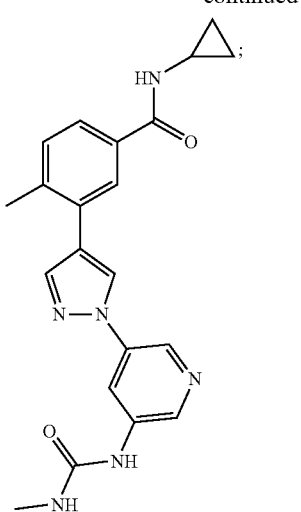
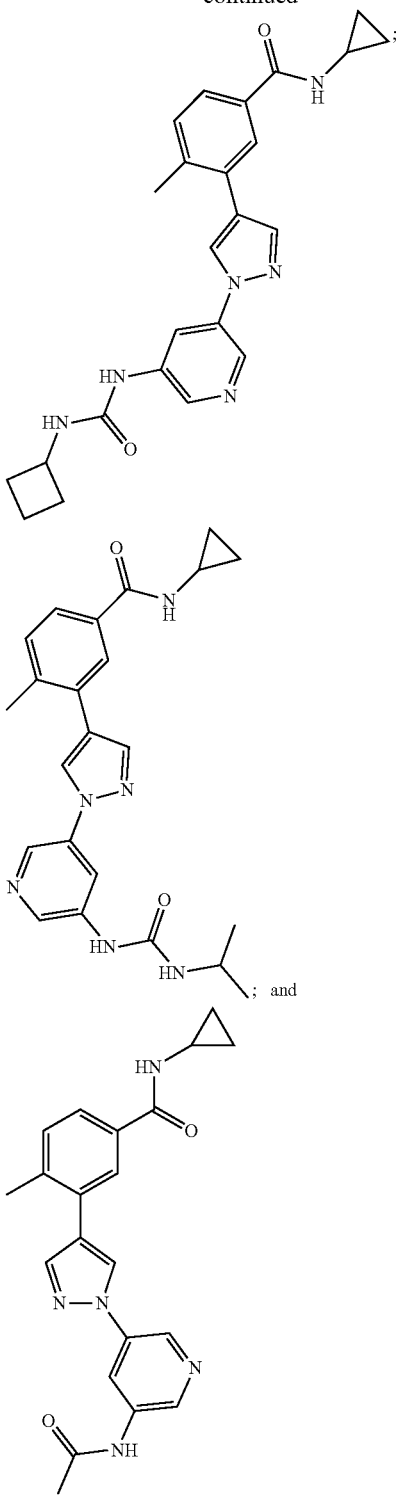
or the pharmaceutically acceptable salts thereof.
23. A pharmaceutical composition comprising a compound of claim 22, or a pharmaceutically acceptable salt thereof, and at least one pharmaceutically acceptable carrier.

24. The compound of claim 22, wherein the compound is:

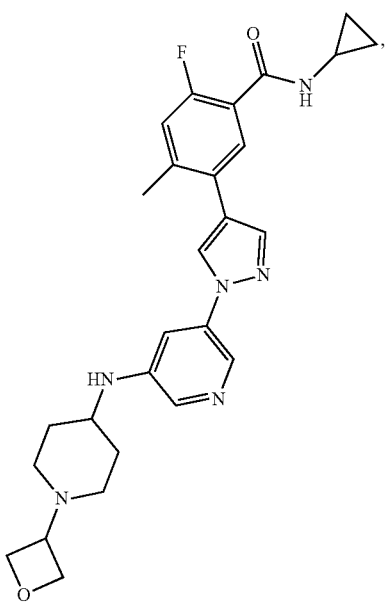 [SMILES: Cc1cc(F)c(C(=O)NC2CC2)cc1-c1cnn(-c2cncc(NC3CCN(C4COC4)CC3)c2)c1]

or a pharmaceutically acceptable salt thereof.

25. The compound of claim 22, wherein the compound is:

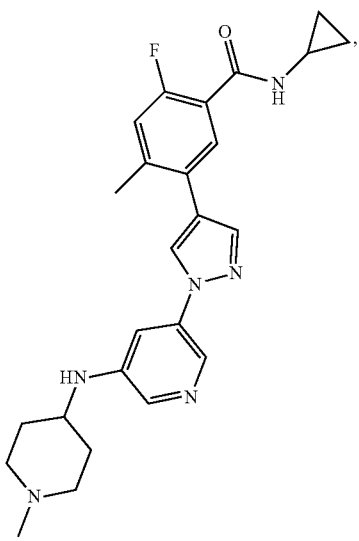 [SMILES: Cc1cc(F)c(C(=O)NC2CC2)cc1-c1cnn(-c2cncc(NC3CCN(C)CC3)c2)c1]

or a pharmaceutically acceptable salt thereof.

26. The compound of claim 22, wherein the compound is:

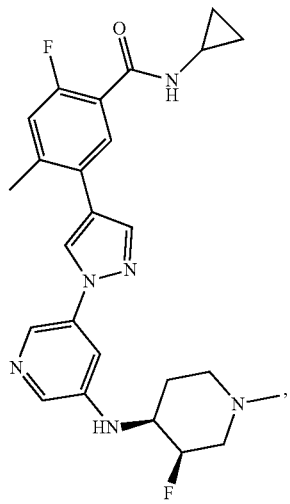

or a pharmaceutically acceptable salt thereof.

27. The compound of claim 22, wherein the compound is:

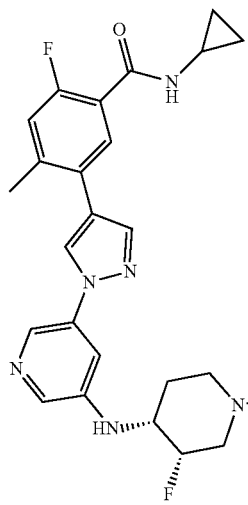

or a pharmaceutically acceptable salt thereof.

28. The compound of claim 22, wherein the compound is:

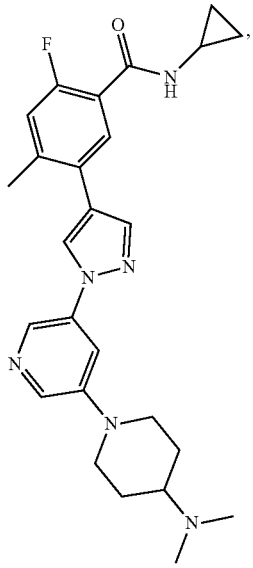 [SMILES: Cc1cc(F)c(C(=O)NC2CC2)cc1-c1cnn(-c2cncc(N3CCC(N(C)C)CC3)c2)c1]

or a pharmaceutically acceptable salt thereof.

29. The compound of claim 22, wherein the compound is:

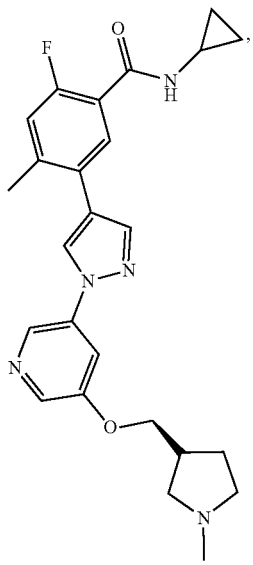

or a pharmaceutically acceptable salt thereof.

30. The compound of claim 22, wherein the compound is:

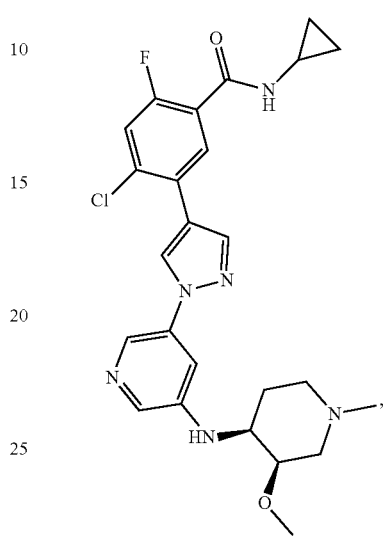

or a pharmaceutically acceptable salt thereof.

31. The compound of claim 22, wherein the compound is:

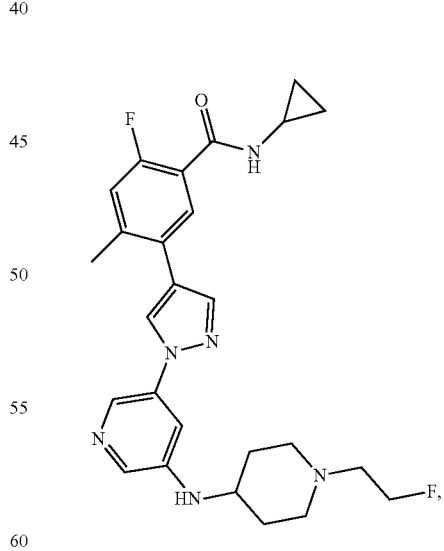

or a pharmaceutically acceptable salt thereof.

32. The compound of claim 22, wherein the compound is:
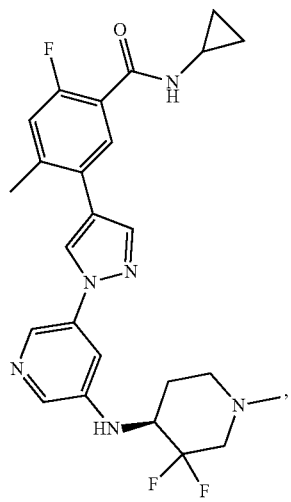
or a pharmaceutically acceptable salt thereof.
33. The compound of claim 22, wherein the compound is:
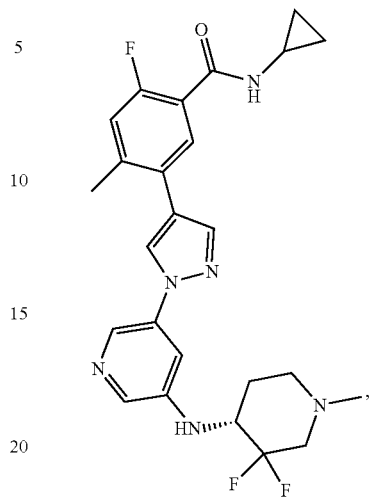
or a pharmaceutically acceptable salt thereof.
* * * * *